(12) United States Patent
Dihora et al.

(10) Patent No.: US 9,221,028 B2
(45) Date of Patent: Dec. 29, 2015

(54) DELIVERY PARTICLES

(71) Applicant: The Procter & Gamble Company, Cincinnati, OH (US)

(72) Inventors: Jiten Odhavji Dihora, Hamilton, OH (US); Johan Smets, Lubbeek (BE); Todd Arlin Schwantes, Lena, WI (US)

(73) Assignee: The Procter & Gamble Company, Cincinnati, OH (US)

( * ) Notice: Subject to any disclaimer, the term of this patent is extended or adjusted under 35 U.S.C. 154(b) by 88 days.

(21) Appl. No.: 14/045,670

(22) Filed: Oct. 3, 2013

(65) Prior Publication Data

US 2014/0227328 A1  Aug. 14, 2014

Related U.S. Application Data

(63) Continuation of application No. 12/777,314, filed on May 11, 2010.

(60) Provisional application No. 61/328,962, filed on Apr. 28, 2010.

(51) Int. Cl.
| | |
|---|---|
| *C11D 17/00* | (2006.01) |
| *B01J 13/16* | (2006.01) |
| *A61K 8/11* | (2006.01) |
| *A61K 8/92* | (2006.01) |
| *A61Q 5/02* | (2006.01) |
| *A61Q 5/12* | (2006.01) |
| *A61Q 15/00* | (2006.01) |
| *A61Q 19/00* | (2006.01) |
| *A61Q 19/10* | (2006.01) |
| *B01J 13/18* | (2006.01) |
| *C09B 67/02* | (2006.01) |
| *C11D 3/50* | (2006.01) |

(52) U.S. Cl.
CPC . *B01J 13/16* (2013.01); *A61K 8/11* (2013.01); *A61K 8/922* (2013.01); *A61Q 5/02* (2013.01); *A61Q 5/12* (2013.01); *A61Q 15/00* (2013.01); *A61Q 19/00* (2013.01); *A61Q 19/10* (2013.01); *B01J 13/185* (2013.01); *C09B 67/0097* (2013.01); *C11D 3/505* (2013.01); *C11D 17/003* (2013.01); *C11D 17/0013* (2013.01); *C11D 17/0039* (2013.01); *A61K 2800/412* (2013.01); *A61K 2800/56* (2013.01)

(58) Field of Classification Search
CPC ........................... C11D 3/505; C11D 17/0039
USPC ......................................................... 510/438
See application file for complete search history.

(56) References Cited

U.S. PATENT DOCUMENTS

| | | | |
|---|---|---|---|
| 5,071,706 A | 12/1991 | Soper | |
| 6,869,923 B1 | 3/2005 | Cunningham et al. | |
| 7,736,695 B2 | 6/2010 | Schwantes et al. | |
| 8,067,089 B2 | 11/2011 | Schwantes | |
| 8,071,214 B2 | 12/2011 | Schwantes | |
| 2004/0087470 A1* | 5/2004 | Grandmaire et al. | 510/504 |
| 2005/0089540 A1* | 4/2005 | Uchiyama et al. | 424/401 |
| 2005/0112152 A1 | 5/2005 | Popplewell et al. | |
| 2005/0276831 A1 | 12/2005 | Dihora et al. | |
| 2006/0263518 A1 | 11/2006 | Schwantes et al. | |
| 2006/0263519 A1 | 11/2006 | Schwantes et al. | |
| 2007/0123442 A1 | 5/2007 | Holzner et al. | |
| 2008/0182774 A1 | 7/2008 | Naraschkewitz et al. | |
| 2008/0200359 A1 | 8/2008 | Smets et al. | |
| 2008/0200363 A1 | 8/2008 | Smets et al. | |
| 2009/0274905 A1 | 11/2009 | Schwantes et al. | |
| 2009/0274906 A1* | 11/2009 | Schwantes | 428/402.22 |
| 2010/0040884 A1 | 2/2010 | Smets et al. | |
| 2011/0111999 A1* | 5/2011 | Smets et al. | 510/119 |
| 2011/0152147 A1* | 6/2011 | Smets et al. | 510/119 |
| 2012/0071391 A1 | 3/2012 | Smets et al. | |
| 2014/0037703 A1 | 2/2014 | Dihora et al. | |
| 2014/0079747 A1 | 3/2014 | Dihora et al. | |
| 2014/0079748 A1 | 3/2014 | Cetti et al. | |
| 2014/0086965 A1 | 3/2014 | Dihora et al. | |
| 2014/0178442 A1 | 6/2014 | Li et al. | |
| 2014/0227328 A1 | 8/2014 | Dihora et al. | |
| 2015/0086595 A1 | 3/2015 | Dihora | |

FOREIGN PATENT DOCUMENTS

| | | | |
|---|---|---|---|
| JP | 2007016161 | 1/2007 | |
| WO | WO 2005123892 | 12/2005 | |
| WO | WO 2008/005693 | * | 1/2008 |
| WO | WO 2008005693 | 1/2008 | |
| WO | WO 2008104352 | 9/2008 | |
| WO | WO 2008152543 | 12/2008 | |
| WO | WO 2008154765 | 12/2008 | |

* cited by examiner

*Primary Examiner* — John Hardee
(74) *Attorney, Agent, or Firm* — Jason J Camp; James F McBride

(57) ABSTRACT

The present application relates to encapsulated benefit agents, compositions comprising such encapsulated benefit agents and processes for making and using compositions comprising such encapsulated benefit agents. Such encapsulated benefit agents eliminate or minimize one or more of the drawbacks of current encapsulated benefit agents and thus provide formulators with additional perfume delivery opportunities.

20 Claims, No Drawings

DELIVERY PARTICLES

This is a continuation of pending U.S. patent application Ser. No. 12/777,514, filed May 11, 2010.

FIELD OF THE INVENTION

This invention relates to capsule manufacturing processes and microcapsules produced by such processes as well as compositions comprising such microcapsules and methods of making and using such compositions.

BACKGROUND OF THE INVENTION

Various processes for microencapsulation, and exemplary methods and materials are set forth in Schwantes (U.S. Pat. No. 6,592,990), Nagai et. al. (U.S. Pat. No. 4,708,924), Baker et. al. (U.S. Pat. No. 4,166,152), Wojciak (U.S. Pat. No. 4,093,556), Matsukawa et. al. (U.S. Pat. No. 3,965,033), Matsukawa (U.S. Pat. No. 3,660,304), Ozono (U.S. Pat. No. 4,588,639), Irgarashi et. al. (U.S. Pat. No. 4,610,927), Brown et. al. (U.S. Pat. No. 4,552,811), Scher (U.S. Pat. No. 4,285,720), Shioi et. al. (U.S. Pat. No. 4,601,863), Kiritani et. al. (U.S. Pat. No. 3,886,085), Jahns et. al. (U.S. Pat. Nos. 5,596,051 and 5,292,835), Matson (U.S. Pat. No. 3,516,941), Chao (U.S. Pat. No. 6,375,872), Foris et. al. (U.S. Pat. Nos. 4,001,140; 4,087,376; 4,089,802 and 4,100,103), Greene et. al. (U.S. Pat. Nos. 2,800,458; 2,800,457 and 2,730,456), Clark (U.S. Pat. No. 6,531,156), Saeki et. al. (U.S. Pat. Nos. 4,251,386 and 4,356,109), Hoshi et. al. (U.S. Pat. No. 4,221,710), Hayford (U.S. Pat. No. 4,444,699), Hasler et. al. (U.S. Pat. No. 5,105,823), Stevens (U.S. Pat. No. 4,197,346), Riecke (U.S. Pat. No. 4,622,267), Greiner et. al. (U.S. Pat. No. 4,547,429), and Tice et. al. (U.S. Pat. No. 5,407,609), among others and as taught by Herbig in the chapter entitled "Encapsulation" in Kirk Othmer, Encyclopedia of Chemical Technology, V.13, Second Edition, pages 436-456 and by Huber et. al. in "Capsular Adhesives", TAPPI, Vol. 49, No. 5, pages 41A-44A, May 1966, all of which are incorporated herein by reference.

More particularly, U.S. Pat. Nos. 2,730,456, 2,800,457; and 2,800,458 describe methods for capsule formation. Other useful methods for microcapsule manufacture are: U.S. Pat. Nos. 4,001,140; 4,081,376 and 4,089,802 describing a reaction between urea and formaldehyde; U.S. Pat. No. 4,100,103 describing reaction between melamine and formaldehyde; British Pat. No. 2,062,570 describing a process for producing microcapsules having walls produced by polymerization of melamine and formaldehyde in the presence of a styrene-sulfonic acid. Microcapsules are also taught in U.S. Pat. Nos. 2,730,457 and 4,197,346. Forming microcapsules from urea-formaldehyde resin and/or melamine formaldehyde resin is disclosed in U.S. Pat. Nos. 4,001,140; 4,081,376, 4,089,802; 4,100,103; 4,105,823; and 4,444,699. Alkyl acrylate-acrylic acid copolymer capsules are taught in U.S. Pat. No. 4,552,811. Each patent described throughout this application is incorporated herein by reference to the extent each provides guidance regarding microencapsulation processes and materials.

Interfacial polymerization is a process wherein a microcapsule wall of a polyamide, an epoxy resin, a polyurethane, a polyurea or the like is formed at an interface between two phases. U.S. Pat. No. 4,622,267 discloses an interfacial polymerization technique for preparation of microcapsules. The core material is initially dissolved in a solvent and an aliphatic diisocyanate soluble in the solvent mixture is added. Subsequently, a nonsolvent for the aliphatic diisocyanate is added until the turbidity point is just barely reached. This organic phase is then emulsified in an aqueous solution, and a reactive amine is added to the aqueous phase. The amine diffuses to the interface, where it reacts with the diisocyanate to form polymeric polyurethane shells. A similar technique, used to encapsulate salts which are sparingly soluble in water in polyurethane shells, is disclosed in U.S. Pat. No. 4,547,429. U.S. Pat. No. 3,516,941 teaches polymerization reactions in which the material to be encapsulated, or core material, is dissolved in an organic, hydrophobic oil phase which is dispersed in an aqueous phase. The aqueous phase has dissolved materials forming aminoplast resin which upon polymerization form the wall of the microcapsule. A dispersion of fine oil droplets is prepared using high shear agitation. Addition of an acid catalyst initiates the polycondensation forming the aminoplast resin within the aqueous phase, resulting in the formation of an aminoplast polymer which is insoluble in both phases. As the polymerization advances, the aminoplast polymer separates from the aqueous phase and deposits on the surface of the dispersed droplets of the oil phase to form a capsule wall at the interface of the two phases, thus encapsulating the core material. This process produces the microcapsules. Polymerizations that involve amines and aldehydes are known as aminoplast encapsulations. Urea-formaldehyde (UF), urea-resorcinol-formaldehyde (URF), urea-melamine-formaldehyde (UMF), and melamine-formaldehyde (MF), capsule formations proceed in a like manner. In interfacial polymerization, the materials to form the capsule wall are in separate phases, one in an aqueous phase and the other in a fill phase. Polymerization occurs at the phase boundary. Thus, a polymeric capsule shell wall forms at the interface of the two phases thereby encapsulating the core material. Wall formation of polyester, polyamide, and polyurea capsules typically proceeds via interfacial polymerization.

U.S. Pat. No. 5,292,835 teaches polymerizing esters of acrylic acid or methacrylic acid with polyfunctional monomers. Specifically illustrated are reactions of polyvinylpyrrolidone with acrylates such as butanediol diacrylate or methylmethacrylate together with a free radical initiator.

Common microencapsulation processes can be viewed as a series of steps. First, the core material which is to be encapsulated is typically emulsified or dispersed in a suitable dispersion medium. This medium is typically aqueous but involves the formation of a polymer rich phase. Most frequently, this medium is a solution of the intended capsule wall material. The solvent characteristics of the medium are changed such as to cause phase separation of the wall material. The wall material is thereby contained in a liquid phase which is also dispersed in the same medium as the intended capsule core material. The liquid wall material phase deposits itself as a continuous coating about the dispersed droplets of the internal phase or capsule core material. The wall material is then solidified. This process is commonly known as coacervation.

U.S. Pat. No. 4,046,750 teaches an ionene modified polymeric bead. Dimethylamino substituted acrylic polymer is cross-linked and then the formed beads are reacted with a mixture of ditertiary amine and a dihalide to attach ionene segments to the tertiary amine centers on the beads. Insoluble cationic modified beads are formed. These cationic beads are useful in affinity chromatography.

Microcapsule Technologies in WO 01/41915 teaches coating formed anionic microcapsules by adding compounds with a cationic charge in a controlled manner. For example polyurea capsules are introduced to a solution of vinylpyrrolidone to coat the capsules and render them with cationic character. Similarly melamine microcapsules are taught to be coated with a homogenous solution of hydroxypropyl guar to impact cationic character. Gelatin capsules are illustrated coated with hydroxyethyl cellulose followed by epichlorhydrin to render them cationic.

Firmenich in EP 1637188 describes flowable dispersions of coacervate capsules based on acrylamido methylpropane sulfonate with a thickening polymer of nonionic and cationic polymers. A complex between the anionic aminoplast capsules and cationic polymer is though beneficial to drive the deposition of the capsules from rinse off formulations onto surfaces to which the capsules are applied.

Similar to the approach of Microcapsule Technologies, U.S. publication 2005/0112152 also teaches applying a second coating of a cationic material over an acrylamide and melamine formaldehyde based wall. Cationic polymer coated capsules are taught prepared by mixing uncoated fragrance containing capsules with a cationic polymeric deposition aid.

Each of the above methods is deficient to form cationic microcapsules of low permeance and/or rely on multiple layers making the processes unattractive commercially.

Unfortunately, capsules manufactured using the aforementioned methods and raw materials have several drawbacks which include: (1) they cannot be formulated in certain classes of products due to strict formulation limits, (2) they have high permeabilities when incorporated into products that contain high levels of surfactant, solvents, and/or water, which results in the premature benefit agent release, (3) they can only effectively encapsulate a limited breadth of benefit agents, and (4) they either are so stable that they do not release the benefit agent in use or have insufficient mechanical stability to withstand the processes required to incorporate them in and/or make a consumer product and (5) they do not adequately deposit on the situs that is being treated with consumer product that contains capsules.

Capsules made according to the invention can be made to better control permeability characteristics. Capsules made according to the invention are surprisingly better able to contain liquid contents without leakage over time. The capsules can be made less leaky than those made by comparable prior art processes. Alternatively permeability in certain applications is desired. Through selection of wall material and control of length of time of cross-linking or temperature of cross-linking, capsules can be made with differing permeability profiles from extremely tight with little to no leakage to capsules that have measurable permeability useful where a measurable release rate over time is desired.

The capsules according to the invention are useful with a wide variety of capsule contents ("core materials") including, by way of illustration and without limitation, perfumes; brighteners; insect repellants; silicones; waxes; flavors; vitamins; fabric softening agents; skin care agents; enzymes; probiotics; dye polymer conjugate; dye clay conjugate; perfume delivery system; sensates in one aspect a cooling agent; attractants, in one aspect a pheromone; anti-bacterial agents; dyes; pigments; bleaches; flavorants; sweeteners; waxes; pharmaceuticals; fertilizers; herbicides and mixtures thereof. The microcapsule core materials can include materials which alter rheology or flow characteristics, or extend shelf life or product stability. Essential oils as core materials can include, for example, by way of illustration wintergreen oil, cinnamon oil, clove oil, lemon oil, lime oil, orange oil, peppermint oil and the like. Dyes can include fluorans, lactones, indolyl red, I6B, leuco dyes, all by way of illustration and not limitation. The core material should be dispersible or sufficiently soluble in the capsule internal phase material namely in the internal phase oil or soluble or dispersible in the monomers or oligomers solubilized or dispersed in the internal phase oil. When the internal phase is water, the core material should be dispersible or sufficiently soluble in the water phase. The invention is particularly useful to encapsulate volatile fragrances and flavorants. When a water phase is being microencapsulated, with the oil phase serving as the continuous phase, the core material should be soluble or dispersible in the water phase so as to form a dispersion in water that can be emulsified into the oil phase.

In alternative embodiments, capsules according to the invention are also able to be fashioned with thermoplastic polymeric materials resulting in low leakage heat sensitive capsules that could be opened with heat in addition to conventional techniques such as pressure, scraping, friction, shearing, impact, or other energy input. The capsules according to the invention can also be useful in applications with thermal print heads, or lasers, or other heating or impact elements. In alternative embodiments, if a light stimulated material is included, light sensitive capsules are also feasible.

The permeability characteristics of the capsules disclosed herein have versatility for a variety of applications. Wherever an internal phase is desired to be held securely over time but available to be exuded or released upon fracture or breakage of the capsules such as with application of pressure, a low permeability capsule according to the invention can be fashioned. Where measurable release is desired, more permeable capsules can also be fashioned. Where adhesion on surfaces such as textiles and anionic substrates is desired, cationic capsules can also be fashioned.

SUMMARY OF THE INVENTION

A method of forming a composition comprising water in oil, and oil in water microcapsules is disclosed. According to the invention microcapsules are obtained through either oil in water (O/W) or water in oil (W/O) emulsifications. In one embodiment microcapsules are obtained by steps comprising dispersing an oil soluble amine modified polyfunctional polyvinyl monomer (or oligomer) and an oil soluble bi- or polyfunctional vinyl monomer or oligomer along with a free radical initiator such as an azo or peroxy initiator and an organic acid into an internal phase oil which is a non-solvent for the water phase. The phase in excess is water with O/W emulsification. With W/O emulsifications the phase in excess or continuous phase is oil. The term internal phase oil is used for convenience and simplicity to refer to the oil phase and to refer to the type of oils conventionally used as the internal phase or contents of microcapsules in conventional microencapsulation (with the W/O emulsifications taught herein, the oil however ends up being the continuous phase. The water phase forms the capsule internal contents. The term "oil phase" is intended to refer to the oil phase oil.) The oil phase dispersion is heated for a time and temperature sufficient to oligomerize the amine modified polyfunctional polyvinyl monomer or oligomer and oil soluble bi- or polyfunctional vinyl monomer or oligomer forming a pre-polymer. The next step is adding to the oil phase a water phase comprising a dispersion in water of an emulsifier and an optional second initiator which can be the same or different such as an azo or peroxy initiator. This water phase is emulsified into the oil phase (W/O) followed by heating for a time and temperature sufficient to decompose at least one of the free radical initiators, which can be placed in either or both of the oil and/or water phases; thereby forming microcapsule wall material at the interface of the water and oil phases. A third heating step is used to polymerize the formed wall material and in the process, preferably decomposing any remaining initiator.

In a second embodiment, microcapsules are obtained by steps comprising dispersing an oil soluble amine modified ethoxylated trimethylol propane triacrylate and an oil soluble diethylene glycol dimethacrylate along with a free radical initiator such as an azo initiator and an organic acid into an internal oil phase; heating for time and temperature sufficient to oligomerize the amine modified ethoxylated trimethylol propane triacrylate and a diethylene glycol dimethacrylate forming a pre-polymer; then, adding to the oil phase a water phase comprising a dispersion of water, and an emulsifier, and an optional second initiator. The water phase is then emulsified into the oil phase (W/O) and heated for a time and temperature sufficient to decompose at least one of the free radical initiators in either or both of the oil and water phases; thereby forming microcapsule wall material at the interface of the water and oil phases.

In an alternative embodiment involving an oil in water (O/W) emulsion, microcapsules are obtained by steps comprising dispersing an oil soluble amine modified polyfunctional polyvinyl monomer and an oil soluble bi- or polyfunctional vinyl monomer or oligomer along with a free radical azo initiator and an organic acid into an internal phase; then, heating for a time and temperature sufficient to oligomerize or further oligomerize the amine modified polyfunctional polyvinyl monomer or oligomer and oil soluble bi- or polyfunctional vinyl monomer forming a pre-polymer; then, adding to the oil phase a water phase in excess comprising a dispersion in water of an emulsifier and an optional second initiator, and adding an emulsifying agent; emulsifying the oil phase into the water phase; then heating for a time and temperature sufficient to decompose the free radical initiators in either or both of the oil and water phases; thereby forming microcapsule wall material at the interface of the water and oil phases.

In yet another embodiment involving an oil in water emulsion (O/W) process, microcapsules are obtained by steps comprising dispersing an oil soluble amine modified ethoxylated trimethylol propane triacrylate and an oil soluble diethylene glycol dimethacrylate along with a free radical initiator such as an initiator and an organic acid into an internal phase oil; heating for time and temperature sufficient to oligomerize the amine modified ethoxylated trimethylol propane triacrylate and a diethylene glycol dimethacrylate forming a pre-polymer; then, adding to the internal phase oil a water phase comprising a dispersion of water, and an emulsifier, emulsifying the oil phase into the water phase; then heating for a time and temperature sufficient to decompose the free radical initiators in the oil and water phases; thereby forming microcapsule wall material at the interface of the water and oil phases. Optionally, the free radical initiator can be included in one or both of the oil and water phase.

In one embodiment the invention comprises microcapsules obtained by steps comprising dispersing an oil soluble amine modified polyfunctional polyvinyl monomer or oligomer and an oil soluble bi- or polyfunctional vinyl monomer or oligomer along with a free radical initiator and an organic acid into an internal phase oil. A first heating step is used comprising, heating for a time and temperature sufficient to oligomerize or further oligomerize the amine modified polyfunctional polyvinyl monomer or oligomer and oil soluble bi- or polyfunctional vinyl monomer oligomer forming a pre-polymer. A water phase comprising a dispersion in water of an emulsifier and a free radical initiator is added to the internal phase oil. The water phase is emulsified into the oil phase. A second heating step is used comprising, heating for a time and temperature sufficient to decompose the free radical initiators in the oil and water phases thereby forming microcapsule wall material at the interface of and oil phases. Then a third heating step comprising heating to a temperature equal to or greater than the second heating step temperature is used for a time sufficient to polymerize the wall material. The free radical initiator is preferably selected from an azo or peroxy initiator. Oligomerization in one embodiment is accomplished by heating, in the first heating step, to at least 55° C. for at least one hour to form the prepolymer.

In an alternative embodiment the initiator in the oil phase decomposes at a first temperature and the initiator in the water phase decomposes at a second temperature. In a yet further embodiment the invention comprises microcapsules obtained by steps comprising dispersing an oil soluble amine modified polyfunctional polyvinyl monomer or oligomer and an oil soluble bi- or polyfunctional vinyl monomer or oligomer along with a free radical initiator and an organic acid into an internal phase oil; a first heating step comprising, heating for a time and temperature sufficient to oligomerize or further oligomerize the amine modified polyfunctional polyvinyl monomer or oligomer and oil soluble bi- or polyfunctional vinyl monomer or oligomer forming a pre-polymer; adding to the internal phase oil a water phase in excess comprising a dispersion in water of a polyacrylic or polymethacrylic acid, and a free radical initiator, and adding an emulsifying agent; emulsifying the oil phase into the water phase; and a second heating step comprising, heating for a time and temperature sufficient to decompose the free radical initiator in the oil and water phases; thereby forming microcapsule wall material at the interface of the water and oil phases; and, a third heating step comprising heating to a temperature equal to or greater than the second heating step temperature for a time sufficient to polymerize the wall material.

In one embodiment the oligomerization is accomplished by heating, in the first heating step, is to at least 55° C. for at least one hour to form the prepolymer and the third heating step is to at least 90° C. for at least three hours. The second heating step comprised heating to a temperature equal to or greater than the first step, preferably greater. The second step temperature could involve dropping the temperature slightly less than the first step, if only prolonged heating is needed to degrade any remaining free radical initiator.

In a yet further embodiment microcapsules are obtained by steps comprising dispersing an oil soluble amine modified ethoxylated trimethylol propane triacrylate and an oil soluble diethylene glycol dimethacrylate along with free radical initiator and an organic acid into an internal phase oil. A first heating step is used comprising, heating for time and temperature sufficient to oligomerize the amine modified ethoxylated trimethylol propane triacrylate and a diethylene glycol dimethacrylate forming a pre-polymer; then adding to the internal phase oil a water phase comprising a dispersion of water, and a polyacrylic or polymethacrylic acid, and adding an emulsifying agent; and emulsifying the water phase into the oil phase. A second heating step then comprises, heating for a time and temperature sufficient to decompose at least a portion of the free radical initiator in the oil phase, thereby forming microcapsule wall material at the interface of the water and oil phases; and a third heating step comprising heating to at least 90° C. for at least three hours to polymerize the wall material.

In one embodiment the third heating step comprises heating to at least 90° C. for at least three hours.

In a further embodiment a second initiator is added in addition to the water phase and the initiator in the oil phase decomposes at a first temperature and the initiator in the water phase decomposes at a second temperature.

In a yet further embodiment, the initiators in the oil phase and the water phase can be the same or different.

In a further embodiment microcapsules are obtained by steps comprising: dispersing an oil soluble amine modified polyfunctional polyvinyl monomer or oligomer and an oil soluble bi- or polyfunctional vinyl monomer or oligomer along with a free radical initiator and an organic acid into an internal phase oil; a first heating step comprising heating for a time and temperature sufficient to decompose at least some portion of the free radical initiator and thereby oligomerize or further oligomerize the amine modified polyfunctional polyvinyl monomer or oligomer and oil soluble bi- or polyfunctional vinyl monomer or oligomer forming a pre-polymer. Added to the internal phase oil is a water phase comprising a dispersion in water of an emulsifier, and emulsifying the water phase into the oil phase forming droplets of the water phase dispersed in the oil phase. A second heating step comprising heating for a time and temperature sufficient to decompose the remaining portion of free radical initiator thereby forming microcapsule wall material from prepolymer at the interface of the water and oil phases. A third heating step comprises heating to a temperature equal to or greater than the second heating step temperature for a time sufficient to polymerize the wall material.

In one embodiment the oligomerization is accomplished by heating, in the first heating step, to at least 55° C. for at least one hour to form the prepolymer.

In a further embodiment the third heating step comprises heating to at least 90° C. for at least three hours. In a further embodiment, the initiator is added in addition to the water phase dispersion of anionic emulsifier, and the initiator in the oil phase decomposes at a first temperature and the initiator in the water phase decomposes at a second temperature. The initiators in the oil and water phases can be the same or different.

In a further embodiment microcapsules are obtained by steps comprising providing an internal phase oil and a water phase containing a free radical initiator in at least one of said phases, and dispersing an oil soluble amine modified polyfunctional polyvinyl monomer or oligomer and an oil soluble bi- or polyfunctional vinyl monomer or oligomer and an organic acid into the internal phase oil; then adding to the internal phase oil the water phase which further comprises a dispersion in water of an emulsifier, and emulsifying the water phase into the oil phase forming droplets of the water phase in the oil phase.

A first heating step comprises, heating for a time and temperature sufficient to decompose the free radical initiator in at least the oil or water phase, and sufficient to oligomerize or further oligomerize the amine modified polyfunctional polyvinyl monomer or oligomer and oil soluble bi- or polyfunctional vinyl monomer or oligomer forming a pre-polymer and thereby forming microcapsule wall material at the interface of the water and oil phases.

A second heating step comprises heating to a temperature equal to or greater than the first heating step temperature for a time sufficient to polymerize the wall material.

In one embodiment the second heating step comprises heating to at least 90° C. for at least three hours. Alternatively, initiator can be added to both the oil and water phases. Optionally, the initiator in the oil phase can decompose at a first temperature and the initiator in the water phase can decompose at a second temperature. The initiators in the oil and water phases can be the same or different.

The cationic or nonionic emulsifier comprises a water-soluble or water-dispersible material and optionally a water phase initiator, where the first composition initiator and the water phase initiator is an energy-activated initiator. The reaction product of the first composition and second composition results in the formation of a population of microcapsules having a microcapsule wall of low permeance to the core material and having a zeta potential of −5 millivolts or greater, the resulting microcapsules having strong adherence to anionic surfaces.

DETAILED DESCRIPTION OF THE INVENTION

Definitions

As used herein "consumer product" means baby care, personal care, fabric & home care, family care, feminine care, health care, snack and/or beverage products or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as foam substrates, films, and combinations thereof, bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations there of.

As used herein, the term "personal care composition" includes, unless otherwise indicated, any personal care composition that can be applied to the keratinaceous surfaces of the body including the skin and/or hair. The personal care compositions can be, for example, formulated as bars, liquids, emulsions, shampoos, gels, powders, sticks, hair conditioners (rinse off and leave in), hair tonics, pastes, hair colorants, sprays, mousses and/or other styling products, as well as shave prep products, and devices used for shaving.

As used herein, the term "fluid" includes liquid, gel, paste and gas product forms.

As used herein, the term "solid" means granular, powder, bar and tablet product forms.

As used herein, the term "situs" includes paper products, fabrics, garments, hard surfaces, hair and skin.

As used herein, the terms "particle", "benefit agent delivery particle", "capsule" and "microcapsule" are synonymous and microcapsules encompass perfume microcapsules.

As used herein, the articles including "a" and "an" when used in a claim, are understood to mean one or more of what is claimed or described.

As used herein, the terms "include", "includes" and "including" are meant to be non-limiting.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Process of Making Encapsulated Materials

The present invention teaches novel processes for microencapsulation involving water in oil, or oil in water emulsifications, and microcapsules obtained by such processes. In one aspect, the present invention teaches a low permeability microcapsule particle comprising a core material and a wall material at least partially surrounding, and preferably completely surrounding a core material.

In one aspect of the invention, a first composition may comprise an oil soluble or dispersible primary, secondary, or tertiary amine with a multifunctional acrylate or methacrylate monomer or oligomer and an oil soluble acid and an initiator.

A second composition is an emulsifier and comprises a water soluble or water dispersible polymer or copolymer, usually at least one water phase initiator and one or more of an alkali or alkali salt. By water phase initiator, it is meant that the initiator is soluble or dispersible in water.

The reaction of the first composition in the presence of the second composition results in the formation of a low permeability microcapsule wall.

The amines can include by way of illustration and not limitation amine modified vinyl monomers including amine modified acrylates or methacrylates such as mono or diacrylate amines, mono or dimethacrylate amines, amine modified polyetheracrylates and amine modified polyethermethacrylates, aminoalkyl acrylates or aminoalkyl methacrylate.

The amines can include primary, secondary or tertiary amines and can include tertiary butyl ammethylmethacrylate, diethylaminoethyl methacrylate, or dimethylaminoethyl methacrylate.

More particularly, the present invention in one embodiment is a process of obtaining microcapsules by dispersing an oil soluble amine modified polyfunctional polyvinyl monomer or oligomer and an oil soluble bi- or polyfunctional vinyl monomer or oligomer along with a free radical initiator, such as an azo or peroxy initiator, and an organic acid into an internal phase oil. This dispersion is heated for a time and temperature sufficient to oligomerize or further oligomerize the amine modified polyfunctional polyvinyl monomer and oil soluble bi- or polyfunctional vinyl monomer or oligomer to form a prepolymer. To this internal phase oil and prepolymer, a water phase is added comprising a dispersion in water of an emulsifier or an initiator. The water phase in one embodiment is emulsified into the oil phase (W/O). The dispersion is then heated for a time and temperature sufficient to decompose the free radical initiator, which can be placed in one or both of the oil and water phases. Microcapsule wall material is thereby formed at the interface of the water and oil phases. A third heating step is used to polymerize or harden the formed wall material and usefully to decompose remaining initiator. Decompose the free radical initiator means that the initiator is consumed and in the process generates free radicals for furthering propagation of polymerization reaction of the monomers and oligomers.

In forming the capsules of the invention, the emulsion is usually milled to a size of from about 2 microns to about 80 microns, from about 5 microns to about 50 microns, or even from about 10 microns to about 30 microns. Larger sizes for particular applications are also feasible.

Unlike conventional microencapsulation processes, the W/O and O/W processes taught herein employing an organic acid are believed to drive wall material from the oil phase to the oil water interface, though the application and invention should not be construed as limited to this proposed mechanism.

The invention teaches novel processes for microencapsulation using water in oil, or alternatively oil in water emulsifications. The capsules by the process of the invention enable a low permeability or controlled permeability capsule to be fashioned. Permeability can be controlled through wall material selection, through control of degree of cross-linking, by controlling temperature of cross-linking, by controlling length of time of cross-linking, or with UV initiated systems by controlling intensity of UV light and duration.

In an alternative embodiment, the present invention is a process of obtaining microcapsules by dispersing an oil soluble amine modified polyfunctional polyvinyl monomer or oligomer and an oil soluble bi- or polyfunctional vinyl monomer or oligomer along with a free radical initiator, such as a peroxy or azo initiator, and an organic acid into an internal phase oil. This dispersion is heated for a time and temperature sufficient to oligomerize or further oligomerize the amine modified polyfunctional polyvinyl monomer and oil soluble bi- or polyfunctional vinyl monomer to form a prepolymer. To this internal phase oil and prepolymer, a water phase is added in excess comprising a dispersion in water of an emulsifier and optionally, a free radical initiator. The oil phase in this embodiment is emulsified into the water phase (O/W). The dispersion is then heated for a time and temperature sufficient to decompose the free radicals, positioned in one or both of the oil and water phases. Microcapsule wall material is thereby formed at the interface of the water and oil phases.

Preferred amine modified polyfunctional polyvinyl monomers include amine modified ethoxylated trimethylol propane triacrylate, ethoxylated aliphatic, acrylated amines, such as diacrylate amines, triacrylate amines dimethacrylate amines, amine modified polyetheracrylates and amine modified polyethermethacrylates.

Preferred bi- or polyfunctional vinyl monomers include by way of illustration and not limitation, allyl methacrylate; triethylene glycol dimethacrylate; ethylene glycol dimethacrylate, diethylene glycol dimethacrylate, aliphatic or aromatic urethane diacrylates, difunctional urethane acrylates, ethoxylated aliphatic difunctional urethane methacrylates, aliphatic or aromatic urethane dimethacrylates, epoxy acrylates, epoxymethacrylates; tetraethylene glycol dimethacrylate; polyethylene glycol dimethacrylate; 1,3 butylene glycol diacrylate; 1,4-butanediol dimethacrylate; 1,4-butaneidiol diacrylate; diethylene glycol diacrylate; 1,6 hexanediol diacrylate; 1,6 hexanediol dimethacrylate; neopentyl glycol diacrylate; polyethylene glycol diacrylate; tetraethylene glycol diacrylate; triethylene glycol diacrylate; 1,3 butylene glycol dimethacrylate; tripropylene glycol diacrylate; ethoxylated bisphenol diacrylate; ethoxylated bisphenol dimethylacrylate; dipropylene glycol diacrylate; alkoxylated hexanediol diacrylate; alkoxylated cyclohexane dimethanol diacrylate; propoxylated neopentyl glycol diacrylate, trimethylolpropane trimethacrylate; trimethylolpropane triacrylate, pentaerythritol triacrylate, ethoxylated trimethylolpropane triacrylate, propoxylated trimethylolpropane triacrylate, propoxylated glyceryl triacrylate, ditrimethylolpropane tetraacrylate, dipentaerythritol pentaacrylate, ethoxylated pentaerythritol tetraacrylate.

The organic acid can be selected from various acids such as carboxy acids, with monoalkyl maleates such as monomethyl, monoethyl or monobutyl maleate being preferred, with monobutyl maleate being most preferred. Other organic acids that can be usefully employed in the invention include, organic sulfonic acids such as alkyl benzene sulfonic acid, more particularly linear alkyl benzene sulfonic acid, tridecylbenzene sulfonic acid, more particularly linear trialkyl benzene sulfonic acid such as linear tridecyl benzene sulfonic acid, alkyldiphenyloxide sulfonic acid, preferably dodecyl diphenyl oxidedisulfonic acid, more particularly branched C12 diphenyl oxide disulfonic acid, alkylbenzene sulfonic acid, more particularly, dodecyl benzene sulfonic acid, dialkyl naphthalene disulfonic acid, more particularly dinonylnaphthalene disulfonic acid, 4-hydrozino benzene sulfonic acid acrylic acid, methacrylic acid, and the like. Desirably the organic acid is selected to be dispersible in the oil phase and sparingly soluble in the water phase.

Suitable emulsifiers for use herein are anionic, cationic, or nonionic emulsifiers. In certain circumstances amphoteric emulsifiers and zwitterionic emulsifiers can find applicability.

In one embodiment, the emulsifier is cationic. the cationic or nonionic emulsifier comprises a water soluble or water dispersible material and optionally a water phase initiator. The first composition initiator and the water phase initiator is an energy-activated initiator. The reaction product of the first composition and second composition results in the formation of a population of microcapsules having a microcapsule wall of low permeance to the core material and having a zeta potential of −5 millivolts or greater. The resulting microcapsules have adherence to anionic surfaces.

The emulsifier generally has a molecular weight greater than about 100. Cationic emulsifiers include amine polymers with primary, secondary or tertiary functionality. Preferably the cationic emulsifier is selected from palmitamidopropyltrimonium chloride (Varisoft PATC™, available from Degussa Evonik, Essen, Germany), distearyl dimonium chloride, cetyltrimethylammonium chloride, quaternary ammonium compounds, fatty amines, aliphatic ammonium halides, alkyldimethylbenzylammonium halides, alkyldimethylethylammonium halides, polyethyleneimine, poly(2-dimethylamino)ethyl methacrylate) methyl chloride quaternary salt, poly(1-vinylpyrrolidone-co-2-dimethylaminoethyl methacrylate), poly(acrylamide-co-diallyldimethylammonium chloride), poly(allylamine), poly[bis(2-chloroethyl)ether-alt-1,3-bis[3-(dimethylamino)propyl]urea] quaternized, and poly(dimethylamine-co-epichlorohydrin-co-ethylenediamine), and condensation products of aliphatic amines with alkylene oxide.

The cationic emulsifiers include quaternary ammonium compounds with a long-chain aliphatic radical, e.g. distearyldiammonium chloride, and fatty amines. Among the cationic emulsifiers which may be mentioned are alkyldimethylbenzylammonium halides, alkyldimethylethylammonium halides, etc. Preferred emulsifiers are those which significantly reduce the interfacial tension between the aqueous phase and dispersed phase, and thereby reduce the tendency for droplet coalescence.

In an alternative embodiment the emulsifier is nonionic. Preferably the nonionic emulsifier is selected from polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, polyvinyl acetate, or copolymers of polyvinyl alcohol polyvinyl acetate, polyacrylamide, poly(N-isopropylacrylamide), poly(2-hydroxypropyl methacrylate), poly(2-ethyl-2-oxazoline), poly(2-isopropenyl-2-oxazoline-co-methyl methacrylate), poly(methyl vinyl ether), and polyvinyl alcohol-co-ethylene). Especially useful polyvinylalcohols include polyvinyl alcohols of molecular weight 13000 to 186000 daltons, preferably from 13000 to about 23000 daltons, or even from 146000 to 186000 daltons. The polyvinyl alcohol can be partially or fully hydrolyzed.

Polyvinyl alcohol partially hydrolyzed in the range of 85 to 95% hydrolyzed is preferred. Partially hydrolyzed polyvinylalcohol at 88% hydrolysis or less was useful, with about 88% hydrolysis being more preferred.

An exemplary zwitterionic emulsifier is cocoamidopropyl betaine.

The amount of emulsifier is anywhere from about 0.1 to about 40 percent by weight of all constituents, more preferably from 0.5 to about 10 percent, most preferably 0.5 to 5 percent by weight. Typically emulsifier is employed at 0.2 to about 10% by weight based on percentage of the total formulation.

Excluding solvent, the primary, secondary or tertiary amine acrylate or methacrylate and the multi-functional acrylate or methacrylate monomers are used in a relative ratio by weight of from about 0.1:99.9 to about 10:90 preferably from about 0.5:99.5 to about 5:95, and most preferably 1:99 to about 3:97. The ratio of the amine to the multifunctional acrylate is in the range of from 0.1:99.9 to 10:90. Therefore the amine can be in the range of from 0.1 to 10% by weight as compared to the multifunctional acrylate, or even from 0.5 to 5%, or most preferably 1 to 3% by weight.

After solvent, the amine modified polyfunctional polyvinyl monomer and the oil soluble bi- or poly functional vinyl monomers are the larger constituents by weight used in a relative ratio of from about 0.5:1 to about 1:3 preferably from about 1:1 to about 1:2.

The average molecular weight of the monomers initially is in the hundreds of daltons. For the oligomer molecular weights are in the thousands to tens of thousands of daltons. Prepolymers accordingly are higher molecular weight still. Prepolymers are an intermediate block of oligomers and monomers eventually forming a polymer. The monomer or oligomers should be selected to be soluble or dispersible in the oil phase.

For example, assuming a system of about 600 grams with solvent, the largest constituents are typically solvent, 10 to 70 weight percent, preferably 35 to 65 weight percent oil phase solvent and oil; 10 to 70 weight percent, preferably 35 to 65 weight percent water; 0.1 to 20 weight percent, usually 0.5 to 8 weight percent preferably 2 to 6 weight percent, bi- or polyfunctional vinyl monomer or oligomer; oil to 20 weight percent, usually 0.5 to 8 weight percent, preferably 2 to about 4 weight percent, amine modified amine modified polyfunctional monomer or oligomer. Initiator is 10% or less, usually about 1% or less, preferably 0.5% by weight or less and more preferably 0.1% or less.

As will be evident, the amount of the respective solvent or oil can be increased or decreased as needed for rheology and depending on whether an W/O or O/W system is desired.

Preferred free radical initiators include peroxy initiators, azo initiators, peroxides, and compounds such as 2,2'-azobis-methylbutyronitrile, dibenzoyl peroxide. More particularly, and without limitation the free radical initiator can be selected from the group of initiators comprising an azo or peroxy initiator, such as peroxide, dialkyl peroxide, alkyl peroxide, peroxyester, peroxycarbonate, peroxyketone and peroxydicarbonate, 2,2'-azobis(isobutylnitrile), 2,2'-azobis(2,4-dimethylpentanenitrile), 2,2'-azobis(2,4-dimethylvaleronitrile), 2,2'-azobis(2-methylpropanenitrile), 2,2'-azobis(methylbutyronitrile), 1,1'-azobis(cyclohexanecarbonitrile), 1,1'-azobis(cyanocyclohexane), benzoyl peroxide, decanoyl peroxide; lauroyl peroxide; benzoyl peroxide, di(n-propyl) peroxydicarbonate, di(sec-butyl)peroxydicarbonate, di(2-ethylhexyl)peroxydicarbonate, 1,1-dimethyl-3-hydroxybutyl peroxyneodecanoate, α-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di(2-ethylhexanoyl peroxy)hexane, t-amyl peroxy-2-ethyl-hexanoate, t-butyl peroxy-2-ethylhexanoate, t-butyl peroxyacetate, di-t-amyl peroxyacetate, t-butyl peroxide, di-t-amyl peroxide, 2,5-dimethyl-2,5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate, ethyl 3,3-di-(t-amylperoxy)-butyrate, and the like. Blends of initiators can also be employed. Initiators are available commercially, such as Vazo initiators, which typically indicate a decomposition temperature for the initiator. Preferably the initiator is selected to have a decomposition point of about 50° C. or higher. Usefully multiple initiators are employed, either as a blend in the oil phase, or in either of the oil or water phases. Preferably initiators are selected to stagger the decomposition temperatures at the various steps, pre-polymerization, wall formation and hardening or polymerizing of the capsule wall material. For example, a first initiator in the oil phase can decompose at 55° C., to promote prepolymer formation, a second can decompose at 60° C. to aid forming the wall material. Optionally a third initiator can decompose at 65° C. to facilitate polymerization of the capsule wall material. The amount of each initiator can be typically as low as 0.1 weight percent or as high as 10 weight percent.

Internal phase oils, or oil phase, or oil solvent or "nonsolvent for the water phase," used interchangeably for purposes hereof can be selected from solvents and the solvents can include by way of illustration and not limitation, ethyldiphenylmethane, butyl biphenyl ethane, benzylxylene, alkyl biphenyls such as propylbiphenyl and butylbiphenyl, dialkyl phthalates e.g. dibutyl phthalate, dioctylphthalate, dinonyl phthalate and ditridecylphthalate; 2,2,4-trimethyl-1,3-pentanediol diisobutyrate, alkyl benzenes such as dodecyl benzene; alkyl or aralkyl benzoates such as benzyl benzoate; diaryl ethers, di(aralkyl)ethers and aryl aralkyl ethers, ethers such as diphenyl ether, dibenzyl ether and phenyl benzyl ether, liquid higher alkyl ketones (having at least 9 carbon atoms), alkyl or aralky benzoates, e.g., benzyl benzoate, alkylated naphthalenes such as dipropylnaphthalene, partially hydrogenated terphenyls; high-boiling straight or branched chain hydrocarbons, alkaryl hydrocarbons such as toluene, vegetable oils such as canola oil, soybean oil, corn oil, sunflower oil, or cottonseed oil, methyl esters of fatty acids derived from transesterification of canola oil, soybean oil, cottonseed oil, corn oil, sunflower oil, pine oil, lemon oil, olive oil, or methyl ester of oleic acid, vegetable oils, esters of vegetable oils, e.g. soybean methyl ester, straight chain saturated paraffinic aliphatic hydrocarbons of from 10 to 13 carbons. Mixtures of the above can also be employed. Common diluents such as straight chain hydrocarbons can also be blended with the solvents, or blend of solvents. The solvent is selected on the basis of hydrophobicity and ability to disperse or solvate the amine modified polyfunctional polyvinyl monomer and the bi- or polyfunctional vinyl monomer or oligomer. "Internal phase oil" is herein to described as a type of oil material commonly able to be used as the oil in conventional microencapsulation. In conventional microencapsulation, the internal phase oil ends up as the core or internal contents of the microcapsule. In the processes of the invention which involve water in oil (W/O) emulsifications, the internal phase oil is used in excess and the water then becomes the capsule core. The term in this context describes a type of oil, but for clarity shall be understood as not necessarily forming the capsule core when water in oil emulsifications are being done. Internal phase oil is describing a nonsolvent for the water phase in such context.

When the internal phase is a perfume oil, the capsule core may comprise a partitioning modifier selected from the group consisting of oil soluble materials that have a ClogP greater than from about 4, or from about 5, or from about 7, or even from about 11 and/or materials that also have a density higher than 1 gram per cubic centimeter. In one aspect, suitable partitioning modifier may comprise a material selected from the group consisting of materials include Mono, di- and tri-esters of $C_4$-$C_{24}$ fatty acids and glycerine; fatty acid esters of polyglycerol oligomers; polyalphaolefins; silicone oil; crosslinked silicones comprising polyether substituted structural units and acrylate crosslinks; polyglycerol ether silicone crosspolymers; alkyl substituted cellulose; hydroxypropyl cellulose; fatty esters of acrylic or methacrylic acid that have side chain crystallizing groups; copolymers of ethylene, including ethylene and vinyl acetate, ethylene and vinyl alcohol, ethylene/acrylic elastomers; acetyl caryophyllene, hexarose, butyl oleate, hydrogenated castor oil, sucrose benzoate, dodecanoic acid, palmitic acid, stearic acid, tetradecanol, hexadecanol, 1-octanediol, isopropyl myristate, castor oil, mineral oil, isoparaffin, capryllic triglyceride, soybean oil, vegetable oil, brominated vegetable oil, bromoheptane, sucrose octaacetate, geranyl palmitate, acetylcaryophyllene, sucrose benzoate, butyl oleate, silicones, polydimethylsiloxane, vitamin E, decamethylcyclopentasiloxane, dodecamethylcyclohxasiloxane, sucrose soyate, sucrose stearate, sucrose soyanate, lauryl alcohol, 1-tetradecanol, 1-hexadecanol, cetyl alcohol, 1-octadecanol, 1-docosanol, 2-octyl-1-dodecanol, perfume oils, in one aspect perfume oils having a ClogP>5, in one aspect said perfume oils may be selected from the group consisting of: Octadecanoic acid, octadecyl ester; Tetracosane, 2,6,10,15,19,23-hexamethyl-; Octadecanoic acid, diester dissolved in 1,2,3-propanetriol; Isotridecane, 1,1'-[(3,7-dimethyl-6-octenylidene)bis(oxy)]bis-; Tetradecanoic acid, octadecyl ester; 2,6,10,14,18,22-Tetracosahexaene, 2,6,10,15,19,23-hexamethyl-, (all-E)-; Tricosane; Docosane; Hexadecanoic acid, dodecyl ester; 1,2-Benzenedicarboxylic acid, didodecyl ester; Decanoic acid, 1,2,3-propanetriyl ester; 1-Undecene, 11,11-bis[(3,7-dimethyl-6-octenyl)oxy]-; Heneicosane; Benzene, [2-[bis[(3,7-dimethyl-2,6-octadienyl)oxy]methyl]-1-; 1-Undecene, 11,11-bis[(3,7-dimethyl-2,6-octadienyl)oxy]-; Benzene, [2-[bis[(1-ethenyl-1,5-dimethyl-4-hexenyl)oxy]methyl]-1-; Dodecanoic acid, tetradecyl ester; 2H-1-Benzopyran-6-ol, 3,4-dihydro-2,5,7,8-tetramethyl-2-(4,8,12-trimethyltridecyl)-, [2R-[2R*(4R*,8R*)]]-; Octanoic acid, octadecyl ester; Eicosane; 2H-1-Benzopyran-6-ol, 3,4-dihydro-2,5,8-trimethyl-2-(4,8,12-trimethyltridecyl)-, [2R*(4R*,8R*)]-; 2-Naphthalenol, 1-[6-(2,2-dimethyl-6-methylenecyclohexyl)-4-methyl-3-hexenyl]decahydro-2,5,5,8a-tetramethyl-, [1R-[1.alpha.[E(S*)],2.beta.,4a.beta.,8a.alpha.]]-; 2H-1-Benzopyran-6-ol, 3,4-dihydro-2,7,8-trimethyl-2-(4,8,12-trimethyltridecyl)-, [2R-[2R*(4R*,8R*)]]-; Heptanoic acid, octadecyl ester; Nonadecane; 2,4,6,8,10,12,14,16-Heptadecaoctaenal, 2,6,11,15-tetramethyl-17-(2,6,6-trimethyl-1-cyclohexen-1-yl)-, (2E,4E,6E,8E,10E,12E,14E,16E)-; 2H-1-Benzopyran-6-ol, 3,4-dihydro-2,8-dimethyl-2-(4,8,12-trimethyltridecyl)-, [2R-[2R*(4R*,8R*)]]-; Hexadecanoic acid, 2-ethylhexyl ester; 1,2-Benzenedicarboxylic acid, didecyl ester; Octadecane; Benzoic acid, 2-[[2-(phenylmethylene)octylidene]amino]-,1-ethenyl-1,5-dimethyl-4-hexenyl ester; Octadecanoic acid, 3-methylbutyl ester; Decanoic acid, ester with 1,2,3-propanetriol octanoate; Heptadecane; 1-Hexadecene, 7,11,15-trimethyl-3-methylene-; Dodecanoic acid, decyl ester; Octadecanoic acid, butyl ester; Decanedioic acid, bis(2-ethylhexyl) ester; Benzene, [2,2-bis[(3,7-dimethyl-6-octenyl)oxy]ethyl]-; Benzene, [2,2-bis[(3,7-dimethyl-2,6-octadienyl)oxy]ethyl]-; 9-Octadecenoic acid (Z)—, butyl ester; Octanoic acid, 1,2,3-propanetriyl ester; Hexadecane; Cyclohexene, 4-(5-methyl-1-methylene-4-hexenyl)-1-(4-methyl-3-pentenyl)-; 2-Hexadecen-1-ol, 3,7,11,15-tetramethyl-, acetate, [R—[R*,R*-(E)]]-; Hexadecanoic acid, butyl ester; Octadecanoic acid, ethyl ester; 1-Dodecanol, 2-octyl-; Pentadecane; Tetradecanoic acid, hexyl ester; Decanoic acid, decyl ester; Acetic acid, octadecyl ester; Hexadecanoic acid, 2-methylpropyl ester; 9-Octadecenoic acid (Z)—, ethyl ester; Heptadecanoic acid, ethyl ester; Octadecanoic acid, methyl ester; Tetradecane; Tetradecanoic acid, 3-methylbutyl ester; 2-Hexadecen-1-ol, 3,7,11,15-tetramethyl-, [R—[R*,R*-(E)]]-; 2-Hexadecen-1-ol, 3,7,11,15-tetramethyl-; Hexadecanoic acid, 1-methylethyl ester; 1H-Indole, 1,1'-(3,7-dimethyl-6-octenylidene)bis-; Octadecanoic acid; Cyclopentasiloxane, decamethyl-; Benzoic acid, 2-[[2-(phenylmethylene)octylidene]amino]-, 3-methylbutyl ester; 9,12-Octadecadienoic acid (Z,Z)—, ethyl ester; 1-Octadecanol; Hexanedioic acid, dioctyl ester; 9-Octadecenoic acid (Z)—, methyl ester; Octadecanoic acid, 2-hydroxypropyl ester; Tetradecanoic acid, butyl ester; Dodecanoic acid, hexyl ester; 9,12,15-Octadecatrienoic acid, ethyl ester, (Z,Z,Z)—; Hexadecanoic acid, ethyl ester; 1-Hexadecanol, acetate; 9-Octadecenoic acid (Z)—; Hexanedioic acid, bis(2-ethylhexyl) ester; 1,8,11,14-Heptadecatetraene; 1,8,11,14-Heptadecatetraene; 1,8,11,14-Heptadecatetraene; 9-Octadecen-1-ol, (Z)—; Tetradecanoic acid, 2-methylpropyl ester; Nonanoic acid, 1-methyl-1,2-ethanediyl ester; Tridecane; Naphthalene, decahydro-1,6-dimethyl-4-(1-methylethyl)-, [1S-(1.alpha.,4.alpha.,4a.alpha.,6.alpha.,8a.beta.)]-, didehydro deriv.; 1-Hexadecyn-3-ol, 3,7,11,15-tetramethyl-; 9,12-Octadecadienoic acid (Z,Z)—, methyl ester; 1-Heptadecanol; 6,10,14-Hexadecatrien-3-ol, 3,7,11,15-tetramethyl-; Benzoic acid, 2-[[[4-(4-methyl-3-pentenyl)-3-cyclohexen-1-yl]methylene]amino]-, methyl ester; 9,12-Octadecadienoic acid (Z,Z)—; 2-Nonene, 1,1'-oxybis-; Santalol, benzeneacetate; 10-Undecenoic acid, heptyl ester; 9,12,15-Octadecatrienoic acid, methyl ester, (Z,Z,Z)—; Octadecanoic acid, monoester with 1,2,3-propanetriol; Dodecanoic acid, pentyl ester; Octanoic acid, nonyl ester; Pentadecanoic acid, ethyl ester; Hexadecanoic acid, methyl ester; Dodecanoic acid, 4-methylphenyl ester; Dodecanoic acid, 3-methylbutyl ester; Tetradecanoic acid, 1-methylethyl ester; Hexadecanoic acid; 1-Phenanthrenecarboxylic acid, tetradecahydro-1,4a-dimethyl-7-(1-methylethyl)-, methyl ester, [1R-(1.alpha.,4a.beta.,4b.alpha.,7.beta.,8a.beta.,10a.alpha.)]-; 1-Hexadecanol; Dodecane; 2-Pentadecanone, 6,10,14-trimethyl-; 9-Heptadecanone; 1-Phenanthrenemethanol, 1,2,3,4,4a,4b,5,6,10,10a-decahydro-1,4a-dimethyl-7-(1-methylethyl)-, acetate, [1R-(1.alpha.,4a.beta.,4b.alpha.,10a.alpha.)]-; Isohexadecanol; Dodecanoic acid, 2-methylpropyl ester; Hexadecanenitrile; Octadecanoic acid, 2,3-dihydroxypropyl ester; Isododecane; 1-Phenanthrenemethanol, tetradecahydro-1,4a-dimethyl-7-(1-methylethyl)-; Octanoic acid, 3,7-dimethyl-2,6-octadienyl ester, (E)-; Dodecanoic acid, butyl ester; Tetradecanoic acid, ethyl ester; Butanoic acid, dodecyl ester; Benzoic acid, 2-amino-, decyl ester; Oxacycloheptadecan-2-one; Propanoic acid, 2-methyl-, dodecyl ester; 1H-Indene, octahydro-1,1,2,3,3-pentamethyl-; 1-Phenanthrenecarboxylic acid, 1,2,3,4,4a,4b,5,6,7,8,10,10a-dodecahydro-1,4a-dimethyl-7-(1-methylethyl)-, methyl ester; 9-Octadecenoic acid (Z)—, ester with 1,2,3-propanetriol; 9,12,15-Octadecatrienoic acid, (Z,Z,Z)—; 1,4,8-Cycloundecatriene, 2,6,6,9-tetramethyl-, (E,E,E)-; 1-Phenanthrenemethanol, dodecahydro-1,4a-dimethyl-7-(1-methylethyl)-; Benzoic acid, 3,4,5-trihydroxy-, dodecyl ester; 1H-Indole-1-heptanol, .eta.-1H-indol-1-yl-.alpha.,.alpha.,.epsilon.-; Cyclododecane; 9-Hexadecenoic acid, (Z)—; Benzoic acid, 2-[[2-(phenylmethylene)heptylidene]amino]-, methyl; 9-Octadecenoic acid (Z)—, 2,3-dihydroxypropyl ester; 2-Naphthalenecarboxaldehyde, 5,6,7,8-tetrahydro-3,5,5,6,7,8,8-heptamethyl-, trans-; Octanoic acid, 1-ethenyl-1,5-dimethyl-4-hexenyl ester; 2-Hexadecanone and mixtures thereof; and/or a density modifier selected from the group consisting of Brominated vegetable oil; sucrose octaacetate; bromoheptane; titanium dioxide; zinc oxides; iron oxides; cobalt oxides; nickel oxides; silver oxides; copper oxides; zirconium oxides; silica; silver; zinc; iron; cobalt; nickel; copper; epoxidized soybean oil polyols; 1 h-indene, 2,3-dihydro-1,1,3,3,5-pentamethyl-4,6-dinitro-; benzene, (2-bromoethenyl)-; benzeneacetic acid, 2-methoxy-4-(1-propenyl)phenyl ester; ethanone, 1-(2,5-dimethyl-3-thienyl)-; oxiranecarboxylic acid, 3-(4-methoxyphenyl)-, ethyl ester; benzoic acid, 2-[(1-hydroxy-3-phenylbutyl)amino]-, methyl ester; 1,3-benzodioxole-5-carboxylic acid, ethyl ester; 1,3-benzodioxole, 5-(2-propenyl)-; benzoic acid, 4-methoxy-; benzenemethanol, .alpha.-(trichloromethyl)-, acetate; phenol, 2-methoxy-4-(2-propenyl)-, formate; phenol, 2-methoxy-4-(2-propenyl)-, benzoate; 2-propen-1-ol, 3-phenyl-, benzoate; benzeneacetic acid, 3-methylphenyl ester; benzene, 1-(1,1-dimethylethyl)-3,4,5-trimethyl-2,6-dinitro-; benzeneacetic acid, 4-methylphenyl ester; benzeneacetic acid, phenylmethyl ester; benzeneacetic acid, (4-methoxyphenyl)methyl ester; 2-propenoic acid, 3-phenyl-, phenylmethyl ester; 2-propenoic acid, 3-phenyl-, 2-phenylethyl ester; benzeneacetic acid, 2-methoxy-4-(2-propenyl)phenyl ester; phenol, 2-(methylthio)-; benzoic acid, 2-[[3-(1,3-benzodioxol-5-yl)-2-methylpropylidene]amino]-, methyl ester; benzoic acid, 2-[[3-(4-methoxyphenyl)-2-methylpropylidene]amino]-, methyl ester; benzoic acid, 3,5-dimethoxy-; benzoic acid, 2-hydroxy-, phenyl ester; benzoic acid, 2-hydroxy-, phenylmethyl ester; benzoic acid, 2-hydroxy-, ethyl ester; benzoic acid, 2-hydroxy-, methyl ester; benzoic acid, 2-amino-, methyl ester; ethanone, 2-hydroxy-1,2-diphenyl-; benzoic acid, 4-hydroxy-, ethyl ester; benzoic acid, phenylmethyl ester; 1,3-benzodioxole, 5-(1-propenyl)-; benzothiazole, 2-methyl-; 5h-dibenzo[a,d]cyclohepten-5-one, 10,11-dihydro-; oxiranecarboxylic acid, 3-phenyl-, ethyl ester; benzoic acid, 4-methoxy-, methyl ester; 2-propenoic acid, 3-phenyl-, 3-phenyl-2-propenyl ester; tricyclo[3.3.1.13,7]decan-2-ol, 4-methyl-8-methylene-; tricyclo[3.3.1.13,7]decan-2-ol, 4-methyl-8-methylene-, acetate; methanone, bis(2,4-dihydroxyphenyl)-; methanone, (2-hydroxy-4-methoxyphenyl) phenyl-; dibenzofuran; benzoic acid, 2-amino-, 2-phenylethyl ester; ethanone, 1-(naphthalenyl)-; furan, 2,2'-[thiobis(methylene)]bis-; 1,2,3-propanetriol, tripropanoate; 2-propenoic acid, 3-phenyl-, (e)-; phenol, 4-ethyl-2,6-dimethoxy-; disulfide, methyl phenyl; benzoic acid, 2-[[(4-methoxyphenyl)methylene]amino]-, methyl ester; 2-propenoic acid, 3-(2-methoxyphenyl)-, (z)-; 8-quinolinol; disulfide, bis(phenylmethyl); 1,2-propanediol, dibenzoate; benzene, 1-bromo-4-ethenyl-; trisulfide, di-2-propenyl; phenol, 2,6-dimethoxy-4-(1-propenyl)-, (e)-; benzene, (2-isothiocyanatoethyl)-; benzoic acid, 2-hydroxy-5-methyl-, methyl ester; 1,2,4-trithiolane, 3,5-dimethyl-; propanoic acid, 2-(methyldithio)-, ethyl ester; benzoic acid, 2-hydroxy-, cyclohexyl ester; benzoic acid, 2-[(1-oxopropyl)amino]-, methyl ester; ethanethioic acid, s-(4,5-dihydro-2-methyl-3-furanyl) ester; benzoic acid, 2-(acetylamino)-, methyl ester; 1,3,5-trithiane, 2,4,6-trimethyl-; benzoic acid, 2-amino-, propyl ester; butanoic acid, 1-naphthalenyl ester; benzoic acid, 2,4-dihydroxy-3-methyl-, methyl ester; trisulfide, methyl 2-propenyl; 2-furanmethanol, benzoate; benzoic acid, 2-hydroxy-5-methyl-, ethyl ester; benzene, (2,2-dichloro-1-methylcyclopropyl)-; 2-thiophenecarboxaldehyde, 5-ethyl-; benzoic acid, [(phenylmethylene)amino]-, methyl ester; spiro[1,3-dithiolo[4,5-b]furan-2,3'(2'h)-furan], hexahydro-2',3a-dimethyl-; 1,3-benzodioxole, 5-(diethoxymethyl)-; cyclododeca[c]furan, 1,3,3a,4,5,6,7,8,9,10,11,13a-dodecahydro-; benzeneacetic acid, 2-methoxyphenyl ester; 2-benzofurancarboxaldehyde; 1,2,4-trithiane, 3-methyl-; furan, 2,2'-[dithiobis(methylene)]bis-; 1,6-heptadiene-3,5-dione, 1,7-bis(4-hydroxy-3-methoxyphenyl)-, (e,e)-; benzoic acid, 2,4-dihydroxy-3,6-dimethyl-, methyl ester; benzoic acid, 2-hydroxy-4-methoxy-, methyl ester; propanoic acid, 2-methyl-, 1,3-benzodioxol-5-ylmethyl ester; 1,2,4-trithiolane, 3,5-diethyl-; 1,2,4-trithiolane, 3,5-bis(1-methylethyl)-; furan, 2-[(methyldithio)methyl]-; tetrasulfide, dimethyl; benzeneacetaldehyde, .alpha.-(2-furanylmethylene)-; benzoic acid, 3-methoxy-; benzenecarbothioic acid, s-methyl ester; benzoic acid, 2-methoxy-, methyl ester; benzoic acid, 2-hydroxy-, 4-methylphenyl ester; benzoic acid, 2-hydroxy-, propyl ester; 2-propenoic acid, 3-(2-methoxyphenyl)-; 2-propenoic acid, 3-(3-methoxyphenyl)-; benzoic acid, 2-hydroxy-4-methoxy-6-methyl-, ethyl ester; benzaldehyde, 2-hydroxy-5-methyl-; 1,2,3-propanetriol, tribenzoate; benzoic acid, 4-methylphenyl ester; 2-furancarboxylic acid, propyl ester; benzoic acid, 2-hydroxy-, 2-methylphenyl ester; benzoic acid, 4-hydroxy-3-methoxy-, ethyl ester; 2-propenoic acid, 3-phenyl-; benzene, 1,3-dibromo-2-methoxy-4-methyl-5-nitro-; benzene, (isothiocyanatomethyl)-; 2-propenoic acid, 3-(2-furanyl)-, ethyl ester; benzenemethanethiol, 4-methoxy-; 2-thiophenemethanethiol; benzene, 1,1'-[(2-phenylethylidene)bis(oxymethylene)]bis-; phenol, 2,6-dimethoxy-4-(2-propenyl)-; benzoic acid, 2-[(2-phenylethylidene)amino]-, methyl ester; benzenepropanoic acid, .beta.-oxo-, 4-methylphenyl ester; 1 h-indole-3-heptanol, .eta.-1h-indol-3-yl-.alpha.,.alpha.,.epsilon.-trimethyl-; benzoic acid, 2-hydroxy-, 3-methyl-2-butenyl ester; 1,3-benzodioxole-5-propanol, .alpha.-methyl-, acetate; thiophene, 2,2'-dithiobis-; benzoic acid, 2-hydroxy-; benzaldehyde, 2-hydroxy-4-methyl-; disulfide, methyl phenylmethyl; 2-furancarboxylic acid, 2-phenylethyl ester; benzenethiol, 2-methoxy-; benzoic acid, 2-[[(4-hydroxy-3-methoxyphenyl)methylene]amino]-, methyl ester; ethanol, 2-(4-methylphenoxy)-1-(2-phenylethoxy)-; benzeneacetic acid, 3-phenyl-2-propenyl ester; benzoic acid, 2-amino-, 2-propenyl ester; bicyclo[3.2.1]octan-8-one, 1,5-dimethyl-, oxime; 2-thiophenethiol; phenol, 2-methoxy-4-(1-propenyl)-, formate; benzoic acid, 2-amino-, cyclohexyl ester; phenol, 4-ethenyl-2-methoxy-; benzoic acid, 2-hydroxy-, 2-(1-methylethoxy)ethyl ester; ethanone, 1-[4-(1,1-dimethylethyl)-2,6-dimethyl-3,5-dinitrophenyl]-; benzene, 1-(1,1-dimethylethyl)-3,5-dimethyl-2,4,6-trinitro-; 2-propenoic acid, 3-(4-methoxyphenyl)-; benzene, 1-(1,1-dimethylethyl)-2-methoxy-4-methyl-3,5-dinitro-; 1,2-benzenedicarboxylic acid, diethyl ester; ethanone, 1-(3,4-dihydro-2h-pyrrol-5-yl)-; benzoic acid, 2-(methylamino)-, methyl ester; 2h-1-benzopyran-2-one, 7-ethoxy-4-methyl-; benzoic acid, 2-hydroxy-, 2-phenylethyl ester; benzoic acid, 2-amino-, ethyl ester; 2-propen-1-ol, 3-phenyl-, 2-aminobenzoate; phenol, 4-chloro-3,5-dimethyl-; disulfide, diphenyl; 1-naphthalenol; [1,1'-biphenyl]-2-ol; benzenemethanol, .alpha.-phenyl-; 2-naphthalenethiol; ethanone, 1-(2-naphthalenyl)-; phenol, 2-methoxy-4-(1-propenyl)-, acetate; 2-naphthalenol, benzoate; benzoic acid, phenyl ester; pyridine, 2-[3-(2-chlorophenyl)propyl]-; benzoic acid, 4-hydroxy-, propyl ester; ethanone, 1-(1-naphthalenyl)-; propanoic acid, 3-[(2-furanylmethyl)thio]-, ethyl ester; 2-propen-1-one, 1,3-diphenyl-; 3-pyridinecarboxylic acid, phenylmethyl ester; benzoic acid, 2-phenylethyl ester; piperidine, 1-[5-(1,3-benzodioxol-5-yl)-1-oxo-2,4-pentadienyl]-,(e,e)-; benzothiazole and mixtures thereof.

The microencapsulation process in certain of the embodiments is believed to rely on the organic acid for formation of a changed species that drives the wall material to the oil water interface. Charged species may also be formed through the use of an oil-soluble organic acidic acrylate or methacrylate with an inorganic water-soluble base, or an oil-soluble organic amine acrylate or methacrylate with an inorganic water-soluble base. Oil-soluble acids or bases may also be utilized, as appropriate, for neutralization of the acrylate or methacrylate acids or bases.

The size of the capsules can be controlled by adjusting the speed of agitation. Smaller size dispersions are achieved through faster agitation resulting in smaller capsules.

Emulsifying agents or protective colloids can be conveniently employed to facilitate dispersion. Such materials for example include carboxylated or partially hydrolyzed polyvinyl alcohol, methyl cellulose, and various latex materials, stearates, lecithins, and various surfactants.

The microcapsules according to the invention can be used to microencapsulate various core materials such as chromogens and dyes, flavorants, perfumes, sweeteners, fragrances, oils, waxes, silicone oils, softening agents, vitamins, fats, pigments, cleaning oils, pharmaceuticals, pharmaceutical oils, perfume oils, mold inhibitors, antimicrobial agents, adhesives, phase change materials, scents, fertilizers, nutrients, and herbicides by way of illustration and without limitation.

Microencapsulation can facilitate processing by increasing particle size or by converting liquids into free flowing solids. The largest volume applications of microcapsules are in imaging systems such as carbonless papers.

The microcapsule wall can serve the purpose of extending shelf life, stabilize and protect the core material, mask strong flavors, or protect contents so that they are available to participate in reactions such as imaging or adhesive formation when the capsule wall is ruptured, sheared, fractured, broken or melted.

The core material can be a minor or major constituent of the material encapsulated by the microcapsules. If the core material can function as the oil or water solvent in the capsules, it is possible to make the core material the major or total material encapsulated. Usually however, the core material is from 0.01 to 99 weight percent of the capsule internal contents, preferably 0.01 to about 65 by weight of the capsule internal contents, and more preferably from 0.1 to about 45% by weight of the capsule internal contents. With certain especially potent materials, the core can be at just trace quantities.

In the process of the invention a first composition is prepared as an oil phase #1. The temperature of this oil phase is brought to a wall pre-reaction temperature. A nitrogen blanket is preferably employed and the solution mixed with high shear agitation to disperse the droplets. Gradually the temperature is increased to create a first composition reaction product.

A second oil phase is prepared and may be held at a pre-reaction temperature of the initiator.

The two oil solutions are allowed to pre-react and are combined. The mixtures are stirred and held at the pre-reaction temperature for sufficient time to pre-react the wall material. After the pre-reaction step, the water phase is added to the oil solutions.

The following is an illustration of preferred ranges with particular emulsifiers. Proportions are by weight.
For Cationic Capsule Type (Polyethyleneimine emulsifier):
Charged Materials (acid and base total quantity):
    Preferably: 0.1-20.0% by weight of total wall
    More Preferably: 0.5-10.0%
    Most Preferably: 1.0-5.0%
Acid/Base Molar proportions:
    Preferably: 3/1-1/3
    More Preferably: 2/1-1/2
    Most Preferably: 1.25/1-1/1.25
Water Phase pH:
    Preferably: 6-12
    More Preferably 7-11
    Most Preferably: 8-10
For Non-Ionic Capsule Type (Polyvinyl Alcohol emulsifier):
Charged Materials (acid and base total quantity):
    Preferably: 0.1-20.0% by weight of total wall
    More Preferably: 0.5-10.0%
    Most Preferably: 1.0-5.0%
Acid/Base Molar Proportions:
    Preferably: 3/1-1/3
    More Preferably: 2/1-1/2
    Most Preferably: 1.25/1-1/1.25

After wall pre-reaction, a water phase is prepared and added carefully to the oil solution. The solutions are milled and heated for a sufficient time to allow wall deposition to proceed. This process is further illustrated and explained in the examples.

Microcapsule particles according to the invention, by selection of curing conditions, wall materials, initiators, and concentration can select for a desired permeance level allowing formation of capsules with more targeted release profiles appropriate to the end use application. The process of the invention enables manufacture of capsules with different permeability levels. Permeability is conveniently expressed as release of less than a certain quantity of core material over a given time frame. For example, low permeability would be release of less than 1.0 mg/ml at 48 hours extraction time, or less than 2 mg/ml at 1 week extraction time or less than 5 mg/ml at four weeks extraction time. The desired end use application often will dictate the target release rate deemed acceptable to meet the needs of the application.

Slurry/Aggolmerate

In one aspect, a slurry that may comprise any of the particles disclosed in the present specification is disclosed. Said slurry may be combined with an adjunct ingredient to form a composition, for example, a consumer product.

In one aspect of said slurry one or more processing aids are selected from the group consisting of water, aggregate inhibiting materials such as divalent salts, particle suspending polymers, and mixtures thereof. Examples of aggregate inhibiting materials include salts that can have a charge-shielding effect around the particle, such as magnesium chloride, calcium chloride, magnesium bromide, magnesium sulfate, and mixtures thereof. Examples of particle suspending polymers include polymers such as xanthan gum, carrageenan gum, guar gum, shellac, alginates, chitosan; cellulosic materials such as carboxymethyl cellulose, hydroxypropyl methyl cellulose, cationically charged cellulosic materials; polyacrylic acid; polyvinyl alcohol; hydrogenated castor oil; ethylene glycol distearate; and mixtures thereof.

In one aspect, said slurry may comprise one or more processing aids, selected from the group consisting of water, aggregate inhibiting materials such as divalent salts; particle suspending polymers such as xanthan gum, guar gum, caboxy methyl cellulose.

In one aspect of the aforementioned slurry said one or more carriers may be selected from the group consisting of polar solvents, including but not limited to, water, ethylene glycol, propylene glycol, polyethylene glycol, glycerol; nonpolar solvents, including but not limited to, mineral oil, perfume raw materials, silicone oils, hydrocarbon paraffin oils, and mixtures thereof.

In one aspect of said slurry, said slurry may comprise a deposition aid that may comprise a polymer selected from the group comprising: polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, polyvinyl alcohol; polyvinyl alcohol crosslinked with boric acid; polyacrylic acid; polyglycerol ether silicone crosspolymers; polyacrylic acids, polyacrylates, copolymers of polyvinylamine and polyvinylalcohol oligomers of amines, in one aspect a diethylenetriamine, ethylene diamine, bis(3-aminopropyl)piperazine, N,N-Bis-(3-aminopropyl)methylamine, tris(2-aminoethyl)amine and mixtures thereof; polyethyleneimime, a derivatized polyethyleneimine, in one aspect an ethoxylated polyethyleneimine; a polymeric compound comprising, at least two moieties selected from the moieties consisting of a carboxylic acid moiety, an amine moiety, a hydroxyl moiety, and a nitrile moiety on a backbone of polybutadiene, polyisoprene, polybutadiene/styrene, polybutadiene/acrylonitrile, carboxyl-terminated polybutadiene/acrylonitrile or combinations thereof; pre-formed coacervates of anionic surfactants combined with cationic polymers; polyamines and mixtures thereof.

In one aspect, an agglomerate that comprises said particles and a second material is disclosed.

In one aspect of said agglomerate, said second material may comprise a material selected from the group consisting of silicas, citric acid, sodium carbonate, sodium sulfate, sodium chloride, and binders such as sodium silicates, modified celluloses, polyethylene glycols, polyacrylates, polyacrylic acids, zeolites and mixtures thereof.

Consumer Products

In one aspect, a composition comprising an adjunct ingredient and a population of microcapsule particles comprising an oil soluble or dispersible core material and a non-anionic wall material at least partially surrounding the core material, the microcapsule wall material comprising:

the reaction product of a first composition in the presence of a second composition comprising an emulsifier which is non-anionic, the first composition comprising a reaction product of i) an oil soluble or dispersible amine acrylate or methacrylate with ii) a multifunctional acrylate or methacrylate monomer or oligomer, and iii) a soluble acid and an initiator, wherein the soluble acid and the amine acrylate are in a molar proportion from 3:1 to 1:3 and together have a percent by weight as compared to the weight of the wall material of from 0.1 to 20%, the non-anionic emulsifier comprising a water soluble or dispersible material at a pH from 4 to 12, and optionally a water phase initiator, whereby the reaction product of the first composition and second composition results in the formation of a population of microcapsules having a non-anionic microcapsule wall material of low permeance to the core material and having a zeta potential of −5 millivolts or greater, the resulting microcapsules having adherence to anionic surfaces; said composition being a consumer product or even, in one aspect, a cleaning composition, fabric care composition and/or a personal care composition is disclosed.

In one aspect of said composition, the emulsifier may be cationic.

In one aspect of said composition, the cationic emulsifier may be selected from palmitamidopropyltrimonium chloride, distearyl dimonium chloride, cetyltrimethylammonium chloride, quaternary ammonium compounds, fatty amines, aliphatic ammonium halides, alkyldimethylbenzylammonium halides, alkyldimethylethylammonium halides, polyethyleneimine, poly(2-dimethylamino)ethyl methacrylate) methyl chloride quaternary salt, poly(1-vinylpyrrolidone-co-2-dimethylaminoethyl methacrylate), poly(acrylamide-co-diallyldimethylammonium chloride), poly(allylamine), poly[bis(2-chloroethyl)ether-alt-1,3-bis[3-(dimethylamino)propyl]urea] quaternized, poly(dimethylamine-co-epichlorohydrin-co-ethylenediamine) and condensation products of aliphatic amines with alkylene oxide.

In one aspect of said composition, the soluble acid and amine acrylate may have a percent by weight as compared to the weight of the wall material of from 1 to 5 percent.

In one aspect of said composition, the soluble acid and amine acrylate may have a molar proportion of from 1.25/1 to 1/1.25.

In one aspect of said composition, the non-anionic emulsifier may comprise a water soluble or dispersible material at a pH of from 8-10.

In one aspect of said composition, the emulsifier may be nonionic.

In one aspect of said composition, the nonionic emulsifier may be selected from polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, partially hydrolyzed polyvinyl alcohol, polyvinyl acetate, copolymers of polyvinyl alcohol, copolymers of polyvinyl acetate, polyacrylamide, poly(N-isopropylacrylamide), poly(2-hydroxypropyl methacrylate), poly(2-ethyl-2-oxazoline), poly(2-isopropenyl-2-oxazoline-co-methyl methacrylate), poly(methyl vinyl ether), and polyvinyl alcohol-co-ethylene).

In one aspect of said composition, the soluble acid and amine acrylate may have a percent by weight as compared to the weight of the wall material of from 1 to 5 percent.

In one aspect of said composition, the soluble acid and amine acrylate may have a molar proportion of from 1.25/1 to 1/1.25.

In one aspect of said composition, the emulsifier may have a molecular weight greater than about 100, and may be selected from polymers with primary, secondary or tertiary amine functionality.

In one aspect of said composition, the emulsifier may have a molecular weight greater than 100 and may be selected from polymers with hydroxyl, ether, ester, ketone or amide functionality.

In one aspect of said composition, said population of microcapsule particles may have a capsule retention value on cotton fiber of at least 1 mg oil.

In one aspect a composition comprising an adjunct ingredient and a population of microcapsule particles comprising an oil soluble or dispersible core material and a non-anionic wall material at least partially surrounding the core material, the microcapsule wall material comprising:

the reaction product of a first composition in the presence of a second composition comprising an emulsifier which is cationic or nonionic, the first composition comprising a reaction product of i) an oil soluble or dispersible acid acrylate or methacrylate with ii) a multifunctional acrylate or methacrylate monomer or oligomer, and iii) a soluble base and an initiator; wherein the soluble base and the acid acrylate or methacrylate are in a molar proportion from 3:1 to 1:3 and together have a percent by weight as compared to the weight of the wall material of from 0.1 to 20%; the non-anionic emulsifier comprising a water soluble or water dispersible material at a pH from 4 to 12, and optionally a water phase initiator, whereby the reaction product of the first composition and second composition results in the formation of a population of microcapsules having a non-anionic microcapsule wall of low permeance to the core material and having a zeta potential of −5 millivolts or greater, the resulting microcapsules having adherence to anionic surfaces said composition being a consumer product or even, in one aspect, a cleaning composition, fabric care composition and/or a personal care composition is disclosed.

In one aspect of said composition, the emulsifier may be cationic.

In one aspect of said composition, the cationic emulsifier may be selected from palmitamidopropyltrimonium chloride, distearyl dimonium chloride, cetyltrimethylammonium chloride, quaternary ammonium compounds, fatty amines, aliphatic ammonium halides, alkyldimethylbenzylammonium halides, alkyldimethylethylammonium halides, polyethyleneimine, poly(2-dimethylamino)ethyl methacrylate) methyl chloride quaternary salt, poly(1-vinylpyrrolidone-co-2-dimethylaminoethyl methacrylate), poly(acrylamide-co-diallyldimethylammonium chloride), poly(allylamine), poly[bis(2-chloroethyl)ether-alt-1,3-bis[3-(dimethylamino)propyl]urea] quaternized, poly(dimethylamine-co-epichlorohydrin-co-ethylenediamine) and condensation products of aliphatic amines with alkylene oxide.

In one aspect of said composition, the soluble acid and amine acrylate may have a percent by weight as compared to the weight of the wall material of from 1 to 5 percent.

In one aspect of said composition, the soluble acid and amine acrylate may have a molar proportion of from 1.25/1 to 1/1.25.

In one aspect of said composition, the non-anionic emulsifier may comprise a water soluble or dispersible material at a pH of from 8-10.

In one aspect of said composition, the emulsifier may be nonionic.

In one aspect of said composition, the nonionic emulsifier may be selected from polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, polyvinyl acetate, copolymers of polyvinyl alcohol, copolymers of polyvinyl acetate, polyacrylamide, poly(N-isopropylacrylamide), poly(2-hydroxypropyl methacrylate), poly(2-ethyl-2-oxazoline), poly(2-isopropenyl-2-oxazoline-co-methyl methacrylate), poly(methyl vinyl ether), and polyvinyl alcohol-co-ethylene).

In one aspect of said composition, the soluble acid and amine acrylate may have a percent by weight as compared to the weight of the wall material of from 1 to 5 percent.

In one aspect of said composition, the soluble acid and amine acrylate may have a molar proportion of from 1.25/1 to 1/1.25.

In one aspect of said composition, the emulsifier may have a molecular weight greater than about 100, and may be selected from polymers with primary, secondary or tertiary amine functionality.

In one aspect of said composition, the emulsifier may have a molecular weight greater than 100 and may be selected from polymers having a hydroxyl, ether, ester, ketone or amide functionality.

In one aspect of said composition, the nonionic emulsifier may be partially hydrolyzed polyvinyl alcohol in the range of from 85 to 95% hydrolyzed.

In one aspect of said composition, said population of microcapsules may have a capsule retention value on cotton fiber of at least 1 mg oil.

In one aspect of said composition, said particles may be contained in a slurry that is combined with said adjunct.

In one aspect of said composition, said slurry may comprise one or more processing aids, selected from the group consisting of water, aggregate inhibiting materials such as divalent salts; particle suspending polymers such as xanthan gum, guar gum, caboxy methyl cellulose.

In one aspect of said composition, said particles may be contained in an agglomerate that is combined with said adjunct.

In one aspect of said composition, said agglomerate may comprise materials selected from the group consisting of silicas, citric acid, sodium carbonate, sodium sulfate, sodium chloride, and binders such as sodium silicates, modified celluloses, polyethylene glycols, polyacrylates, polyacrylic acids, zeolites and mixtures thereof.

In one aspect of said composition, said adjunct may be selected from the group consisting of polymers, in one aspect, a cationic polymer, surfactants, builders, chelating agents, dye transfer inhibiting agents, dispersants, enzymes, enzyme stabilizers, catalytic materials, bleach activators, polymeric dispersing agents, clay soil removal/anti-redeposition agents, brighteners, dye polymer conjugates; dye clay conjugates, suds suppressors, dyes, bleach catalysts, additional perfume and/or perfume delivery systems, structure elasticizing agents, fabric softeners, carriers, hydrotropes, processing aids, rheology modifiers, structurants, thickeners, pigments, water and mixtures thereof.

In one aspect of said composition, said composition may comprise a material selected from the group consisting of dyes; perfume; optical brighteners; rheology modifiers, structurants, thickeners, deposition aids; and mixtures thereof.

In one aspect of said composition, said composition may comprise a deposition aid that may comprise a polymer selected from the group comprising: polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, polyvinyl alcohol; polyvinyl alcohol crosslinked with boric acid; polyacrylic acid; polyglycerol ether silicone crosspolymers; polyacrylic acids, polyacrylates, copolymers of polyvinylamine and polyvinylalcohol oligomers of amines, in one aspect a diethylenetriamine, ethylene diamine, bis(3-aminopropyl)piperazine, N,N-Bis-(3-aminopropyl)methylamine, tris(2-aminoethyl)amine and mixtures thereof; polyethyleneimime, a derivatized polyethyleneimine, in one aspect an ethoxylated polyethyleneimine; a polymeric compound comprising, at least two moieties selected from the moieties consisting of a carboxylic acid moiety, an amine moiety, a hydroxyl moiety, and a nitrile moiety on a backbone of polybutadiene, polyisoprene, polybutadiene/styrene, polybutadiene/acrylonitrile, carboxyl-terminated polybutadiene/acrylonitrile or combinations thereof; pre-formed coacervates of anionic surfactants combined with cationic polymers; polyamines and mixtures thereof.

In one aspect of said composition, at least 75% of said particles may have a fracture strength of from about 0.2 MPa to about 30 MPa; from about 0.6 MPa to about 10 MPa, from about 1.0 MPa to about 5 MPa, or from about 1.2 MPa to about 3 MPa.

In one aspect, said composition comprises a rheology modifier, thickener and/or structurant having a high shear viscosity, at 20 sec-1 shear rate and at 21° C., of from 1 to 7000 cps and a viscosity at low shear (0.5 sec-1 shear rate at 21° C.) of greater than 1000 cps, or even 1000 cps to 200,000 cps. In one aspect, for cleaning and treatment compositions, such rheology modifiers impart to the aqueous liquid composition a high shear viscosity, at 20 sec-1 and at 21° C., of from 50 to 3000 cps and a viscosity at low shear (0.5 sec-1 shear rate at 21° C.) of greater than 1000 cps, or even 1000 cps to 200,000 cps. In one aspect, suitable rheology modifiers, thickeners and/or structurants may be selected from the group consisting of polyacrylates, polymethacrylates, polycarboxylates, polymeric gums like pectine, alginate, arabinogalactan (gum Arabic), carrageenan, gellan gum, xanthan gum and guar gum, other non-gum polysaccharides like gellan gum, and combinations of these polymeric materials, hydroxyl-containing fatty acids, fatty esters or fatty waxes, castor oil and its derivatives, hydrogenated castor oil derivatives such as hydrogenated castor oil and hydrogenated castor wax; and mixtures thereof.

In one aspect of said composition, said composition may be a fluid detergent and that may comprise, based on total fluid detergent weight, less than about less then about 80% water, less than about 60% to about 2% water, from about 45% to about 7% water, from about 35% to about 9% water.

In one aspect of said composition, said composition may have a viscosity of from about 10 cps to about 999 cps, or even from about 100 cps to about 800 cps at a shear rate of 1 sec-1.

In one aspect of said composition, said composition may be a gel comprising, based on total gel weight, less than about 45% water less than about 45% to about 2% water, from about 45% to about 7% water, from about 35% to about 9% water and may have a neat viscosity of from about 1,000 cps to about 10,000 cps or even from about 1,200 cps to about 8,000 cps; In one aspect of said composition, said composition may be a fluid fabric enhancer; a solid fabric enhancer; a fluid shampoo; a solid shampoo; hair conditioner; body wash, solid antiperspirant, fluid antiperspirant, solid deodorant, fluid deodorant, fluid detergent, solid detergent, fluid hard surface cleaner, solid hard surface cleaner; or a unit dose detergent comprising a detergent and a water soluble film encapsulating said detergent.

In other aspects, the compositions disclosed herein may have any combination of materials and/or characteristics disclosed herein.

Aspects of the invention include the use of the particles of the present invention in laundry detergent compositions (e.g., TIDE™), hard surface cleaners (e.g., MR CLEAN™) automatic dishwashing liquids (e.g., CASCADE™), and floor cleaners (e.g., SWIFFER™) Non-limiting examples of cleaning compositions may include those described in U.S. Pat. Nos. 4,515,705; 4,537,706; 4,537,707; 4,550,862; 4,561,998; 4,597,898; 4,968,451; 5,565,145; 5,929,022; 6,294,514; and 6,376,445. The cleaning compositions disclosed herein are typically formulated such that, during use in aqueous cleaning operations, the wash water will have a pH of between about 6.5 and about 12, or between about 7.5 and 10.5. Liquid dishwashing product formulations typically have a pH between about 6.8 and about 9.0. Cleaning products are typically formulated to have a pH of from about 7 to about 12. Techniques for controlling pH at recommended usage levels include the use of buffers, alkalis, acids, etc., and are well known to those skilled in the art.

Aspects of the invention especially include the use of the particles in personal care compositions. The personal care compositions of the present invention can be applied to the skin and/or hair. The compositions can be, for example, formulated as bars, liquids, emulsions, shampoos, gels, powders, sticks, hair conditioners (rinse off and leave in), hair tonics, pastes, hair colorants, sprays, mousses and/or other styling products.

Personal Care Compositions

In one aspect, the consumer products disclosed herein may be personal care compositions comprising any aspect of the particles described in the present specification. Such compositions may be in solid or fluid form. Such compositions can be applied to the skin and/or hair or in other embodiments used to treat and/clean a situs. The compositions can be, for example, formulated as bars, liquids, emulsions, shampoos, gels, powders, sticks, hair conditioners (rinse off and leave in), hair tonics, pastes, hair colorants, sprays, mousses and other styling products.

In one embodiment, the particle is incorporated into a personal care composition suitable for use before, during or after hair removal. The personal care composition of the present invention can be used in combination with various hair removal applications (prior to, concurrently with, and/or after), including but not limited to shaving (wet or dry shaving, via electric razors, via powered or manual razors which can be reusable or disposable, and combinations thereof), epilation, electrolysis, wax or depilatories as well as energy delivery devices to help regulate hair growth. The hair removal composition can be an aerosol, such as an aerosol shave preparation which can be a foam, gel, or post foaming gel, or a non-aerosol shave preparation such as generally available in the market. In one embodiment, the shave preparation is an emulsion which can be in the form of a cream or lotion, or the shave preparation can be a gel, which most commonly consists of polymer thickened surfactant systems.

In one embodiment, the particle is incorporated into a shaving aid which can be incorporated into a shaving razor cartridge. Those of skill in the art will understand that shaving aids are also commonly referred to as lubricating strips. Suitable shaving aids and/or lubricating strips are disclosed in U.S. Pat. Nos. 7,069,658, 6,944,952, 6,594,904, 6,182,365, 6,185,822, 6,298,558 and 5,113,585, and U.S. Design Pat. No. D424,745. In one embodiment, the shaving aid comprises from about 50% to about 95% of a lubricious water soluble polymer, selected from the group consisting of polyethylene oxide; polyvinyl pyrrolidone, polyacrylamide, modified hydroxyalkyl cellulose, polyvinyl imidazoline, polyvinyl alcohol, polysulfone, polyhydroxyethyl-methacrylate, and mixture thereof. The shaving aid may also include from about 1% to about 50% of a non-soluble polymer selected from the group consisting of polyethylene, polypropylene, polystyrene, butadiene-styrene copolymer, polyacetal, acrylonitrile-butadiene-styrene copolymer, ethylene vinyl acetate copolymer, polyurethante, and mixtures thereof.

The compositions of the present inventions may include the following components:

A. Detersive Surfactant

The composition of the present invention may include a detersive surfactant. The detersive surfactant component may comprise anionic detersive surfactant, zwitterionic or amphoteric detersive surfactant, or a combination thereof. The concentration of the anionic surfactant component in the composition should be sufficient to provide the desired cleaning and lather performance, and generally range from about 5% to about 50%. Anionic surfactants suitable for use in the compositions are the alkyl and alkyl ether sulfates. Other suitable anionic detersive surfactants are the water-soluble salts of organic, sulfuric acid reaction products conforming to the formula [$R^1$—$SO_3$-M] where $R^1$ is a straight or branched chain, saturated, aliphatic hydrocarbon radical having from about 8 to about 24, or about 10 to about 18, carbon atoms; and M is a cation described hereinbefore. Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic detersive surfactants suitable for use in the compositions are the succinates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic detersive surfactants suitable for use in the compositions is the beta-alkyloxy alkane sulfonates. These surfactants conform to the formula

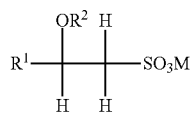

where $R^1$ is a straight chain alkyl group having from about 6 to about 20 carbon atoms, $R^2$ is a lower alkyl group having from about 1 to about 3 carbon atoms, or even 1 carbon atom, and M is a water-soluble cation as described hereinbefore.

U.S. Pat. Nos. 3,929,678, 2,658,072; 2,438,091; 2,528,378.

B. Cationic Surfactant System

The composition of the present invention may comprise a cationic surfactant system. The cationic surfactant system can be one cationic surfactant or a mixture of two or more cationic surfactants. If present, the cationic surfactant system is included in the composition at a level by weight of from about 0.1% to about 10%, from about 0.5% to about 8%, from about 1% to about 5%, or even from about 1.4% to about 4%, in view of balance among ease-to-rinse feel, rheology and wet conditioning benefits.

A variety of cationic surfactants including mono- and di-alkyl chain cationic surfactants can be used in the compositions of the present invention. Examples of suitable materials include mono-alkyl chain cationic surfactants in view of the desired gel matrix and wet conditioning benefits. The mono-alkyl cationic surfactants are those having one long alkyl chain which has from 12 to 22 carbon atoms, from 16 to 22 carbon atoms, or a $C_{18}$-$C_{22}$ alkyl group, in view of providing balanced wet conditioning benefits. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. Such mono-alkyl cationic surfactants include, for example, mono-alkyl quaternary ammonium salts and mono-alkyl amines. Mono-alkyl quaternary ammonium salts include, for example, those having a non-functionalized long alkyl chain. Mono-alkyl amines include, for example, mono-alkyl amidoamines and salts thereof.

Mono-long alkyl quaternized ammonium salts useful herein are those having the formula

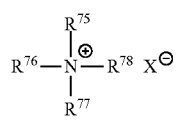

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. In one aspect, one of $R^{75}$, $R^{76}$, $R^{77}$ and $R^{78}$ is selected from an alkyl group of from 12 to 30 carbon atoms, in another aspect, from 16 to 22 carbon atoms, in another aspect, from 18 to 22 carbon atoms, or even 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Examples of suitable mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt. Among them, highly useful materials are behenyl trimethyl ammonium salt and stearyl trimethyl ammonium salt.

Mono-alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; in one aspect, l-glutamic acid, lactic acid, citric acid are highly useful. In one aspect, amines herein are partially neutralized with any of the acids at a molar ratio of the amine to the acid of from about 1:0.3 to about 1:2, or even from about 1:0.4 to about 1:1.

Although the mono-alkyl chain cationic surfactants are useful, other cationic surfactants such as di-alkyl chain cationic surfactants may also be used alone, or in combination with the mono-alkyl chain cationic surfactants. Such di-alkyl chain cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

C. High Melting Point Fatty Compound

The composition of the present invention may include a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section.

Among a variety of high melting point fatty compounds, fatty alcohols are used in one aspect the present invention. The fatty alcohols useful herein are those having from about 14 to about 30 carbon atoms, or even from about 16 to about 22 carbon atoms. These fatty alcohols are saturated and can be straight or branched chain alcohols. In one aspect, fatty alcohols include, for example, cetyl alcohol, stearyl alcohol, behenyl alcohol, and mixtures thereof.

High melting point fatty compounds of a single compound of high purity are typically used. In one aspect, single compounds of pure fatty alcohols selected from the group of pure cetyl alcohol, stearyl alcohol, and behenyl alcohol are employed. By "pure" herein, what is meant is that the compound has a purity of at least about 90%, or even at least about 95%. These single compounds of high purity provide good rinsability from the hair when the consumer rinses off the composition.

The high melting point fatty compound is included in the composition at a level of from about 0.1% to about 40%, from about 1% to about 30%, from about 1.5% to about 16% by weight of the composition, or even from about 1.5% to about 8% in view of providing improved conditioning benefits such as slippery feel during the application to wet hair, softness and moisturized feel on dry hair.

D. Cationic Polymers

The compositions of the present invention may contain a cationic polymer. Concentrations of the cationic polymer in the composition typically range from about 0.05% to about 3%, in another embodiment from about 0.075% to about 2.0%, and in yet another embodiment from about 0.1% to about 1.0%. Suitable cationic polymers will have cationic charge densities of at least about 0.5 meq/gm, in another embodiment at least about 0.9 meq/gm, in another embodiment at least about 1.2 meq/gm, in yet another embodiment at least about 1.5 meq/gm, but in one embodiment also less than about 7 meq/gm, and in another embodiment less than about 5 meq/gm, at the pH of intended use of the composition, which pH will generally range from about pH 3 to about pH 9, in one embodiment between about pH 4 and about pH 8. Herein, "cationic charge density" of a polymer refers to the ratio of the number of positive charges on the polymer to the molecular weight of the polymer. The average molecular weight of such suitable cationic polymers will generally be between about 10,000 and 10 million, in one embodiment between about 50,000 and about 5 million, and in another embodiment between about 100,000 and about 3 million.

Suitable cationic polymers for use in the compositions of the present invention contain cationic nitrogen-containing moieties such as quaternary ammonium or cationic protonated amino moieties. The cationic protonated amines can be primary, secondary, or tertiary amines (in one aspect, secondary or tertiary), depending upon the particular species and the selected pH of the composition. Any anionic counterion can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methyl sulfate.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); amphoteric copolymers of acrylic acid including copolymers of acrylic acid and dimethyldiallylammonium chloride (referred to in the industry by CTFA as Polyquaternium 22), terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methyl acrylate (referred to in the industry by CTFA as Polyquaternium 47). In one aspect, cationic substituted monomers may be the cationic substituted dialkylaminoalkyl acrylamides, dialkylaminoalkyl methacrylamides, and combinations thereof. Such monomers conform to the formula

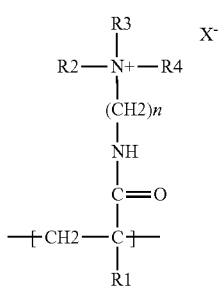

wherein $R^1$ is hydrogen, methyl or ethyl; each of $R^2$, $R^3$ and $R^4$ are independently hydrogen or a short chain alkyl having from about 1 to about 8 carbon atoms, from about 1 to about 5 carbon atoms, or even from about 1 to about 2 carbon atoms; n is an integer having a value of from about 1 to about 8, or even from about 1 to about 4; and X is a counterion. The nitrogen attached to $R^2$, $R^3$ and $R^4$ may be a protonated amine (primary, secondary or tertiary), but is in one aspect, a quaternary ammonium wherein each of $R^2$, $R^3$ and $R^4$ are alkyl groups a non limiting example of which is polymethacrylamidopropyl trimonium chloride, available under the trade name Polycare® 133, from Rhone-Poulenc, Cranberry, N.J., U.S.A.

Other suitable cationic polymers for use in the composition include polysaccharide polymers, such as cationic cellulose derivatives and cationic starch derivatives. Suitable cationic polysaccharide polymers include those which conform to the formula

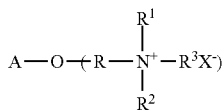

wherein A is an anhydroglucose residual group, such as a starch or cellulose anhydroglucose residual; R is an alkylene oxyalkylene, polyoxyalkylene, or hydroxyalkylene group, or combination thereof; $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) is typically about 20 or less; and X is an anionic counterion as described in hereinbefore.

Useful cationic cellulose polymers include salts of hydroxyethyl cellulose reacted with trimethyl ammonium substituted epoxide, referred to in the industry (CTFA) as Polyquatemium 10 and available from Amerchol Corp. (Edison, N.J., USA) in their Ucare™ Polymer LR, Ucare™ Polymer JR, and Ucare™ Polymer KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corp. under the trade name Ucare™ Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance® series commercially available from Aqualon Division of Hercules, Inc. Other suitable cationic polymers include quaternary nitrogen-containing cellulose ethers, some examples of which are described in U.S. Pat. No. 3,962,418. Other suitable polymers include synthetic polymers such as those disclosed in U.S. Publication No. 2007/0207109A1. Other suitable cationic polymers include copolymers of etherified cellulose, guar and starch, some examples of which are described in U.S. Pat. No. 3,958,581. When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

E. Nonionic Polymers

The composition of the present invention may include a nonionic polymer. Polyalkylene glycols having a molecular weight of more than about 1000 are useful herein. Useful are those having the following general formula:

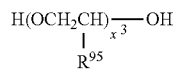

wherein $R^{95}$ is selected from the group consisting of H, methyl, and mixtures thereof. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

F. Conditioning Agents

Conditioning agents, and in particular silicones, may be included in the composition. Conditioning agents include any material which is used to give a particular conditioning benefit to hair and/or skin. In hair treatment compositions, suitable conditioning agents are those which deliver one or more benefits relating to shine, softness, compatibility, antistatic properties, wet-handling, damage, manageability, body, and greasiness. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

1. Silicones

The conditioning agent of the compositions of the present invention can be an insoluble silicone conditioning agent. The silicone conditioning agent particles may comprise volatile silicone, non-volatile silicones, or combinations thereof. In one aspect, non-volatile silicones conditioning agents are employed. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from about 0.01% to about 10%, from about 0.1% to about 8%, from about 0.1% to about 5%, or even from about 0.2% to about 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention typically have a viscosity, as measured at 25° C., from about 20 centistokes to about 2,000,000 centistokes ("cst"), from about 1,000 cst to about 1,800,000 cst, from about 50,000 cst to about 1,500,000 cst, or even from about 100,000 cst to about 1,500,000 csk.

The dispersed silicone conditioning agent particles typically have a number average particle diameter ranging from about 0.01 μm to about 50 μm. For small particle application to hair, the number average particle diameters typically range from about 0.01 μm to about 4 μm, from about 0.01 μm to about 2 μm, or even from about 0.01 μm to about 0.5 μm. For larger particle application to hair, the number average particle diameters typically range from about 4 μm to about 50 μm, from about 6 μm to about 30 μm, from about 9 μm to about 20 μm, or even from about 12 μm to about 18 μm.

a. Silicone Oils

Silicone fluids may include silicone oils, which are flowable silicone materials having a viscosity, as measured at 25° C., less than 1,000,000 cst, from about 5 cst to about 1,000,000 cst, or even from about 100 cst to about 600,000 cst. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

b. Amino and Cationic Silicones

Compositions of the present invention may include an aminosilicone Aminosilicones, as provided herein, are silicones containing at least one primary amine, secondary amine, tertiary amine, or a quaternary ammonium group. Useful aminosilicones may have less than about 0.5% nitrogen by weight of the aminosilicone, less than about 0.2%, or even less than about 0.1%. Higher levels of nitrogen (amine functional groups) in the amino silicone tend to result in less friction reduction, and consequently less conditioning benefit from the aminosilicone. It should be understood that in some product forms, higher levels of nitrogen are acceptable in accordance with the present invention.

In one aspect, the aminosilicones used in the present invention have a particle size of less than about 50μ once incorporated into the final composition. The particle size measurement is taken from dispersed droplets in the final composition. Particle size may be measured by means of a laser light scattering technique, using a Horiba model LA-930 Laser Scattering Particle Size Distribution Analyzer (Horiba Instruments, Inc.).

In one embodiment, the aminosilicone typically has a viscosity of from about 1,000 cst (centistokes) to about 1,000,000 cst, from about 10,000 to about 700,000 cst, from about 50,000 cst to about 500,000 cst, or even from about 100,000 cst to about 400,000 cst. This embodiment may also comprise a low viscosity fluid, such as, for example, those materials described below in Section F.(1). The viscosity of aminosilicones discussed herein is measured at 25° C.

In another embodiment, the aminosilicone typically has a viscosity of from about 1,000 cst to about 100,000 cst, from about 2,000 cst to about 50,000 cst, from about 4,000 cst to about 40,000 cst, or even from about 6,000 cst to about 30,000 cs.

The aminosilicone typically is contained in the composition of the present invention at a level by weight of from about 0.05% to about 20%, from about 0.1% to about 10%, and or even from about 0.3% to about 5%.

c. Silicone Gums

Other silicone fluids suitable for use in the compositions of the present invention are the insoluble silicone gums. These gums are polyorganosiloxane materials having a viscosity, as measured at 25° C., of greater than or equal to 1,000,000 csk. Specific non-limiting examples of silicone gums for use in the compositions of the present invention include polydimethylsiloxane, (polydimethylsiloxane)(methylvinylsiloxane) copolymer, poly(dimethylsiloxane)(diphenyl siloxane)(methylvinylsiloxane) copolymer and mixtures thereof.

d. High Refractive Index Silicones

Other non-volatile, insoluble silicone fluid conditioning agents that are suitable for use in the compositions of the present invention are those known as "high refractive index silicones," having a refractive index of at least about 1.46, at least about 1.48, m at least about 1.52, or even at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (III) above, as well as cyclic polysiloxanes such as those represented by Formula (VIII) below:

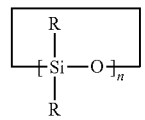

wherein R is as defined above, and n is a number from about 3 to about 7, or even from about 3 to about 5.

Silicone fluids suitable for use in the compositions of the present invention are disclosed in U.S. Pat. No. 2,826,551, U.S. Pat. No. 3,964,500, and U.S. Pat. No. 4,364,837.

e. Silicone Resins

Silicone resins may be included in the conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence.

In one aspect, silicone resins for use in the compositions of the present invention include, but are not limited to MQ, MT, MTQ, MDT and MDTQ resins. In one aspect, Methyl is a highly suitable silicone substituent. In another aspect, silicone resins are typically MQ resins, wherein the M:Q ratio is typically from about 0.5:1.0 to about 1.5:1.0 and the average molecular weight of the silicone resin is typically from about 1000 to about 10,000.

f. Modified Silicones or Silicone Copolymers

Other modified silicones or silicone copolymers are also useful herein. Examples of these include silicone-based quaternary ammonium compounds (Kennan quats) disclosed in U.S. Pat. Nos. 6,607,717 and 6,482,969; end-terminal quaternary siloxanes; silicone aminopolyalkyleneoxide block copolymers disclosed in U.S. Pat. Nos. 5,807,956 and 5,981, 681; hydrophilic silicone emulsions disclosed in U.S. Pat. No. 6,207,782; and polymers made up of one or more crosslinked rake or comb silicone copolymer segments disclosed in U.S. Pat. No. 7,465,439. Additional modified silicones or silicone copolymers useful herein are described in US Patent Application Nos. 2007/0286837A1 and 2005/0048549A1.

In alternative embodiments of the present invention, the above-noted silicone-based quaternary ammonium compounds may be combined with the silicone polymers described in U.S. Pat. Nos. 7,041,767 and 7,217,777 and US Application number 2007/0041929A1.

2. Organic Conditioning Oils

The compositions of the present invention may also comprise from about 0.05% to about 3%, from about 0.08% to about 1.5%, or even from about 0.1% to about 1%, of at least one organic conditioning oil as the conditioning agent, either alone or in combination with other conditioning agents, such as the silicones (described herein). Suitable conditioning oils include hydrocarbon oils, polyolefins, and fatty esters. Suitable hydrocarbon oils include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils are typically from about $C_{12}$ to about $C_{19}$. Branched chain hydrocarbon oils, including hydrocarbon polymers, typically will contain more than 19 carbon atoms. Suitable polyolefins include liquid polyolefins, liquid poly-α-olefins, or even hydrogenated liquid poly-α-olefins. Polyolefins for use herein may be prepared by polymerization of $C_4$ to about $C_{14}$ or even $C_6$ to about $C_{12}$. Suitable fatty esters include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

3. Other Conditioning Agents

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586, 4,507,280, 4,663,158, 4,197,865, 4,217, 914, 4,381,919, and 4,422, 853.

G. Anti-Dandruff Actives

The compositions of the present invention may also contain an anti-dandruff agent. Suitable, non-limiting examples of anti-dandruff actives include: antimicrobial actives, pyridinethione salts, azoles, selenium sulfide, particulate sulfur, keratolytic acid, salicylic acid, octopirox (piroctone olamine), coal tar, and combinations thereof. In one aspect, the anti-dandruff actives typically are pyridinethione salts. Such anti-dandruff particulate should be physically and chemically compatible with the essential components of the composition, and should not otherwise unduly impair product stability, aesthetics or performance.

Pyridinethione anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379, 753; and U.S. Pat. No. 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

H. Humectant

The compositions of the present invention may contain a humectant. The humectants herein are selected from the group consisting of polyhydric alcohols, water soluble alkoxylated nonionic polymers, and mixtures thereof. The humectants, when used herein, are typically used at levels of from about 0.1% to about 20%, or even from about 0.5% to about 5%.

I. Suspending Agent

The compositions of the present invention may further comprise a suspending agent at concentrations effective for suspending water-insoluble material in dispersed form in the compositions or for modifying the viscosity of the composition. Such concentrations range from about 0.1% to about 10%, or even from about 0.3% to about 5.0%.

Suspending agents useful herein include anionic polymers and nonionic polymers. Useful herein are vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (*Cydonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Commercially available viscosity modifiers highly useful herein include Carbomers with trade names Carbopol® 934, Carbopol® 940, Carbopol® 950, Carbopol® 980, and Carbopol® 981, all available from B. F. Goodrich Company, acrylates/steareth-20 methacrylate copolymer with trade name ACRYSOL™ 22 available from Rohm and Hass, nonoxynyl hydroxyethylcellulose with trade name Amercell™ POLYMER HM-1500 available from Amerchol, methylcellulose with trade name BENECEL®, hydroxyethyl cellulose with trade name NATROSOL®, hydroxypropyl cellulose with trade name KLUCEL®, cetyl hydroxyethyl cellulose with trade name POLYSURF® 67, all supplied by Hercules, ethylene oxide and/or propylene oxide based polymers with trade names CARBOWAX® PEGs, POLYOX WASRs, and UCON® FLUIDS, all supplied by Amerchol.

Other optional suspending agents include crystalline suspending agents which can be categorized as acyl derivatives, long chain amine oxides, and mixtures thereof. These suspending agents are described in U.S. Pat. No. 4,741,855.

These suspending agents include ethylene glycol esters of fatty acids in one aspect having from about 16 to about 22 carbon atoms. In one aspect, useful suspending agents include ethylene glycol stearates, both mono and distearate, but in one aspect, the distearate containing less than about 7% of the mono stearate. Other suitable suspending agents include alkanol amides of fatty acids, having from about 16 to about 22 carbon atoms, or even about 16 to 18 carbon atoms, examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin® R available from Rheox, Inc. Long chain acyl derivatives, ethylene glycol esters of long chain carboxylic acids, long chain amine oxides, and alkanol amides of long chain carboxylic acids in addition to the materials listed above may be used as suspending agents.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl dimethyl amine oxides, e.g., stearyl dimethyl amine oxide.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow) amine. Still other suitable suspending agents include di(hydrogenated tallow)phthalic acid amide, and crosslinked maleic anhydride-methyl vinyl ether copolymer.

J. Aqueous Carrier

The formulations of the present invention can be in the form of pourable liquids (under ambient conditions). Such compositions will therefore typically comprise an aqueous carrier, which is present at a level of from about 20% to about 95%, or even from about 60% to about 85%. The aqueous carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful in the present invention includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

K. Dispersed Particles

The compositions may optionally comprise particles. The particles may be dispersed water-insoluble particles. The particles may be inorganic, synthetic, or semi-synthetic. In one embodiment, the particles have an average mean particle size of less than about 300 μm.

L. Gel Matrix

The above cationic surfactants, together with high melting point fatty compounds and an aqueous carrier, may form a gel matrix in the composition of the present invention.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, from about 1:1 to about 1:10, or even from about 1:1 to about 1:6.

M. Skin Care Actives

The composition may comprise at least one skin care active, useful for regulating and/or improving the condition and/or appearance of mammalian skin. The skin care active may be soluble in oil or water, and may be present primarily in the oil phase and/or in the aqueous phase. Suitable actives include, but are not limited to, vitamins, peptides, sugar amines, sunscreens, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobials, and antifungals.

The composition may comprise from about 0.001% to about 10%, alternatively from about 0.01% to about 5%, of at least one vitamin. Herein, "vitamins" means vitamins, provitamins, and their salts, isomers and derivatives. Non-limiting examples of suitable vitamins include: vitamin B compounds (including B1 compounds, B2 compounds, B3 compounds such as niacinamide, niacinnicotinic acid, tocopheryl nicotinate, $C_1$-$C_{18}$ nicotinic acid esters, and nicotinyl alcohol; B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids. In one embodiment, the composition may comprise a vitamin selected from the group consisting of vitamin B compounds, vitamin C compounds, vitamin E compounds and mixtures thereof. Alternatively, the vitamin is selected from the group consisting of niacinamide, tocopheryl nicotinate, pyroxidine, panthenol, vitamin E, vitamin E acetate, ascorbyl phosphates, ascorbyl glucoside, and mixtures thereof.

The composition may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide refers to both naturally occurring and synthesized peptides. In one embodiment, the peptides are di-, tri-, tetra-, penta-, and hexa-peptides, their salts, isomers, derivatives, and mixtures thereof. Examples of useful peptide derivatives include, but are not limited to, peptides derived from soy proteins, carnosine (beta-alanine-histidine), palmitoyl-lysine-threonine (pal-KT) and palmitoyl-lysine-threonine-threonine-lysine-serine (pal-KTTKS, available in a composition known as MATRIXYL®), palmitoyl-glycine-glutamine-proline-arginine (pal-GQPR, available in a composition known as RIGIN®), these three being available from Sederma, France, acetyl-glutamate-glutamate-methionine-glutamine-arginine-arginine (Ac-EEMQRR; Argireline®), and Cu-histidine-glycine-glycine (Cu-HGG, also known as IAMIN®). The compositions may comprise from about $1\times10^{-7}\%$ to about 20%, alternatively from about $1\times10^{-6}\%$ to about 10%, and alternatively from about $1\times10^{-5}\%$ to about 5% of the peptide.

The composition may comprise a sugar amine, also known as amino sugars, and their salts, isomers, tautomers and derivatives. Sugar amines can be synthetic or natural in origin and can be used as pure compounds or as mixtures of compounds (e.g., extracts from natural sources or mixtures of synthetic materials). For example, glucosamine is generally found in many shellfish and can also be derived from fungal sources. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). Other sugar amine compounds useful in skin care compositions include those described in U.S. Pat. No. 6,159,485, issued to Yu, et al. In one embodiment, the composition may comprise from about 0.01% to about 15%, alternatively from about 0.1% to about 10%, and alternatively from about 0.5% to about 5%, of the sugar amine.

The composition may comprise one or more sunscreen actives (or sunscreen agents) and/or ultraviolet light absorbers. Herein, suitable sunscreen actives include oil-soluble sunscreens, insoluble sunscreens, and water-soluble sunscreens. In certain embodiments, the composition may comprise from about 1% to about 20%, or, alternatively, from about 2% to about 10%, by weight of the composition, of the sunscreen active and/or ultraviolet light absorber. Exact amounts will vary depending upon the chosen sunscreen active and/or ultraviolet light absorber and the desired Sun Protection Factor (SPF), and are within the knowledge and judgment of one of skill in the art.

Non-limiting examples of suitable oil-soluble sunscreens include benzophenone-3, bis-ethylhexyloxyphenol methoxyphenyl triazine, butyl methoxydibenzoyl-methane, diethylamino hydroxy-benzoyl hexyl benzoate, drometrizole trisiloxane, ethylhexyl methoxy-cinnamate, ethylhexyl salicylate, ethylhexyl triazone, octocrylene, homosalate, polysilicone-15, and derivatives and mixtures thereof.

Non-limiting examples of suitable insoluble sunscreens include methylene bis-benzotriazolyl tetramethylbutyl-phenol, titanium dioxide, zinc cerium oxide, zinc oxide, and derivatives and mixtures thereof.

Non-limiting examples of suitable water-soluble sunscreens include phenylbenzimidazole sulfonic acid (PBSA), terephthalylidene dicamphor sulfonic acid, (Mexoryl™ SX), benzophenone-4, benzophenone-5, benzylidene camphor sulfonic acid, cinnamidopropyl-trimonium chloride, methoxycinnamido-propyl ethyldimonium chloride ether, disodium bisethylphenyl triaminotriazine stilbenedisulfonate, disodium distyrylbiphenyl disulfonate, disodium phenyl dibenzimidazole tetrasulfonate, methoxycinnamido-propyl hydroxysultaine, methoxycinnamido-propyl laurdimonium tosylate, PEG-25 PABA (p-aminobenzoic acid), polyquaternium-59, TEA-salicylate, and salts, derivatives and mixtures thereof.

The composition may comprise one or more compounds for regulating the production of skin oil, or sebum, and for improving the appearance of oily skin. Examples of suitable oil control agents include salicylic acid, dehydroacetic acid, benzoyl peroxide, vitamin B3 compounds (for example, niacinamide or tocopheryl nicotinate), their isomers, esters, salts and derivatives, and mixtures thereof. The compositions may comprise from about 0.0001% to about 15%, alternatively from about 0.01% to about 10%, alternatively from about 0.1% to about 5%, and alternatively from about 0.2% to about 2%, of an oil control agent.

The composition may comprise a tanning active. The compositions may comprise from about 0.1% to about 20%, from about 2% to about 7%, or, alternatively, from about 3% to about 6%, by weight of the composition, of a tanning active. A suitable tanning active includes dihydroxyacetone, which is also known as DHA or 1,3-dihydroxy-2-propanone.

The composition may comprise a safe and effective amount of one or more anti-acne actives. Examples of useful anti-acne actives include resorcinol, sulfur, salicylic acid, erythromycin, zinc, and benzoyl peroxide. Suitable anti-acne actives are described in further detail in U.S. Pat. No. 5,607,980. The composition may comprise a safe and effective amount of a desquamation active such as from about 0.01% to about 10%, from about 0.5% to about 5%, or, alternatively, from about 0.1% to about 2%, by weight of the composition. For example, the desquamation actives tend to improve the texture of the skin (e.g., smoothness). A suitable desquamation system may comprise sulfhydryl compounds and zwitterionic surfactants and is described in U.S. Pat. No. 5,681,852. Another suitable desquamation system may comprise salicylic acid and zwitterionic surfactants and is described in U.S. Pat. No. 5,652,228.

The composition may comprise a safe and effective amount of an anti-cellulite agent. Suitable agents may include, but are not limited to, xanthine compounds (e.g., caffeine, theophylline, theobromine, and aminophylline).

Skin care compositions may comprise a safe and effective amount of a chelating agent such as from about 0.1% to about 10% or from about 1% to about 5% of the composition. Exemplary chelators are disclosed in U.S. Pat. No. 5,487,884. A suitable chelator is furildioxime and derivatives.

The composition may comprise a skin lightening agent. The compositions may comprise from about 0.1% to about 10%, from about 0.2% to about 5%, or, alternatively, from about 0.5% to about 2%, by weight of the composition, of a skin lightening agent. Suitable skin lightening agents include kojic acid, arbutin, tranexamic acid, ascorbic acid and derivatives (e.g., magnesium ascorbyl phosphate or sodium ascorbyl phosphate or other salts of ascorbyl phosphate), ascorbyl glucoside, and the like. Other suitable skin lightening materials include undecylenoyl phenylalanine (Sepiwhite® from SEPPIC), aloesin, Actiwhite® (Cognis), and Emblica® (Rona).

The composition compositions may comprise a flavonoid. The flavonoid can be synthetic materials or obtained as extracts from natural sources, which also further may be derivatized. Examples of classes of suitable flavonoids are disclosed in U.S. Pat. No. 6,235,773.

The composition may comprise protease inhibitors including, but are not limited to, hexamidine compounds, vanillin acetate, menthyl anthranilate, soybean trypsin inhibitor, Bowman-Birk inhibitor, and mixtures thereof. Skin care compositions can include hexamidine compounds, its salts, and derivatives. As used herein, "hexaminide compound" means a compound having the formula:

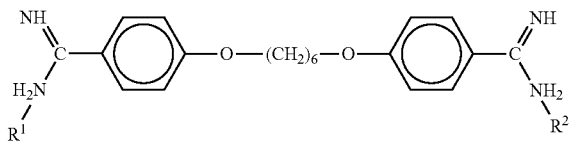

wherein $R^1$ and $R^2$ are optional or are organic acids (e.g., sulfonic acids, etc.). A particularly suitable hexamidine compound is hexamidine diisethionate.

The composition may other optional components such as non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobial or antifungal actives, and other useful skin care actives, which are described in further detail in U.S. application publication No. US 2006/0275237A1 and US 2004/0175347A1.

N. Color Cosmetics

The silicones of the present invention may also be used in cosmetic compositions, i.e., in products suitable for use in, on, or around the eyes, eyebrows, face, neck, chest, lips, hands, feet, or nails. Exemplary cosmetic products include eye liners, eye shadows, eyebrow pencils, mascaras, eye makeup removers, false eyelashes, under-eye concealers, eye creams, concealers, correctors, primers, blushes, bronzers, highlighters, shimmers, foundations, powders, sunscreens, brushes, face creams, lip primers, lip pencils, lipsticks, lip glosses, lip balms, lip stains, lip creams, and lotions. Examples of cosmetic products are found in U.S. Pat. No. 6,325,995 directed to an exemplary lip product; and U.S. Pat. No. 6,696,049 directed to an exemplary face product; and U.S. Pat. No. 6,503,495. The silicones of the present invention may be combined with materials commonly found in these compositions, such as alkyl dimethicone copolyols, polyols, hydrophilic skin treatment agents, carriers, thickening agent (such as solid waxes, gelling agents, inorganic thickeners, oil soluble polymers, fatty compounds, and mixtures thereof), pigments, film forming agents, preservatives, vitamins, etc. See U.S. Pat. No. 7,270,828 for examples.

O. Other Optional Components

The compositions of the present invention may contain also vitamins and amino acids such as: water soluble vitamins such as vitamin B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their salts and/or derivatives, water insoluble amino acids such as tyrosine, tryptamine, viscosity modifiers, dyes, nonvolatile solvents or diluents (water soluble and insoluble), pearlescent aids, foam boosters, additional surfactants or nonionic co-surfactants, pediculocides, pH adjusting agents, perfumes, preservatives, chelants, proteins, skin active agents, sunscreens, UV absorbers, vitamins, niacinamide, caffeine and minoxidil.

The compositions of the present invention may also contain pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names. The compositions of the present invention may also contain antimicrobial agents which are useful as cosmetic biocides. The compositions of the present invention may also contain chelating agents.

The compositions of the present invention may include oxidative dye compounds in the form of primary intermediates (developers) or couplers. The compounds suitable for use in the inventive compositions (including those optionally added), in so far as they are bases, may be used as free bases or in the form of their physiologically compatible salts with organic or inorganic acids, such as hydrochloric, hydrobromic, citric, acetic, lactic, succinic, tartaric, or sulfuric acids, or, in so far as they have aromatic hydroxyl groups, in the form of their salts with bases, such as alkali phenolates.

Developers

Suitable developers for use in the compositions described herein include, but are not limited to, p-phenylenediamine derivatives, e.g. benzene-1,4-diamine (commonly known as p-phenylenediamine); 2-chloro-benzene-1,4-diamine; N-phenyl-benzene-1,4-diamine; N-(2-ethoxyethyl)benzene-1,4-diamine; 2-[(4-amino-phenyl)-(2-hydroxy-ethyl)-amino]-ethanol (commonly known as N,N-bis(2-hydroxy-ethyl)-p-phenylenediamine); (2,5-diamino-phenyl)-methanol; 2-(2,5-diamino-phenyl)-ethanol; N-(4-aminophenyl)benzene-1,4-diamine; 2,6-dimethyl-benzene-1,4-diamine; 2-isopropyl-benzene-1,4-diamine; 1-[(4-aminophenyl)amino]-propan-2-ol; 2-propyl-benzene-1,4-diamine; 1,3-bis[(4-aminophenyl)(2-hydroxyethyl)amino]propan-2-ol; $N^4,N^4$,2-trimethylbenzene-1,4-diamine; 2-methoxy-benzene-1,4-diamine; 1-(2,5-diaminophenyl)ethanol; 1-(2,5-diaminophenyl)ethane-1,2-diol; 2,3-dimethyl-benzene-1,4-diamine; N-(4-amino-3-hydroxy-phenyl)-acetamide; 2,6-diethylbenzene-1,4-diamine; 2,5-dimethylbenzene-1,4-diamine; 2-thien-2-ylbenzene-1,4-diamine; 2-thien-3-ylbenzene-1,4-diamine; 2-pyridin-3-ylbenzene-1,4-diamine; 1,1'-biphenyl-2,5-diamine; 2-(methoxymethyl)benzene-1,4-diamine; 2-(aminomethyl)benzene-1,4-diamine; 2-(2,5-diaminophenoxy)ethanol; N-[2-(2,5-diaminophenoxy)ethyl]-acetamide; N,N-dimethylbenzene-1,4-diamine; N,N-diethylbenzene-1,4-diamine; N,N-dipropylbenzene-1,4-diamine; 2-[(4-aminophenyl)(ethyl)amino]ethanol; 2-[(4-amino-3-methyl-phenyl)-(2-hydroxy-ethyl)-amino]-ethanol; N-(2-methoxyethyl)-benzene-1,4-diamine; 3-[(4-aminophenyl)amino]propan-1-ol; 3-[(4-aminophenyl)-amino]propane-1,2-diol; N-{4-[(4-aminophenyl)amino]butyl}benzene-1,4-diamine; 2-[2-(2-{2-[(2,5-diaminophenyl)-oxy]ethoxy}ethoxy)ethoxy]benzene-1,4-diamine; 2,2'-[1,2-Ethanediyl-bis-(oxy-2,1-ethanediyloxy)]-bis-benzene-1,4-diamine; p-aminophenol derivatives such as: 4-amino-phenol (commonly known as p-aminophenol); 4-methylamino-phenol; 4-amino-3-methyl-phenol; 4-amino-2-hydroxymethyl-phenol; 4-amino-2-methyl-phenol; 4-amino-1-hydroxy-2-(2'-hydroxyethylaminomethyl)benzene; 4-amino-2-methoxymethyl-phenol;

5-amino-2-hydroxy-benzoic acid; 1-(5-amino-2-hydroxyphenyl)-ethane-1,2-diol; 4-amino-2-(2-hydroxy-ethyl)-phenol; 4-amino-3-(hydroxymethyl)phenol; 4-amino-3-fluorophenol; 4-amino-2-(aminomethyl)-phenol; 4-amino-2-fluoro-phenol; o-phenylenediamine derivatives such as: 3,4-Diaminobenzoic acid and salts thereof; o-aminophenol derivatives such as: 2-amino-phenol (commonly known as o-aminophenol); 2,4-diaminophenol; 2-amino-5-methyl-phenol; 2-amino-5-ethyl-phenol; 2-amino-6-methyl-phenol; N-(4-amino-3-hydroxy-phenyl)-acetamide; and 2-amino-4-methyl-phenol; and heterocyclic derivatives such as: pyrimidine-2,4,5,6-tetramine (commonly known as 2,4,5,6-tetraminopyrimidine); 1-methyl-1H-pyrazole-4,5-diamine; 2-(4,5-diamino-1H-pyrazol-1-yl)ethanol; $N^2,N^2$-dimethyl-pyridine-2,5-diamine; 2-[(3-amino-6-methoxypyridin-2-yl)amino]ethanol; 6-methoxy-$N^2$-methyl-pyridine-2,3-diamine; pyridine-2,5-diamine; 1-isopropyl-1H-pyrazole-4,5-diamine; 1-(4-methylbenzyl)-1H-pyrazole-4,5-diamine; 1-(benzyl)-1H-pyrazole-4,5-diamine; 1-(4-chlorobenzyl)-1H-pyrazole-4,5-diamine; pyrazolo[1,5-a]-pyrimidine-3,7-diamine; 5,6,7-trimethylpyrazolo[1,5-a]pyrimidin-3-ylamine hydrochloride; 7-methylpyrazolo[1,5-a]pyrimidin-3-ylamine hydrochloride; 2,5,6,7-teramethyl-pyrazolo[1,5-a]pyrimidin-3-ylamine hydrochloride; 5,7-di-tert-butylpyrazolo[1,5-a]pyrimidin-3-ylamine hydrochloride; 5,7-di-trifluoromethyl-pyrazolo[1,5-a]pyrimidin-3-ylamine hydrochloride; 2-methylpyrazolo[1,5-a]pyrimidin-3,7-diamine hydrochloride; 4-hydroxy-2,5,6-triaminopyrimidine; 2,3-diamino-6,7-dihydropyrazolo[1,2-a]pyrazol-1(5H)-one dimethosulfonate and salts thereof. Additional developers are selected from the group consisting of N-(3-furylmethyl)benzene-1,4-diamine; N-thiophen-3-ylmethyl-benzene-1,4-diamine; N-(2-furylmethyl)benzene-1,4-diamine; N-thiophen-2-ylmethyl-benzene-1,4-diamine; 3-(2,5-diamino-phenyl)-N-ethyl-acrylamide; 2-[3-(3-amino-phenylamino)-propenyl]-benzene-1,4-diamine; 2-[3-(4-amino-phenylamino)-propenyl]-benzene-1,4-diamine; 2-(6-methyl-pyridin-2-yl)-benzene-1,4-diamine; 2-pyridin-2-yl-benzene-1,4-diamine; 2-[3-(4-amino-phenylamino)-propenyl]-benzene-1,4-diamine; 2-[3-(3-amino-phenylamino)-propenyl]-benzene-1,4-diamine; 3-(2,5-diamino-phenyl)-N-ethyl-acrylamide; 2-thiazol-2-yl-benzene-1,4-diamine; 3'-fluoro-biphenyl-2,5-diamine; 2-propenyl-benzene-1,4-diamine; 2'-chloro-biphenyl-2,5-diamine; 4'-methoxy-biphenyl-2,5-diamine; N-(4-amino-benzyl)-benzene-1,4-diamine; N-[4-amino-2-(2-hydroxyethyl)-2H-pyrazol-3-yl]-3-(5-amino-2-hydroxy-phenyl)-acrylamide hydrochloride; 4-amino-2-propylaminomethyl-phenol; 4-amino-2-(isopropylamino-methyl)-phenol hydrochloride; 4-amino-2-[(2-hydroxy-5-nitro-phenylamino)-methyl]-phenol hydrochloride; 4-amino-2-(pyridin-3-ylaminomethyl)-phenol; 5-cyclobutylamino-2-methyl-phenol; 4,5-diamino-1-methyl-1H-pyrazole-3-carbonitrile; 3-methoxy-1-propyl-1H-pyrazole-4,5-diamine; 3-methoxy-1-(2-methoxyethyl)-1H-pyrazole-4,5-diamine; 1-(2-aminoethyl)-3-methoxy-1H-pyrazole-4,5-diamine; 8-methoxy-1,2,4,5-tetrahydropyrazolo[5,1-d][1,3,5]oxadiazepin-9-amine; 1-(2-hydroxyethyl)-3-methoxy-1H-pyrazol-4,5-diamine; 1-cyclohexyl-3-methoxy-1H-pyrazole-4,5-diamine; 6-methoxy-1-methyl-2,3-dihydro-1H-imidazo[1,2-b]pyrazol-7-amine; 2-methoxy-4,5,6,7-tetrahydropyrazolo[1,5-a]pyrimidin-3-amine; 3-methoxy-1-octyl-1H-pyrazole-4,5-diamine; 3-methoxy-1-pentyl-1H-pyrazole-4,5-diamine; 6-methoxy-2,3-dihydro-1H-imidazo[1,2-b]pyrazol-7-amine; 3-methoxy-$N^5,N^5$-dimethyl-1-propyl-1H-pyrazole-4,5-diamine; 1-hexyl-3-methoxy-1H-pyrazole-4,5-diamine; 1-butyl-3-methoxy-1H-pyrazole-4,5-diamine; 1-isopropyl-3-methoxy-1H-pyrazole-4,5-diamine; 1-ethyl-3-methoxy-1H-pyrazole-4,5-diamine; 3-methoxy-1-(4-methoxybenzyl)-1H-pyrazole-4,5-diamine; 3-methoxy-1-(pyridin-2-yl)-1H-pyrazole-4,5-diamine; 1-(4-ethylphenyl)-3-methoxy-1H-pyrazole-4,5-diamine; 3-methoxy-1-p-tolyl-1H-pyrazole-4,5-diamine; 3-cyano-1-(2-hydroxyethyl)-1H-pyrazole-4,5-diamine; 1-butyl-3-cyano-1H-pyrazole-4,5-diamine; 3-cyano-1-phenyl-1H-pyrazol-4,5-diamine; 3-cyano-1-hexyl-1H-pyrazol-4,5-diamine; 1-butyl-3-cyano-1H-pyrazol-4,5-diamine; 3-cyano-1-(4-methoxybenzyl)-1H-pyrazol-4,5-diamine; 3-cyano-1-isopropyl-1H-pyrazol-4,5-diamine; 1-cyclohexyl-3-fluoro-$N^5$-isopropyl-1H-pyrazole-4,5-diamine; 1-methyl-3-(trifluoromethoxy)-1H-pyrazole-4,5-diamine; 3-fluoro-1-octyl-1H-pyrazole-4,5-diamine; 3-chloro-1-hexyl-1H-pyrazole-4,5-diamine; 3-fluoro-1-(2-hydroxyethyl)-1H-pyrazol-4,5-diamine; 3-chloro-1-(2-hydroxyethyl)-1H-pyrazol-4,5-diamine; 3-chloro-1-(4-hydroxybutyl)-1H-pyrazol-4,5-diamine; 3-chloro-1-(pyridin-2-yl)-1H-pyrazole-4,5-diamine; 3-chloro-1-phenyl-1H-pyrazole-4,5-diamine; 3-chloro-1-ethyl-1H-pyrazole-4,5-diamine; 1-(3-methoxypropyl)-3-(methylsulfinyl)-1H-pyrazole-4,5-diamine; 1-(3-hydroxypropyl)-3-(methylsulfinyl)-1H-pyrazole-4,5-diamine; 1-(4-methoxybenzyl)-3-(methylsulfonyl)-1H-pyrazole-4,5-diamine; 1-methyl-3-(methylsulfonyl)-1H-pyrazole-4,5-diamine; and salts thereof.

In some embodiments, developers include but are not limited to: p-phenylenediamine derivatives such as: 2-methyl-benzene-1,4-diamine; benzene-1,4-diamine; 1-(2,5-diamino-phenyl)-ethanol; 2-(methoxymethyl)benzene-1,4-diamine; N-(2-methoxyethyl)benzene-1,4-diamine; 1-(2,5-diaminophenyl)ethane-1,2-diol; 1,3-bis(N-(2-hydroxyethyl)-N-(4-amino-phenyl)amino)-2-propanol; 2,2'-[1,2-ethanediyl-bis-(oxy-2,1-ethanediyloxy)]-bis-benzene-1,4-diamine; N,N-bis(2-hydroxyethyl)-p-phenylenediamine; and mixtures thereof; p-aminophenol derivatives such as: 4-amino-phenol; 4-methylamino-phenol; 4-amino-3-methyl-phenol; 4-amino-2-methoxymethyl-phenol; 1-(5-amino-2-hydroxy-phenyl)-ethane-1,2-diol; 4-amino-2-aminomethylphenol; 4-amino-1-hydroxy-2-(2'-hydroxyethylaminomethyl)benzene; 5-aminosalicylic acid and salts thereof; and mixtures thereof; o-phenylenediamine derivatives such as: 3,4-Diaminobenzoic acid and salts thereof; o-aminophenol derivatives such as: 2-amino-phenol; 2-amino-5-methyl-phenol; 2-amino-6-methyl-phenol; N-(4-amino-3-hydroxy-phenyl)-acetamide; 2-amino-4-methyl-phenol; 2-amino-5-ethyl-phenol; and mixtures thereof; and heterocyclic derivatives such as: pyrimidine-2,4,5,6-tetramine; 1-methyl-1H-pyrazole-4,5-diamine; 2-(4,5-diamino-1H-pyrazol-1-yl)ethanol; 1-(4-methylbenzyl)-1H-pyrazole-4,5-diamine; 1-(benzyl)-1H-pyrazole-4,5-diamine; $N^2,N^2$-dimethyl-pyridine-2,5-diamine; 4-Hydroxy-2,5,6-triaminopyrimidine; salts thereof; and mixtures thereof.

In certain embodiments, developers include: 2-methyl-benzene-1,4-diamine; 2-(methoxymethyl)benzene-1,4-diamine; benzene-1,4-diamine; N,N-bis(2-hydroxyethyl)-p-phenylenediamine; 4-amino-phenol; 4-methylamino-phenol; 4-amino-3-methyl-phenol; 2-amino-phenol; 2-amino-5-methyl-phenol; 2-amino-5-ethyl-phenol; 2-amino-6-methyl-phenol; 1-methyl-1H-pyrazole-4,5-diamine; 2-(4,5-diamino-1H-pyrazol-1-yl)ethanol; 2,5-diaminotoluene; 2,5-diaminophenylethyl alcohol; salts thereof; and mixtures thereof.

Couplers

Suitable couplers for use in the compositions described herein include, but are not limited to: phenols, resorcinols, naphthols, m-aminophenols, m-phenylenediamines, and heterocyclic compounds, and derivatives thereof such as: 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; benzene-1,4-diol; 2-methyl-benzene-1,3-diol; 7-amino-4-hydroxy-naphthalene-2-sulfonic acid; 1,2,3,4-tetrahydro-naphthalene-1,5-diol; 2-chloro-benzene-1,3-diol; 4-hydroxy-naphthalene-1-sulfonic acid; benzene-1,2,3-triol; naphthalene-2,3-diol; 5-chloro-2-methylbenzene-1,3-diol; 4,6-dichlorobenzene-1,3-diol; 2,3-dihydroxy-[1,4]naphthoquinone; and 1-Acetoxy-2-methylnaphthalene; m-phenylenediamines such as: 2,4-diaminophenol; benzene-1,3-diamine; 2-(2,4-diamino-phenoxy)-ethanol; 2-[(3-amino-phenyl)-(2-hydroxy-ethyl)-amino]-ethanol; 2-methyl-benzene-1,3-diamine; 2-[[2-(2,4-diamino-phenoxy)-ethyl]-(2-hydroxy-ethyl)-amino]-ethanol; 4-{3-[(2,4-diaminophenyl)oxy]propoxy}benzene-1,3-diamine; 2-(2,4-diamino-phenyl)-ethanol; 2-(3-amino-4-methoxy-phenylamino)-ethanol; 4-(2-amino-ethoxy)-benzene-1,3-diamine; (2,4-diamino-phenoxy)-acetic acid; 2-[2,4-diamino-5-(2-hydroxy-ethoxy)-phenoxy]-ethanol; 4-ethoxy-6-methyl-benzene-1,3-diamine; 2-(2,4-diamino-5-methyl-phenoxy)-ethanol; 4,6-dimethoxy-benzene-1,3-diamine; 2-[3-(2-hydroxy-ethylamino)-2-methyl-phenylamino]-ethanol; 3-(2,4-diamino-phenoxy)-propan-1-ol; N-[3-(dimethylamino)phenyl]urea; 4-methoxy-6-methyl-benzene-1,3-diamine; 4-fluoro-6-methylbenzene-1,3-diamine; 2-({3-[(2-hydroxyethyl)amino]-4,6-dimethoxyphenyl}-amino)ethanol; 3-(2,4-diaminophenoxy)-propane-1,2-diol; 2-[2-amino-4-(methylamino)-phenoxy]ethanol; 2-[(5-amino-2-ethoxy-phenyl)-(2-hydroxy-ethyl)-amino]-ethanol; 2-[(3-aminophenyl)amino]ethanol; 2,4-Diamino-5-(2'-hydroxyethyloxy)toluene; N,N-Dimethyl-3-ureidoaniline; N-(2-aminoethyl)benzene-1,3-diamine; 4-{[(2,4-diamino-phenyl)oxy]methoxy}-benzene-1,3-diamine; 1-methyl-2,6-bis(2-hydroxyethylamino)benzene; and 2,4-dimethoxybenzene-1,3-diamine; 1,3-bis-(2,4-diaminophenoxy)propane; 2-methyl-5-[(1-H-pyrrol-2-ylmethyl)-amino]-phenol; 5-[(furan-2-ylmethyl)-amino]-2-methyl-phenol; 5-isopropylamino-2-methyl-phenol; biphenyl-2,4,4'-triamine hydrochloride; 5-(4-amino-phenyl)aminomethyl-benzene-1,3-diamine hydrochloride; 5-phenylaminomethyl-benzene-1,3-diamine hydrochloride; 2-[4-amino-2-(3,5-diamino-benzylamino)-phenoxy]-ethanol hydrochloride; 5-(3-amino-phenyl)aminomethyl-benzene-1,3-diamine hydrochloride; N-(2-amino-benzyl)-benzene-1,3-diamine hydrochloride; N-furan-2-ylmethyl-benzene-1,3-diamine hydrochloride; 2-[(3-amino-phenylamino)-methyl]-phenol hydrochloride; 4-amino-2-propylaminomethyl-phenol; N-benzo[1,3]dioxol-5-ylmethyl-benzene-1,3-diamine hydrochloride; N-[4-amino-2-(2-hydroxy-ethyl)-2H-pyrazol-3-yl]-3-(5-amino-2-hydroxy-phenyl)-acrylamide; 4-thiophen-3-yl-benzene-1,3-diamine; 5-phenylaminomethyl-benzene-1,3-diamine hydrochloride; 5-(3-amino-phenyl)aminomethyl-benzene-1,3-diamine hydrochloride; 4-thiophen-3-yl-benzene-1,3-diamine; 2',4'-diamino-biphenyl-4-ol; 5-cyclobutylamino-2-methyl-phenol; 5-cyclobutylamino-2-methyl-phenol; 4-amino-2-(pyridin-3-ylaminomethyl)-phenol; 5-(3-amino-phenyl)aminomethyl-benzene-1,3-diamine hydrochloride; 5-allylaminomethyl-benzene-1,3-diamine hydrochloride; N-(4-amino-benzyl)-benzene-1,3-diamine hydrochloride; N-benzyl-benzene-1,3-diamine hydrochloride; 3-[(3-amino-phenylamino)-methyl]-phenol hydrochloride; N-(4-methoxy-benzyl)-benzene-1,3-diamine hydrochloride; N-thiophen-2-ylmethyl-benzene-1,3-diamine hydrochloride; 4-Amino-2-[(2-hydroxy-5-nitro-phenylamino)-methyl]-phenol; 2',4'-diamino-biphenyl-4-ol hydrochloride; biphenyl-2,4,4'-triamine; 5-(4-amino-phenyl)aminomethyl-benzene-1,3-diamine hydrochloride; 2-[4-amino-2-(3,5-diamino-benzylamino)-phenoxy]-ethanol hydrochloride; 5-allylaminomethyl-benzene-1,3-diamine hydrochloride; 5-(3-amino-phenyl)aminomethyl-benzene-1,3-diamine hydrochloride; N-(4-amino-benzyl)-benzene-1,3-diamine hydrochloride; N-benzyl-benzene-1,3-diamine hydrochloride; 3-[(3-amino-phenylamino)-methyl]-phenol hydrochloride; N-(2-amino-benzyl)-benzene-1,3-diamine hydrochloride; N-(4-methoxy-benzyl)-benzene-1,3-diamine hydrochloride; N-furan-2-ylmethyl-benzene-1,3-diamine hydrochloride; 2-[(3-amino-phenylamino)-methyl]-phenol hydrochloride; N-thiophen-2-ylmethyl-benzene-1,3-diamine hydrochloride; N-benzo[1,3]dioxol-5-ylmethyl-benzene-1,3-diamine hydrochloride; m-aminophenols such as: 3-amino-phenol; 2-(3-hydroxy-4-methyl-phenylamino)-acetamide; 2-(3-hydroxy-phenylamino)-acetamide; 5-amino-2-methyl-phenol; 3-amino-2,6-dimethylphenol; 5-(2-hydroxy-ethylamino)-2-methyl-phenol; 5-amino-2,4-dichlorophenol; 3-amino-2-methyl-phenol; 3-amino-2,6-dimethylphenol; 3-amino-2-chloro-6-methyl-phenol; 5-amino-2-(2-hydroxy-ethoxy)-phenol; 2-chloro-5-(2,2,2-trifluoroethylamino)-phenol; 5-amino-4-chloro-2-methyl-phenol; 3-cyclopentylamino-phenol; 5-[(2-hydroxyethyl)amino]-4-methoxy-2-methylphenol; 5-amino-4-methoxy-2-methylphenol; 3-(dimethylamino)phenol; 3-(diethylamino)phenol; 5-amino-4-fluoro-2-methylphenol; 5-amino-4-ethoxy-2-methylphenol; 3-amino-2,4-dichloro-phenol; 3-[(2-methoxyethyl)amino]phenol; 3-[(2-hydroxyethyl)amino]phenol; 5-amino-2-ethyl-phenol; 5-amino-2-methoxyphenol; 5-[(3-hydroxy-propyl)amino]-2-methylphenol; 3-[(3-hydroxy-2-methylphenyl)-amino]propane-1,2-diol; 3-[(2-hydroxyethyl)amino]-2-methylphenol; 2-methyl-5-[(1-H-pyrrol-2-ylmethyl)-amino]-phenol; 5-[(furan-2-ylmethyl)-amino]-2-methyl-phenol; 5-isopropylamino-2-methyl-phenol; 5-cyclobutylamino-2-methyl-phenol and heterocyclic derivatives such as: 3,4-dihydro-2H-1,4-benzoxazin-6-ol; 6-methoxyquinolin-8-amine; 4-methylpyridine-2,6-diol; 2,3-dihydro-1,4-benzodioxin-5-ol; 1,3-benzodioxol-5-ol; 2-(1,3-benzodioxol-5-ylamino)ethanol; 3,4-dimethylpyridine-2,6-diol; 5-chloropyridine-2,3-diol; 2,6-dimethoxypyridine-3,5-diamine; 1,3-benzodioxol-5-amine; 2-{[3,5-diamino-6-(2-hydroxy-ethoxy)-pyridin-2-yl]oxy}-ethanol; 1H-indol-4-ol; 5-amino-2,6-dimethoxypyridin-3-ol; 1H-indole-5,6-diol; 1H-indol-7-ol; 1H-indol-5-ol; 1H-indol-6-ol; 6-bromo-1,3-benzodioxol-5-ol; 2-aminopyridin-3-ol; pyridine-2,6-diamine; 3-[(3,5-diaminopyridin-2-yl)oxy]propane-1,2-diol; 5-[(3,5-diaminopyridin-2-yl)oxy]pentane-1,3-diol; indoline-5,6-diol; 3,5-dimethoxypyridine-2,6-diamine; 6-methoxypyridine-2,3-diamine; 3,4-dihydro-2H-1,4-benzoxazin-6-amine; 4-hydroxy-N-methylindole; 1H-5-methylpyrazol-5-one; 1-phenyl-3-methylpyrazol-5-one; 2,6-dimethylpyrazolo[1,5-b]-1,2,4-triazole; 2,6-dimethyl[3,2-c]-1,2,4-triazole; 6-methylpyrazolo-[1,5-a]benzimidazole; 2,6-dihydroxypyridine; 2,6-dihydroxy-3,4-dimethylpyridine; 5-methylpyrazolo[5,1-e]-1,2,3-triazole; 5-methyl-6-chloropyrazolo[5,1-e]-1,2,3-triazole; 5-phenylpyrazolo[5,1-e]-1,2,3-triazole and its addition salts; 1H-2,6-dimethylpyrazolo[1,5-b]-1,2,4-triazole tosylate; 7,8-dicyano-4-methylimidazolo-[3,2-a]imidazole; 2,7-dimethylpyrazolo[1,5-a]pyrimidin-5-one; 2,5-dimethylpyrazolo[1,5-a]pyrimidin-7-one; and 2-methyl-5-methoxymethyl-pyrazolo[1,5-a]pyrimidin-7-one; 6-hydroxybenzomorpholine; and 3-amino-2-methylamino-6-methoxypyridine; salts thereof; and mixtures thereof.

In some embodiments, couplers include but are not limited to: phenol, resorcinol, and naphthol derivatives such as: 2-amino-5-ethyl-phenol; naphthalene-1,7-diol; benzene-1,3-diol; 4-chlorobenzene-1,3-diol; naphthalen-1-ol; 2-methyl-naphthalen-1-ol; naphthalene-1,5-diol; naphthalene-2,7-diol; benzene-1,4-diol; 2-methyl-benzene-1,3-diol; and 2-isopropyl-5-methylphenol; 1,2,4-trihydroxybenzene; 1-acetoxy-2-methylnaphthalene; and mixtures thereof; m-phenylenediamine derivatives such as: benzene-1,3-diamine; 2-(2,4-diamino-phenoxy)-ethanol; 4-{3-[(2,4-diaminophenyl)oxy]propoxy}benzene-1,3-diamine; 2-(3-amino-4-methoxy-phenylamino)-ethanol; 2-[2,4-diamino-5-(2-hydroxy-ethoxy)-phenoxy]-ethanol; and 3-(2,4-diaminophenoxy)-propan-1-ol; 2,4-diamino-5-(2'-hydroxyethyloxy) toluene; N,N-dimethyl-3-ureidoaniline; 2,4-diamino-5-fluorotoluene; 1-methyl-2,6-bis(2-hydroxyethylamino) benzene; and mixtures thereof; m-aminophenol derivatives such as: 3-aminophenol; 5-amino-2-methyl-phenol; 3-amino-2,6-dimethylphenol; 5-(2-hydroxy-ethylamino)-2-methyl-phenol; and 3-amino-2-methyl-phenol; 1-hydroxy-3-amino-2,4-dichlorobenzene; 1,3-bis-(2,4-diaminophenoxy) propane; 1-hydroxy-2-methyl-5-amino-6-chlorobenzene; 5-Amino-4-chloro-2-methylphenol; and mixtures thereof; and heterocyclic derivatives such as: 3,4-dihydro-2H-1,4-benzoxazin-6-ol; 1,3-benzodioxol-5-ol; 1,3-benzodioxol-5-amine; 1H-indol-4-ol; 1H-indole-5,6-diol; 1H-indol-7-ol; 1H-indol-5-ol; 1H-indol-6-ol; pyridine-2,6-diamine; 2-aminopyridin-3-ol; 4-hydroxy-N-methylindole; 1H-5-methylpyrazol-5-one; 1-phenyl-3-methylpyrazol-5-one; 2,6-dimethylpyrazolo[1,5-b]-1,2,4-triazole; 2,6-dimethyl[3,2-c]-1,2,4-triazole; 6-methylpyrazolo-[1,5-a]benzimidazole; 2,6-dihydroxypyridine; 2,6-dihydroxy-3,4-dimethylpyridine; 6-hydroxybenzomorpholine; 2,6-dihydroxy-3,4-dimethylpyridine; 3,5-diamino-2,6-dimethoxypyridine; 3-amino-2-methylamino-6-methoxypyridine; salts thereof; and mixtures thereof.

In certain embodiments, couplers include: 2-amino-5-ethyl-phenol; benzene-1,3-diol; 4-chlorobenzene-1,3-diol; 4,6-dichlorobenzene-1,3-diol; 2-methyl-benzene-1,3-diol; 2-amino-4-(2'-hydroxyethyl)aminoanisole; 2,4-diaminobenzyl alcohol; 2,4-diaminophenylethyl alcohol; m-phenylenediamine; 5-amino-2-methyl-phenol; 3-amino-2,6-dimethylphenol; 2,4-diaminophenoxyethanol; 1-naphthol; 2-methyl-naphthol; 3-aminophenol; 3-amino-2-methylphenol; 4-hydroxy-1,2-methylenedioxybenzene; 4-amino-1,2-methylenedioxybenzene; 4-(2'-hydroxyethyl)amino-1,2-methylenedioxybenzene; 1-Methyl-2-hydroxy-4-(2'-hydroxyethyl)aminobenzene; 2,4-diaminophenetole; 2,4-diamino-5-methylphenetole; 4-hydroxyindole; 3-amino-5-hydroxy-2,6-dimethoxypyridine; and 3,5-diamino-2,6-dimethoxypyridine; benzene-1,3-diamine; 2-aminopyridin-3-ol; 1-phenyl-3-methylpyrazol-5-one; salts thereof; and mixtures thereof.

Additionally, in some embodiments, developers and couplers include 5-methoxymethyl-2-aminophenol; 5-ethyl-2-aminophenol; 5-phenyl-2-aminophenol; 5-cyanoethyl-2-aminophenol; salts thereof; and mixtures thereof.

Any of the developers and couplers described above may be combined to form a mixture of developers and couplers. The hair dye compositions of the present invention will generally comprise from about 0.001% to about 10% by weight of the dyeing composition of developer and coupler dyes. For example, compositions providing low intensity dyeing such as natural blond to light brown hair shades generally comprise from about 0.001% to about 5%, in some embodiments, from about 0.1% to about 2%, in certain embodiments, from about 0.2% to about 1% by weight of dyeing composition of developers and couplers. Darker shades such as browns and black typically comprise from 0.001% to about 10% by weight, in some embodiments, from about 0.05% to about 7% by weight, in certain embodiments, from about 1% to about 5% of developers and couplers. Developer compounds are generally used in approximately equimolar quantities with respect to coupler compounds. The developer compound may, however, be present in a greater or lesser quantity with respect to the coupler compound.

Direct Dyes

The inventive compositions may also comprise compatible direct dyes, in an amount sufficient to provide coloring, particularly with regard to intensity. Typically, such an amount will range from about 0.05% to about 4%, by weight of the dye composition. Suitable direct dyes include but are not limited to: Acid Yellow 1; Acid Orange 3; Disperse Red 17; Basic Brown 17; Acid Black 52; Acid Black 1; Disperse Violet 4; 4-nitro-o-phenylenediamine; 2-nitro-p-phenylenediamine; Picramic Acid; HC Red No. 13; 1,4-bis-(2'-hydroxyethyl)-amino-2-nitrobenzene; HC Yellow No. 5; HC Red No. 7; HC Blue No. 2; HC Yellow No. 4; HC Yellow No. 2; HC Orange No. 1; HC Red No. 1; 2-chloro-5-nitro-N-hydroxyethyl-p-phenylenediamine; HC Red No. 3; 4-amino-3-nitrophenol; 2-hydroxyethylamino-5-nitroanisole; 3-nitro-p-hydroxyethylaminophenol; 2-amino-3-nitrophenol; 6-nitro-o-toluidine; 3-methylamino-4-nitrophenoxyethanol; 2-nitro-5-glycerylmethylaniline; HC Yellow No. 11; HC Violet No. 1; HC Orange No. 2; HC Orange No. 3; HC Yellow No. 9; 4-nitrophenyl aminoethylurea; HC Red No. 10; HC Red No. 11; 2-hydroxyethyl picramic acid; HC Blue No. 12; HC Yellow No. 6; hydroxyethyl-2-nitro-p-toluidine; HC Yellow No. 12; HC Blue No. 10; HC Yellow No. 7; HC Yellow No. 10; HC Blue No. 9; N-ethyl-3-nitro PABA; 4-amino-2-nitrophenyl-amine-2'-carboxylic acid; 2-chloro-6-ethylamino-4-nitrophenol; 6-nitro-2,5-pyridinediamine; HC Violet No. 2; 2-amino-6-chloro-4-nitrophenol; 4-hydroxypropylamino-3-nitrophenol; HC Yellow No. 13; 1,2,3,4-tetrahydro-6-nitrochinoxalin; HC Red No. 14; HC Yellow No. 15; HC Yellow No. 14; 3-amino-6-methylamino-2-nitropyridine; 2,6-diamino-3-((pyridine-3-yl)azo)pyridine; Basic Red No. 118; Basic Orange No. 69; N-(2-nitro-4-aminophenyl)-allylamine; 4-[(4-amino-3-methylphenyl)(4-imino-3-methyl-2,5-cyclohexadien-1-ylidene)methyl]-2-methyl-benzeneamine-hydrochloride; 2-[[4-(dimethyl-amino)phenyl]azo]-1,3-dimethyl-1H-imidazolium chloride; 1-methyl-4-[(methylphenyl-hydrazono)methyl]-pyridinium, methyl sulfate; 2-[(4-aminophenyl)azo]-1,3-dimethyl-1H-imidazolium chloride; Basic Red 22; Basic Red 76; Basic Brown 16; Basic Yellow 57; 7-(2',4'-dimethyl-5'-sulfophenylazo)-5-sulfo-8-hydroxynaphthalene; Acid Orange 7; Acid Red 33; 1-(3'-nitro-5'-sulfo-6'-oxophenylazo)-oxo-naphthalene chromium complex; Acid Yellow 23; Acid Blue 9; Basic Violet 14; Basic Blue 7; Basic Blue 26; sodium salt of mixture of mono- & disulfonic acids (mainly the latter) of quinophthlanone or 2-quinolylindandione; Basic Red 2; Basic Blue 99; Disperse Red 15; Acid Violet 43; Disperse Violet 1; Acid Blue 62; Pigment Blue 15; Acid Black 132; Basic Yellow 29; Disperse Black 9; 1-(N-methylmorpholinium-propylamino)-4-hydroxy-anthraquinone methylsulfate; N,N-dimethyl-3-((4-(methylamino)-9,10-dioxo-9,10-dihydroanthracen-1-yl) amino)-N-propylpropan-1-aminium bromide, HC Blue No. 8; HC Red No. 8; HC Green No. 1; HC Red No. 9; 2-hydroxy-1,4-naphthoquinone; Acid Blue 199; Acid Blue 25; Acid Red 4; Henna Red; Indigo; Cochenille; HC Blue No. 14; Disperse Blue 23; Disperse Blue 3; Disperse Blue 377; Basic Red 51; Basic Orange 31; Basic Yellow 87; and mixtures thereof. Preferred direct dyes include but are not limited to: Disperse Black 9; HC Yellow 2; HC Yellow 4; HC Yellow 15; 4-nitro-o-phenylenediamine; 2-amino-6-chloro-4-nitrophenol; HC Red 3; Disperse Violet 1; HC Blue 2; Disperse Blue 3; Disperse Blue 377; Basic Red 51; Basic Orange 31; Basic Yellow 87; and mixtures thereof.

Oxidizing Agent

The inventive compositions may comprise an oxidizing agent, present in an amount sufficient to bleach melanin pigment in hair and/or cause formation of dye chromophores from oxidative dye precursors (including developers and/or couplers when present). Inorganic peroxygen materials capable of yielding hydrogen peroxide in an aqueous medium are preferred and include but are not limited to: hydrogen peroxide; inorganic alkali metal peroxides (e.g. sodium periodate and sodium peroxide); organic peroxides (e.g. urea peroxide, melamine peroxide); inorganic perhydrate salt bleaching compounds (e.g. alkali metal salts of perborates, percarbonates, perphosphates, persilicates, and persulphates, preferably sodium salts thereof), which may be incorporated as monohydrates, tetrahydrates, etc.; alkali metal bromates; enzymes; and mixtures thereof. In one embodiment, the oxidizing agents of the present invention are selected from percarbonates (such as sodium percarbonate, ammonium percarbonate and potassium percarbonate); and persulphates (such as sodium persulphate, ammonium persulphate, and potassium persulphate). In another embodiment, the oxidizing agents of the present invention are selected from sodium percarbonate and ammonium persulfate.

pH Modifiers and Buffering Agents

The inventive compositions may comprise a pH modifier and/or buffering agent in an amount that is sufficiently effective to adjust the pH of the composition to fall within a range from about 3 to about 13, in some embodiments from about 8 to about 12, and even from about 8 to about 11. In some embodiments, the pH range for the carbonate ion source as described herein below is from 8.5 to 9.5, preferably from 8 to 9. Suitable pH modifiers and/or buffering agents for use herein include, but are not limited to ammonia, alkanolamines such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, preferably sodium hydroxide and ammonium carbonate, and acidulents such as inorganic and inorganic acids, e.g., phosphoric acid, acetic acid, ascorbic acid, citric acid or tartaric acid, hydrochloric acid, and mixtures thereof.

Carbonate Ion Source

The compositions of the present invention may further comprise in an embodiment at least one source of peroxymonocarbonate ions, preferably formed in situ from a source of hydrogen peroxide and a carbonate ion source. According to the present invention the compositions thus also may comprise at least a source of carbonate ions or carbamate ions or hydrocarbonate ions or any mixture thereof. Any source of these ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Suitable sources of carbonate ions, carbamate and hydrocarbonate ions include sodium hydrogen carbonate, potassium hydrogen carbonate, ammonium carbamate and mixtures thereof.

Radical Scavenger System

The inventive compositions may comprise a radical scavenger, in a sufficient amount to reduce damage to the hair during an oxidative bleaching or coloring process. The radical scavenger is preferably selected such that it is not an identical species as the alkalizing agent. The radical scavenger is a species that can react with a carbonate radical to convert the carbonate radical by a series of fast reactions to a less reactive species. Suitable radical scavengers may be selected from the classes of alkanolamines, amino sugars, amino acids and mixtures thereof, and may include, but are not limited to: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan and potassium, sodium and ammonium salts of the above and mixtures thereof. Other suitable radical scavenger compounds include benzylamine, glutamic acid, imidazole, di-tert-butylhydroxytoluene, hydroquinone, catechol and mixtures thereof.

Chelants

The inventive composition may comprise chelants in an amount sufficient to reduce the amount of metals available to interact with formulation components, particularly oxidizing agents, more particularly peroxides. Suitable chelants for use herein include but are not limited to: diamine-N,N'-dipolyacid, monoamine monoamide-N,N'-dipolyacid, and N,N'-bis(2-hydroxybenzyl)ethylenediamine-N,N'-diacetic acid chelants (preferably EDDS (ethylenediaminedisuccinic acid)), carboxylic acids (preferably aminocarboxylic acids), phosphonic acids (preferably aminophosphonic acids) and polyphosphoric acids (in particular straight polyphosphoric acids), their salts and derivatives.

Foaming Agents

The inventive composition may be delivered in the form of a foam. Such an embodiment requires the use of a foaming agent, such as surfactants (e.g., anionic, non-ionic, cationic and amphoteric), proteins (e.g., enzymes), cellulosic materials, polymeric materials and mixtures thereof. Suitable polymeric materials include hydrophilic polymers, such as, agar-agar, polyvinyl alcohol, sodium alginate and sodium dodecyl sulphate-poly(ethylene oxide). A preferred polymeric material is a hydrophobically-modified alkali soluble emulsion polymer synthesized through an emulsion polymerization process from an acid/acrylate copolymer backbone and a monomer that connects the hydrophobic groups as side chains. An example of such a material is Aculyn™ 22, commercially available from Rohm Haas, which is synthesized from acrylic acid, acrylate esters and a steareth-20 methacrylate ester. Another preferred polymer is an anionic alkali-soluble polymer emulsion synthesized from acid and acrylate comonomers through emulsion polymerization. An example of such a material is Aculyn™ 33, commercially available from Rohm Haas. Other foaming agents include cetyl hydroxyethylcellulose, PEG 7M, hydroxypropyl methylcellulose, Carbomer and polyquaternium-55. Mixtures of these materials may be used.

As used herein "foam" means a hair colorant composition which after being passed through a manually-actuable, non-aerosol dispenser has a foam specific volume from about 6 to about 14 ml/g, such as about 7.5 ml/g to about 12 ml/g, or even from about 8 to about 10.5 ml/g.

Acceptable foam characteristics in hair colorant composition are exemplified by foam that holds its shape and stays in a consistent form. The minimum time for this is at least long enough to transfer from a user's hand to the desired location on the hair, e.g. the foam substantially maintains its shape for at least 15 seconds, for example at least 20, or at least 30 seconds. It could be longer if a quantity of foam, e.g. a bowl full by a hair dresser, is generated and spreading on the head only starts once the bowl full is readily made.

If foam collapses prematurely and becomes liquid-like (or some liquid is forming a puddle in the hand below the foam) any movement of the user's hand causes the foam to run, drip or otherwise move from the user's hand before the foam reaches the desired location and is considered undesirable.

The foam is suitable when formed when the composition is used with a manually-actable, non-aerosol dispenser where the composition is mixed with air such that the ratio of air to composition is from about 1:6 to about 1:15, from about 1:8 to about 1:12, or about 1:10.

A suitable manually-actuable, non-aerosol dispenser structure include the dimensions of the dip tube, dimensions of the air ingress into the mixing chamber, mixing chamber dimensions, including the ingress and egress orifices from the mixing chamber, dispensing channel dimensions, porous elements (such as screens or meshes) and dispensing head orifice.

Method of Making Shampoo Formulations

Any suitable method of making the shampoo of the present invention may be used. In one embodiment, undecyl-based surfactant is blended with the other components of the shampoo compositions, according to standard methods known in the art. The typical procedure used for a clarifying shampoo would be to combine the undecyl sulfate paste or undeceth sulfate paste or mixtures thereof with water, add the desired water soluble co-surfactant and finish the composition by the addition preservatives, pH control agents, perfume, and salts to obtain the target physical properties. If a water insoluble co-surfactant is desired the surfactant and water mixture can be heated to a suitable temperature to facilitate its incorporation. If a rheology modifier is desired it can be added to the surfactant mixture prior the finishing step.

In the case of conditioning shampoos, typically the surfactant paste is combined with the co-surfactant as above and diluted with water to a target level commensurate to achieving the final activity. Rheology modifiers can be added at this point followed by conditioning agents, e.g. sucrose polyesters, silicones or silicone emulsions or other oils, cationic polymers from polymer premixes, perfumes, pearlizing agents or opacifiers, perfumes, and preservatives. Appropriate mixing steps to insure homogeneity are used as needed. The product is finished by the addition of pH control agents, hydrotropes, and salts to the desired physical properties.

Method of Making Conditioner Formulations

The hair conditioners can be prepared by any conventional method well known in the art. They are suitably made as follows: deionized water is heated to 85° C. and cationic surfactants and high melting point fatty compounds are mixed in. If necessary, cationic surfactants and fatty alcohols can be pre-melted at 85° C. before addition to the water. The water is maintained at a temperature of about 85° C. until the components are homogenized, and no solids are observed. The mixture is then cooled to about 55° C. and maintained at this temperature, to form a gel matrix. Silicones, or a blend of silicones and a low viscosity fluid, or an aqueous dispersion of a silicone is added to the gel matrix. When included, poly alpha-olefin oils, polypropylene glycols, and/or polysorbates are also added to the gel matrix. When included, other additional components such as perfumes and preservatives are added with agitation. The gel matrix is maintained at about 50° C. during this time with constant stiffing to assure homogenization. After it is homogenized, it is cooled to room temperature. A triblender and/or mill can be used in each step, if necessary to disperse the materials.

Compact Formulations

The present invention can also be used in a compact hair care formulation. A compact formula is a formula which delivers the same benefit to the consumer at a lower usage level. Compact formulations and methods of making compact formulations are described in US Application Publication No 2009/0221463A1.

Adjunct Materials

While not essential for the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' agglomerate/particle. The precise nature of these additional components, and levels of incorporation thereof, will depend on the physical form of the composition and the nature of the operation for which it is to be used. Suitable adjunct materials include, but are not limited to, polymers, for example cationic polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' cleaning and fabric care compositions. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts is present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, B-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include manganese, iron and chromium. Suitable MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in U.S. Pat. No. 6,225,464.

Processes of Making

The compositions of the present invention can be formulated into any suitable form and prepared by any process chosen by the formulator, non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

In one aspect, a process for producing a composition, said composition being a consumer product, or even, in one aspect, a cleaning composition, fabric care composition and/or a personal care composition, said process comprising:
a) forming a microcapsule of selected permeability in accordance with a process disclosed in this specification; and
b) combing said microcapsules with one or more adjunct ingredients, is disclosed.

In one aspect of said process, said particles may be contained in a slurry that is combined with said adjunct.

In one aspect of said process, said slurry may comprise one or more processing aids, selected from the group consisting of water, aggregate inhibiting materials such as divalent salts; particle suspending polymers such as xanthan gum, guar gum, caboxy methyl cellulose.

In one aspect of said process, said particles may be contained in an agglomerate that is combined with said adjunct.

In one aspect of said process, said agglomerate may comprise materials selected from the group consisting of silicas, citric acid, sodium carbonate, sodium sulfate, sodium chloride, and binders such as sodium silicates, modified celluloses, polyethylene glycols, polyacrylates, polyacrylic acids, zeolites and mixtures thereof.

Any suitable method of making the shampoo of the present invention may be used. In one embodiment, undecyl-based surfactant is blended with the other components of the shampoo compositions, according to standard methods known in the art. The typical procedure used for a clarifying shampoo would be to combine the undecyl sulfate paste or undeceth sulfate paste or mixtures thereof with water, add the desired water soluble co-surfactant and finish the composition by the addition preservatives, pH control agents, perfume, and salts to obtain the target physical properties. If a water insoluble co-surfactant is desired the surfactant and water mixture can be heated to a suitable temperature to facilitate its incorporation. If a rheology modifier is desired it can be added to the surfactant mixture prior the finishing step.

In the case of conditioning shampoos, typically the surfactant paste is combined with the co-surfactant as above and diluted with water to a target level commensurate to achieving the final activity. Rheology modifiers can be added at this point followed by conditioning agents, e.g. sucrose polyesters, silicones or silicone emulsions or other oils, cationic polymers from polymer premixes, perfumes, pearlizing agents or opacifiers, perfumes, and preservatives. Appropriate mixing steps to insure homogeneity are used as needed. The product is finished by the addition of pH control agents, hydrotropes, and salts to the desired physical properties.

The hair conditioners can be prepared by any conventional method well known in the art. They are suitably made as follows: deionized water is heated to 85° C. and cationic surfactants and high melting point fatty compounds are mixed in. If necessary, cationic surfactants and fatty alcohols can be pre-melted at 85° C. before addition to the water. The water is maintained at a temperature of about 85° C. until the components are homogenized, and no solids are observed. The mixture is then cooled to about 55° C. and maintained at this temperature, to form a gel matrix. Silicones, or a blend of silicones and a low viscosity fluid, or an aqueous dispersion of a silicone are added to the gel matrix. When included, poly alpha-olefin oils, polypropylene glycols, and/or polysorbates are also added to the gel matrix. When included, other additional components such as perfumes and preservatives are added with agitation. The gel matrix is maintained at about 50° C. during this time with constant stiffing to assure homogenization. After it is homogenized, it is cooled to room temperature. A triblender and/or mill can be used in each step, if necessary to disperse the materials.

Method of Use

In one aspect, a method of treating and/or cleaning a situs, is disclosed. Said method may comprise optionally washing and/or rinsing said situs; contacting said situs with any single or combination of compositions disclosed in the present specification; and optionally washing and/or rinsing said situs. Typically at least a portion of the situs is contacted with an embodiment of Applicants' composition, in neat form or diluted in a liquor, for example, a wash liquor. For purposes of the present invention, washing includes but is not limited to, scrubbing, and mechanical agitation. If the situs comprises a fabric it may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

In one aspect, a situs treated in accordance with such compositions, for example by the aforementioned method is disclosed.

Test Methods

It is understood that the test methods that are disclosed in the Test Methods Section of the present application should be used to determine the respective values of the parameters of Applicants' invention as such invention is described and claimed herein.

(1) Median Particle Size

Particle size is measured using an Accusizer 780A, made by Particle Sizing Systems, Santa Barbara Calif. The instrument is calibrated from 0 to 300µ using Duke particle size standards. Samples for particle size evaluation are prepared by diluting about 1 g of capsule slurry in about 5 g of de-ionized water and further diluting about 1 g of this solution in about 25 g of water.

About 1 g of the most dilute sample is added to the Accusizer and the testing initiated, using the autodilution feature. The Accusizer should be reading in excess of 9200 counts/second. If the counts are less than 9200 additional sample should be added. The accusizer will dilute the test sample until 9200 counts/second and initiate the evaluation. After 2 minutes of testing the Accusizer will display the results, including volume-weighted median size.

The broadness index can be calculated by determining the particle size at which 95% of the cumulative particle volume is exceeded (95% size), the particle size at which 5% of the cumulative particle volume is exceeded (5% size), and the median volume-weighted particle size (50% size—50% of the particle volume both above and below this size). Broadness Index (5)=((95% size)−(5% size)/50% size).

(2) Fracture Strength Test Method a.) Place 1 gram of particles in 1 liter of distilled deionized (DI) water.

b.) Permit the particles to remain in the DI water for 10 minutes and then recover the particles by filtration, using a 60 mL syringe filter, 1.2 micron nitrocellulose filter (Millipore, 25 mm diameter).

c.) Determine the rupture force of 50 individual particles. The rupture force of a particle is determined using the procedure given in Zhang, Z.; Sun, G; "Mechanical Properties of Melamine-Formaldehyde microcapsules," J. Microencapsulation, vol 18, no. 5, pages 593-602, 2001. Then calculate the fracture strength of each particle by dividing the rupture force (in Newtons) by the cross-sectional area of the respective spherical particle ($\pi r^2$, where r is the radius of the particle before compression), said cross-sectional area being determined as follows: measuring the particle size of each individual particle using the experimental apparatus and method of Zhang, Z.; Sun, G; "Mechanical Properties of Melamine-Formaldehyde microcapsules," J. Microencapsulation, vol 18, no. 5, pages 593-602, 2001.

d.) Use the 50 independent measurements from c.) above, and calculate the percentage of particles having a fracture strength within the claimed range fracture strength range.

(3) Procedure for Determination of Zeta Potential

Supplies needed:

Disposable 10 mL syringes 1 millimolar solution of NaCl/deionized water

Transfer pipets

Syringe filter with 25 mm/30 um filter paper

Equipment: Malvern Zetasizer, Malvern Instruments Ltd. Model DTS 5300

Procedure a) Rinse Malvern with deionized water by filling a syringe and inserting the tip into the inlet valve. Repeat for a total of 3 rinses with water.
b) Rinse again, using 1 millimolar solution of NaCL/$H_2O$. Repeat 3 times.
c) Prepare sample by weighing out 20 g NaCl solution into a disposable beaker. Add 2 drops of capsules (for 20 um size capsules—larger capsules add addition drops). Swirl to mix and draw up a syringe-full. Assemble syringe filter with 30 um paper and filter the capsule solution into another disposable beaker. Using a clean syringe, draw up filtered solution and inject into Malvern.
d) Record data generated by Malvern Zetasizer. Five readings are made per prepared sample. Rinse instrument between samples. Record values of KCps, Mobility, and Width.

(4) Procedure for Capsule Retention

Sample Preparation

Substrate Sample: A sample of the substrate for evaluation (typically a fabric), is placed over the inner hoop of an embroidery hoop. The outer hoop is placed over the sample and the inner hoop, the outer hoop is tightened partially, the substrate is pulled tight in the hoop set by pulling the substrate edges, and the outer hoop is fully tightened to securely hold the substrate sample. Excess sample is cut from the edges of the hoop and discarded. The substrate is chosen to be cotton fabric, 250 thread count.

Capsule Retention Bath: The capsule retention test is done using a 2000 mL glass beaker as the bath in which the substrate sample is submerged. The beaker is filled to about 1500 mL for all testing. The substrate sample, suspended on an embroidery hoop is placed into the beaker, with the top of the sample just below the liquid level and the bottom of the sample just above a magnetic stir bar that is run to keep movement in the fluid.

Sample Pre-Rinse: A substrate sample is suspended in de-ionized water in the capsule retention bath for 10 minutes to rinse away any fiber fragments, dust, dirt, or water-soluble surface treatments that may exist on the substrate surface. After 10 minutes in the retention bath, the sample is removed and air-dried for 10 minutes.

Microcapsule Retention: Microcapsules are added to a fresh 1500 mL of de-ionized for the microcapsule retention test. The total weight of microcapsules (dry basis) is about 50% of the substrate weight (0.65 g capsules, 1.25 g substrate). The substrate is re-suspended in the retention bath for another 10 minutes. The sample is removed, allowed to dry on the hoop for about 1 hour and is then removed and allowed to air-dry at least 4 hours total.

Extraction Samples: After the retention sample has been air-dried, 2-1" by 3.125" samples are cut from it, using a steel template and razor blade. This provides replicate test samples for the subsequent extraction testing.

ISTD (internal standard) Solution: 1 mg/ml Dibutyl Phthalate (DBP)/Hexane (HPLC grade)

For 250 ml's: Weigh a little more than 250 mgs of DBP into a small beaker and transfer to a 250 ml volumetric rinsing the beaker thoroughly. Fill to line with hexane.

ISTD Solution: 1 mg/ml Dibutyl Phthalate (DBP)/EtOH (Reagent grade)

For 250 ml's: Weigh a little more than 250 mgs of DBP into a small beaker and transfer to a 250 ml volumetric rinsing the beaker thoroughly. Fill to line with EtOH.

Instrumentation:

HP5890 GC connected to HP Chem Station Software

Column: 5 m×0.32 mm id with 1 um DBP-1 liquid phase

Temp: 50 deg for 1 minute then heat to 320 deg @ 15 deg/min

Injector: 275 deg C., Detector: 325 deg C.

2 ul injection

Procedure

1. Place samples in a 20 ml disposable scintillation vial.
2. Add 15 mL of the Hexane ISTD solution, tightly cap and allow to sit with periodic agitation for 30 minutes standing so the solvent covers the sample.
3. After 30 minutes, transfer a small amount of the Hexane extraction solution to an auto-sampler vial, leaving sample in the vial and allowing it to dry.
4. Add 15 mL of the EtOH ISTD solution to the vials containing the sample and tightly cap.
5. Place the vials in a water bath set at 70° C. for 30 minutes with periodic agitation.
6. After 30 minutes, remove the vials from the water bath and allow them to cool to room temperature, standing so that the solvent covers the sample.
7. Transfer a small amount of the EtOH extraction solution to an auto-sampler vial.

Calculations

For the Standard Solution:

1. Subtract the area count for the internal standard peak from the total area count.

For the Hexane and EtOH extractions:

1. Subtract the area counts for the internal standard peak from the total area counts.
2. Calculate the mg of oil using the following formula $$\frac{\text{Area Count for extraction}}{\text{Area Count for } Std.\ Sol^n} \times Conc.\ \text{Of Oil } for\ Std.\ Sol^n$$

3. Add the mg of oil from the Hexane extraction and EtOH extraction to obtain the total mg of oil.
4. Calculate the % oil released using the following formula $$\frac{\text{mg of Oil from Hexane Extraction}}{\text{Total mg of Oil}} \times 100$$

Preparation of Perfume Oil Standards

Three perfume oil standards should be prepared for GC analysis with the coated sample extractions.

Solution 1

1. Using a disposable Pasteur pipette, weight one (1) drop of the desired perfume oil in a 20 ml disposable scintillation vial.
2. Add 15 mL of the Hexane ISTD solution to the vial, cap and shake vigorously to mix.
3. Record the mg of oil/15 ml.

Example, one drop of perfume oil weighs 14.0 mg. The concentration for this standard solution would be 14 mg/15 ml.

4. Transfer a small amount of the standard solution to an auto-sampler vial and cap for GC analysis.

Solution 2
1. Transfer 5 ml of Standard Solution 1 to a new 20 ml disposable scintillation vial.
2. Add 5 ml of the Hexane ISTD solution to the vial, cap and shake vigorously to mix.
3. Record the mg of oil/15 ml.
   Example, the concentration for this standard solution would be 7 mg/15 ml.
4. Transfer a small amount of the standard solution to an auto-sampler vial and cap for GC analysis.

Solution 3
1. Transfer 1 ml of Standard Solution 1 to a new 20 ml disposable scintillation vial.
2. Add 9 ml of the Hexane ISTD solution to the vial, cap and shake vigorously to mix.
3. Record the mg of oil/15 ml.
   Example, the concentration for this standard solution would be 1.4 mg/15 ml.
4. Transfer a small amount of the standard solution to an auto-sampler vial and cap for GC analysis.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

Preparation of Oil Phases and Pre-Reaction of Wall Material

A first oil phase, consisting of 50 g cedar oil, 0.65 g TBAEMA, and 0.52 g Beta-C, is mixed for about 1 hour before the addition of 26 g CN997. The solution is allowed to mix until needed later in the batch.

A second oil solution consisting of 200 g of cedar oil, 1.56 g Vazo-52 and 0.52 g Vazo-67 is added to a jacketed steel reactor. The reactor is held at 35° C., and the oil solution is mixed at 1000 rpm with a 2" 4-tip flat blade mixer. A nitrogen blanket is applied to the reactor at a rate of 300 cc/min. The solution is heated to 75° C. in 45 minutes and held at 75° C. for 35 minutes, before cooling to 55° C. in 75 minutes. At 55° C., the first oil phase is added, and the combined oils are mixed for another 70 minutes at 55° C.

Water Phase Preparation

A water phase, containing 30 g of Colloid 351, 1.1 g 20% NaOH, 600 g water, and 1.56 g Vazo-68WSP, is prepared and mixed until the Vazo is dissolved. The water-phase pH is measured and the solution mixed until needed for batch preparation. The water phase pH for this batch is 4.58.

Capsule Batch Preparation

Once the oil phase temperature has decreased to 55° C., mixing is stopped and the water phase is added to the batch via funnel (to prevent premature mixing of the phases). Mixing is restarted at an appropriate speed to produce an emulsion with the desired size characteristics. In this particular case, mixing is done at 3000 rpm for 20 minutes and 2000 rpm for 40 minutes.

When milling is completed, mixing is done with a 3" propeller run at about 400 rpm. The batch is held at 55° C. for another 45 minutes, then the temperature is increased to 75° C. in 30 minutes, held at 75° C. for 4 hours, increased to 90° C. in 30 minutes, and held at 90° C. for 8 hours. The batch is allowed to cool to room temperature at the completion of the heating cycle. The finished batch has a volume-weighted median size of 12.2µ.

Examples 2 to 25 in Table 1 are similarly prepared. Batch preparation methods are similar to those described in Example 1 with the exceptions stated in Table 1. Water phase pH is adjusted up or down as necessary using either 20% NaOH or concentrated HCl. For examples 6 and 7, milling is continued throughout the batch due to emulsion instability during capsule wall formation. Example 15 and 16 are identical capsules, but for Example 16 the capsule batch pH is adjusted to pH 4. Examples 19 and 20 are similar. In Example 20, the capsule retention study conditions are first adjusted to pH 4. Example 25 is a melamine-formaldehyde wall capsule, shown for comparative purposes.

Capsule Test Data

Capsule test data are shown in Table 1. The table includes capsule leakage data (free-oil, and 4-week hexane leakage), Zeta potential for each batch (a measure of capsule surface charge), and a measure of relative capsule retention.

The abbreviations correspond to the following materials:

|  | Company/City |  |
|---|---|---|
| CN975 | Sartomer Company, Exton, PA | Hexafunctional Aromatic Urethane Acrylate Oligomer |
| CN997 | Sartomer Company, Exton, PA | Hexafunctional Aromatic Urethane Acrylate Oligomer |
| Colloid 351 | Rhone-Poulenc, Cedex, France | Copolymer of 92% Polyacrylic Acid/8% Butyl Acrylate |
| TBAEMA |  | Tertiarybutyl Aminoethyl Methacrylate |
| Vazo-52 | DuPont, Wilmington, DE | 2,2'-Azobis (2,4-Dimethylvaleronitrile) |
| Vazo-67 | DuPont, Wilmington, DE | 2,2'-Azobis (2-Methylbutyronitrile) |
| Vazo-68WSP | DuPont, Wilmington, DE | 4,4'-Azobis (4-Cyanovaleric Acid) |
| Irgacure 651 | CIBA, Tarrytown, NY | 2,2-Dimethoxy-1,2-Diphenylethan-1-one |
| Darocure 1173 | CIBA, Tarrytown, NY | 2-Hydroxy-2-Methyl-1-Phenyl-Propane-1-one |
| Beta-C | Bimax, Glen Rock, PA | Beta-carboxyethyl acrylate |
| Brij-700 | Sigma Aldrick, St. Louis, MO | Polyoxyethylene stearyl ether |
| Celvol 540 | Celanese, Dallas, TX | Polyvinyl alcohol |
| PVA |  |  |

TABLE 1

| Ex. | Batch | Emulsifier | Emlsifier Level (% of core) | Wall Material | Wall Base | Wall Acid | Water Phase pH | Capsule Size (micron) | Free-Oil (%) | 4-Wk Hexane (mg/ml) | Zeta Potential (mV) | Capsule Retention (mg oil) |
|---|---|---|---|---|---|---|---|---|---|---|---|---|
| 2 | TAS 1008081 | Colloid 351 | 3.0 | CN997 | TBAEMA | Beta-C | 4.6 | 12.2 | 0.35 | 7.34 | −57 | 0.3 |
| 3 | TAS 1009081 | Celvol 540 PVA | 3.0 | CN997 | TBAEMA | Beta-C | 4.5 | 9.9 | 0.07 | 2.79 | −6 | 2.1 |
| 4 | TAS 1010081 | Celvol 540 PVA | 3.0 | CN997 | TBAEMA | HCl | 4.5 | 11.7 | 0.11 | 2.47 | −2 | 2.4 |
| 5 | TAS 1013081 | Celvol 540 PVA | 3.0 | CN997 | NaOH | Beta-C | 4.5 | 10.8 | 0.11 | 2.55 | −3 | 1.2 |
| 6 | TAS 1030081 | Brij-700 | 3.0 | CN997 | TBAEMA | Beta-C | 4.5 | 25.9 | 14.39 | 9.63 | −4 | 1.2 |
| 7 | TAS 1105081 | Dodecyltrimethyl ammonium Chloride | 3.0 | CN997 | TBAEMA | Beta-C | 4.4 | 13.5 | 9.20 | 16.90 | 13 | 4.0 |
| 8 | TAS 1201081 | Poly(ethyleneimine) $M_w$: 750K | 3.0 | CN997 | TBAEMA | Beta-C | 9.4 | 15.9 | 0.07 | 0.45 | 18 | 8.1 |
| 9 | TAS 1205082 | Poly(ethyleneimine) $M_w$: 750K | 3.0 | CN997 | TBAEMA | Beta-C | 8.0 | 19.0 | 0.02 | 0.39 | 53 | 8.3 |
| 10 | TAS 1208081 | Poly(ethyleneimine) $M_w$: 750K | 3.0 | CN997 | TBAEMA | Beta-C | 11.1 | 22.8 | 0.03 | 0.32 | −4 | 3.4 |
| 11 | TAS 1211081 | Poly(ethyleneimine) $M_w$: 750K | 3.0 | CN997 | TBAEMA | HCl | 8.0 | 23.9 | 0.10 | 0.38 | 52 | 7.5 |
| 12 | TAS 1215081 | Poly(ethyleneimine) $M_w$: 750K | 3.0 | CN997 | TBAEMA | HCl | 9.5 | 31.9 | 0.13 | 0.40 | 27 | 10.4 |
| 13 | TAS 1216081 | Poly(ethyleneimine) $M_w$: 750K | 3.0 | CN997 | TBAEMA | HCl | 6.6 | 29.8 | 1.69 | 0.58 | 41 | 10.5 |
| 14 | TAS 1219081 | Poly(ethyleneimine) $M_w$: 750K | 0.6 | CN997 | TBAEMA | HCl | 11.4 | 31.5 | 0.13 | 0.51 | −28 | 5.5 |
| 15 | TAS 1230081 | Poly(ethyleneimine) $M_w$: 750K | 3.0 | CN975 | TBAEMA | HCl | 9.8 | 30.1 | 0.06 | | 31 | 12.6 |
| 16 | TAS 1230081 (B) | Poly(ethyleneimine) $M_w$: 750K | 3.0 | CN975 | TBAEMA | HCl | 9.8 (4.0) | 30.1 | 0.09 | | 51 | 7.1 |
| 17 | TAS 0106091 | Poly(ethyleneimine) $M_w$: 25K | 3.0 | CN975 | TBAEMA | HCl | 10.0 | 22.2 | 0.01 | 0.29 | 18 | 8.2 |
| 18 | TAS 0107091 | Poly(ethyleneimine) $M_w$: 25K | 3.0 | CN975 | NaOH | Beta-C | 10.0 | 22.8 | 0.01 | 0.31 | 12 | 6.4 |
| 19 | TAS 0112091 | Poly(ethyleneimine) $M_w$: 25K | 3.0 | CN975 | TBAEMA | HCl | 8.5 | 19.3 | 0.01 | | 65 | 8.0 |
| 20 | TAS 0112091 (B) | Poly(ethyleneimine) $M_w$: 25K | 3.0 | CN975 | TBAEMA | HCl | 8.5 (3.0) | 19.3 | 0.01 | 0.40 | n/a | 4.4 |
| 21 | TAS 0113091 | Poly(ethyleneimine) $M_w$: 25K | 3.0 | CN975 | NaOH | Beta-C | 8.5 | 23.2 | 0.01 | 0.38 | 59 | 12.1 |
| 22 | TAS 0115091 | Poly(ethyleneimine) $M_w$: 25K | 3.0 | CN975 | TBAEMA | Beta-C | 10.0 | 15.8 | 0.02 | | 22 | 5.0 |
| 23 | TAS 0116091 | Poly(ethyleneimine) $M_w$: 25K | 3.0 | CN975 | TBAEMA | Beta-C | 8.5 | 23.8 | 0.02 | | 63 | 7.4 |
| 24 | TAS 0120091 | Poly(ethyleneimine) $M_w$: 2K | 3.0 | CN975 | NaOH | Beta-C | 10.1 | 32.3 | 0.03 | | −3 | 4.5 |
| 25 | PS 020309 | Colloid 351 | | Melamine | n/a | n/a | | 15.1 | | | −57 | 0.6 |

In Table 1 capsule retention on cotton fiber is usefully at least 1 mg oil determined following the capsule retention procedure set forth herein. The invention makes possible capsule retention values of at least 1 mg oil, or even at least 4 mg oil, or even at least 8 mg oil, or even at least 10 mg oil.

Example 26

Microcapsules in Leave-on-Conditioner

Selected microcapsules from the above examples are formulated into a leave-on-conditioner formulation as follows: to 98.0 grams of leave-on-conditioner (with a typical formulation given below) is added an appropriate amount of microcapsule slurry of examples 1 through 24, to deliver an encapsulated oil usage level of 0.5 wt %. The microcapsules are added on top of the conditioner formulation, then the contents are mixed using a SpeedMixer by Hauschild DAC 400FVZ, at 1000 RPM for 1 minute.

A typical composition of a leave-on conditioner formulation is given in the following table:

| Components | Ex. II (LOT) (%) |
|---|---|
| Premix | |
| Aminosilicone | — |
| PDMS | 1.0-1.5 |
| Gel matrix carrier | |
| Behenyl trimethyl ammonium chloride | — |
| Stearamidopropyldimethylamine (SAPDMA), C18 | 0.60-0.8 |

-continued

| Components | Ex. II (LOT) (%) |
|---|---|
| DTDMAC, C18 (Quaternium-18) | 0.45-0.6 |
| Citric Acid (anhydrous) | 0.10-0.25 |
| Cetyl alcohol | 0.80-1.0 |
| Stearyl alcohol | 0.54-1.0 |
| Deionized Water | Balance |
| Polymers | |
| Hydroxyethylcellulose (HEC) | 0.15-0.50 |
| PEG-2M (Polyox WAR N-10) | 0.30-0.60 |
| Fragrance Microcapsules - Example 3 | 1.0-1.4 |
| Preservatives | 0.40-0.60 |

Example 27

Microcapsules in Shampoo

A subset of the capsules from the above examples is formulated into a rinse-off Shampoo formulation as follows: to 90.0 grams of shampoo formulation (with a typical formulation given below) is added an appropriate amount of microcapsule slurry of examples 1 through 24, to deliver an encapsulated oil usage level of 0.5 wt %. The microcapsules and water are added on top of the shampoo formulation, then the contents are mixed using a SpeedMixer by Hauschild DAC 400FVZ mixer, at 1850 RPM for 1 minute.

Typical composition of shampoo formulations are given in the examples below.

| Ingredient | EXAMPLE COMPOSITION | | |
|---|---|---|---|
| | I | II | III |
| Water | q.s. | q.s. | q.s. |
| Polyquaternium 76[1] | 2.50 | — | — |
| Guar, Hydroxylpropyl Trimonium Chloride[2] | — | 0.25 | — |
| Polyquaterium 6[3] | — | — | 0.79 |
| Sodium Laureth Sulfate (SLE3S)[4] | 21.43 | 21.43 | 21.43 |
| Sodium Lauryl Sulfate (SLS)[5] | 20.69 | 20.69 | 20.69 |
| Silicone[6] | 0.75 | 1.00 | 0.5 |
| Cocoamidopropyl Betaine[7] | 3.33 | 3.33 | 3.33 |
| Cocoamide MEA[8] | 1.0 | 1.0 | 1.0 |
| Ethylene Glycol Distearate[9] | 1.50 | 1.50 | 1.50 |
| Sodium Chloride[10] | 0.25 | 0.25 | 0.25 |
| Fragrance | 0.70 | 0.70 | 0.70 |
| Fragrance Microcapsule of Example 3 | 1.2 | 1.2 | 1.2 |
| Preservatives, pH adjusters | Up to 1% | Up to 1% | Up to 1% |

[1]Mirapol AT-1, Copolymer of Acrylamide(AM) and TRIQUAT, MW = 1,000,000; CD = 1.6 meq./gram; 10% active; Supplier Rhodia
[2]Jaguar C500, MW - 500,000, CD = 0.7, supplier Rhodia
[3]Mirapol 100S, 31.5% active, supplier Rhodia
[4]Sodium Laureth Sulfate, 28% active, supplier: P&G
[5]Sodium Lauryl Sulfate, 29% active supplier: P&G
[6]Glycidol Silicone VC2231-193C
[7]Tegobetaine F-B, 30% active supplier: Goldschmidt Chemicals
[8]Monamid CMA, 85% active supplier Goldschmidt Chemical
[9]Ethylene Glycol Distearate, EGDS Pure, supplier Goldschmidt Chemical
[10]Sodium Chloride USP (food grade), supplier Morton; note that salt is an adjustable ingredient, higher or lower levels may be added to achieve target viscosity.

| Ingredient | EXAMPLE COMPOSITION | | |
|---|---|---|---|
| | IV | V | VI |
| Water | q.s. | q.s. | q.s. |
| Silicone A[1] | 1.0 | — | — |
| Silicone B[2] | — | 0.5 | — |
| Silicone C[3] | — | — | 0.5 |
| Cyclopentasiloxane[4] | — | 0.61 | 1.5 |
| Behenyl trimethyl ammonium chloride[5] | 2.25 | 2.25 | 2.25 |
| Isopropyl alcohol | 0.60 | 0.60 | 0.60 |
| Cetyl alcohol[6] | 1.86 | 1.86 | 1.86 |
| Stearyl alcohol[7] | 4.64 | 4.64 | 4.64 |
| Disodium EDTA | 0.13 | 0.13 | 0.13 |
| NaOH | 0.01 | 0.01 | 0.01 |
| Benzyl alcohol | 0.40 | 0.40 | 0.40 |
| Methylchloroisothiazolinone/ Methylisothiazolinone[8] | 0.0005 | 0.0005 | 0.0005 |
| Panthenol[9] | 0.10 | 0.10 | 0.10 |
| Panthenyl ethyl ether[10] | 0.05 | 0.05 | 0.05 |
| Fragrance | 0.35 | 0.35 | 0.35 |
| Fragrance Microcapsules (Example 3) | 1.2 | 1.2 | 1.2 |

[1]Glycidol Silicone VC2231-193
[2]Glycidol Silicone VC2231-193F
[3]Glycidol Silicone VC2231-193A
[4]Cyclopentasiloxane: SF1202 available from Momentive Performance Chemicals
[5]Behenyl trimethyl ammonium chloride/Isopropyl alcohol: Genamin™ KMP available from Clariant
[6]Cetyl alcohol: Konol ™ series available from Shin Nihon Rika
[7]Stearyl alcohol: Konol ™ series available from Shin Nihon Rika
[8]Methylchloroisothiazolinone/Methylisothiazolinone: Kathon TM CG available from Rohm & Haas
[9]Panthenol: Available from Roche
[10]Panthenyl ethyl ether: Available from Roche

| Ingredient | EXAMPLE COMPOSITION | |
|---|---|---|
| | VII | VIII |
| Sodium Laureth Sulfate | 10.00 | 10.00 |
| Sodium Lauryl Sulfate | 1.50 | 1.50 |
| Cocamidopropyl betaine | 2.00 | 2.00 |
| Guar Hydroxypropyl trimonium chloride (1) | 0.40 | |
| Guar Hydroxypropyl trimonium chloride (2) | | 0.40 |
| Dimethicone (3) | 2.00 | 2.00 |
| Gel Network (4) | | 27.27 |
| Ethylene Glycol Distearate | 1.50 | 1.50 |
| 5-Chloro-2-methyl-4-isothiazolin-3-one, Kathon CG | 0.0005 | 0.0005 |
| Sodium Benzoate | 0.25 | 0.25 |
| Disodium EDTA | 0.13 | 0.13 |
| Perfume | 0.40 | 0.40 |
| Fragrance Microcapsules of Example 3 | 0.30 | 0.30 |
| Citric Acid/Sodium Citrate Dihydrate | pH QS | pH QS |
| Sodium Chloride/Ammonium Xylene Sulfonate | Visc. QS | Visc. QS |
| Water | QS | QS |

(1) Jaguar C17 available from Rhodia
(2) N-Hance 3269 (with Mol. W. of ~500,000 and 0.8 meq/g) available from Aqualon/Hercules
(3) Viscasil 330M available from General Electric Silicones
(4) Gel Networks; See Composition below. The water is heated to about 74° C. and the Cetyl Alcohol, Stearyl Alcohol, and the SLES Surfactant are added to it. After incorporation, this mixture is passed through a heat exchanger where it is cooled to about 35° C. As a result of this cooling step, the Fatty Alcohols and surfactant crystallized to form a crystalline gel network.

| Ingredient | Wt. % |
|---|---|
| Water | 86.14% |
| Cetyl Alcohol | 3.46% |
| Steary Alcohol | 6.44% |
| Sodium laureth-3 sulfate (28% Active) | 3.93% |
| 5-Chloro-2-methyl-4-isothiazolin-3-one, Kathon CG | 0.03% |

Example 28

Microcapsules in Lotion

|  | Example | | |
|---|---|---|---|
|  | I | II | III |
| PHASE A | | | |
| DC-9040[1] | 8.60 | 3.00 | 5.00 |
| Dimethicone | 4.09 | 4.00 | 4.00 |
| Polymethylsilsesquioxane[2] | 4.09 | 4.00 | 4.00 |
| Cyclomethicone | 11.43 | 0.50 | 11.33 |
| KSG-210[3] | 5.37 | 5.25 | 5.40 |
| Polyethylene wax[4] | 3.54 |  | 2.05 |
| DC-2503 Cosmetic Wax[5] | 7.08 | 10.00 | 3.77 |
| Hydrophobic TiO2 |  |  | 0.50 |
| Iron oxide coated Mica |  |  | 0.65 |
| TiO2 Coated Mica | 1.00 | 1.00 |  |
| Fragrance Particles of Example 3 | 1.00 | 1.00 | 1.00 |
| PHASE B | | | |
| Glycerin | 10.00 | 10.00 | 10.00 |
| Dexpanthenol | 0.50 | 0.50 | 0.50 |
| Pentylene Glycol | 3.00 | 3.00 | 3.00 |
| Hexamidine Diisethionate[6] | 0.10 | 0.10 | 0.10 |
| Niacinamide[7] | 5.00 | 5.00 | 5.00 |
| Methylparaben | 0.20 | 0.20 | 0.20 |
| Ethylparaben | 0.05 | 0.05 | 0.05 |
| Sodium Citrate | 0.20 | 0.20 | 0.20 |
| Citric Acid | 0.03 | 0.03 | 0.03 |
| Sodium Benzoate | 0.05 | 0.05 | 0.05 |
| Sodium Chloride | 0.50 | 0.50 | 0.50 |
| FD&C Red #40 (1%) | 0.05 | 0.05 | 0.05 |
| Water | q.s to 100 | q.s to 100 | q.s to 100 |
| Hardness at 21° C. (g) | 33.3 | 15.4 | 14.2 |
| Hardness at 33° C. (g) | 6.4 | 0.7 | 4.0 |

[1]12.5% Dimethicone Crosspolymer in Cyclopentasiloxane. Available from Dow Corning ™.
[2]E.g., Tospearl ™ 145A or Tospearl 2000. Available from GE Toshiba Silicone ™.
[3]25% Dimethicone PEG-10/15 Crosspolymer in Dimethicone. Available from Shin-Etsu ™.
[4]Jeenate ™ 3H polyethylene wax from Jeen ™
[5]Stearyl Dimethicone. Available from Dow Corning.
[6]Hexamidine diisethionate, available from Laboratoires Serobiologiques.
[7]Additionally or alternatively, the composition may comprise one or more other skin care actives, their salts and derivatives, as disclosed herein, in amounts also disclosed herein as would be deemed suitable by one of skill in the art.

For the examples above, in a suitable container, combine the ingredients of Phase A. In a separate suitable container, combine the ingredients of Phase B. Heat each phase to 73° C.-78° C. while mixing each phase using a suitable mixer (e.g., Anchor blade, propeller blade, or IKA T25) until each reaches a substantially constant desired temperature and is homogenous. Slowly add Phase B to Phase A while continuing to mix Phase A. Continue mixing until batch is uniform. Pour product into suitable containers at 73-78° C. and store at room temperature. Alternatively, continuing to stir the mixture as temperature decreases results in lower observed hardness values at 21 and 33° C.

Example 29

Microcapsules in Single Unit Dose Personal Care Product

The following surfactant/polymer liquid processing composition is prepared at the indicated weight percentages as described in Table 1 below.

TABLE 1

| Component | |
|---|---|
| Glycerin | 3.2 |
| Polyvinyl alcohol[1] | 8.1 |
| Sodium Lauroamphoacetate (26% activity)[2] | 31.8 |
| Ammonium Laureth-3 sulfate (25% activity) | 4.9 |
| Ammonium Undecyl sulfate (24% activity) | 19.9 |
| Ammonium Laureth-1 sulfate (70% activity) | 8.0 |
| Cationic cellulose[3] | 0.5 |
| Citric Acid | 1.6 |
| Distilled water | 22.0 |
| Total | 100.0 |
| pH | 5.8 |
| Viscosity (cp) | 35,400 |

[1]Sigma-Aldrich Catalog No. 363081, MW 85,000-124,000, 87-89% hydrolyzed
[2]McIntyre Group Ltd, University Park, IL, Mackam HPL-28ULS
[3]UCARE ™ Polymer LR-400, available from Amerchol Corporation (Plaquemine, Louisiana)

A target weight of 300 grams of the above composition is prepared with the use of a conventional overhead stirrer (IKA® RW20DZM Stirrer available from IKA® Works, Inc., Wilmington, Del.) and a hot plate (Corning Incorporated Life Sciences, Lowell, Mass.). Into an appropriately sized and cleaned vessel, the distilled water and glycerin are added with stirring at 100-150 rpm. The cationic polymer, when present, is then slowly added with constant stiffing until homogenous. The polyvinyl alcohol is weighed into a suitable container and slowly added to the main mixture in small increments using a spatula while continuing to stir while avoiding the formation of visible lumps. The mixing speed is adjusted to minimize foam formation. The mixture is slowly heated to 80° C. after which surfactants are added. The mixture is then heated to 85° C. while continuing to stir and then allowed to cool to room temperature. Additional distilled water is added to compensate for water lost to evaporation (based on the original tare weight of the container). The final pH is between 5.2-6.6 and adjusted with citric acid or diluted sodium hydroxide if necessary. The resulting processing mixture viscosity is measured.

A porous dissolvable solid substrate (also referred to in the examples herein as "substrate") is prepared from the above liquid processing mixture as described in Table 2 below.

TABLE 2

| | |
|---|---|
| Aeration Time (sec) | 62 |
| Wet Density (g/cm³) | 0.26 |
| Oven Temperature (° C.) | 130 |
| Drying Time (min) | 38 |
| Average dry substrate weight (g) | 1.10 |
| Average dry substrate thickness (cm) | 0.62 |
| Average substrate shrinkage (%) | 4.6% |
| Average dry substrate density (g/cm³) | 0.11 |
| Average basis weight (g/m²) | 650 |

300 grams of the processing mixture is stored within a convection oven for greater than two hours at 70° C. to preheat the processing mixture. The mixture is then transferred into a pre-heated 5 quart stainless steel bowl (by placing into 70° C. oven for greater than 15 minutes) of a KITCHENAID® Mixer Model K5SS (available from Hobart Corporation, Troy, Ohio) fitted with a flat beater attachment and with a water bath attachment comprising tap water at 70-75° C. The mixture is vigorously aerated at a maximum speed setting of 10 until a wet density of approximately 0.26 grams/cm³ is achieved (time recorded in table). The density is measured by weighing a filling a cup with a known volume and evenly scraping off the top of the cup with a spatula. The resulting aerated mixture is then spread with a spatula into square 160 mm×160 mm aluminum molds with a depth of 6.5 mm with the excess wet foam being removed with the straight edge of a large metal spatula that is held at a 45° angle and slowly dragged uniformly across the mold surface. The aluminum molds are then placed into a 130° C. convection oven for approximately 35 to 45 minutes. The molds are allowed to cool to room temperature with the substantially dry porous dissolvable solid substrates removed from the molds with the aid of a thin spatula and tweezers.

Each of the resulting 160 mm×160 mm square substrates is cut into nine 43 mm×43 mm squares (with rounded edges) using a cutting die and a Samco SB20 cutting machine (each square representing surface area of approximately 16.9 cm$^2$). The resulting smaller substrates are then equilibrated overnight (14 hours) in a constant environment room kept at 70° F. and 50% relative humidity within large zip-lock bags that are left open to the room atmosphere.

Within a fume hood, the substrate is mounted on a stainless steel easel that rests at about a 60 degree angle and with notches holding the substrate from sliding downward and with a hole in plate so that the substrate can easily be removed from the mount by pushing from the easel. It is important that the top surface of the substrate (the side that is exposed to the air in the drying oven and opposite the side that is in direct contact with the aluminum mold during the drying process) is facing away from the easel. A small glass bottle with a pump spray is filled with the primary fragrance oil 1a and then sprayed onto the surface of the substrate from a distance of 2 to 3 inches. The substrate is then removed from the easel and returned to the weigh boat on the balance with the top side facing upwards. The weight of perfume applied is recorded and in the instance that the target weight is not achieved, either another spray amount is applied or a Kim wipe to absorb excess perfume away from the substrate. This iterative process is repeated until the target weight range is achieved.

The amount of fragrance 1a applied is recorded in the below table. The resulting substrate resting on the small weigh boat is stored within a zip-lock bag and sealed from the atmosphere. The above process is repeated on a second substrate.

The first substrate within its weigh boat is later removed from the zip-lock bag and tared again to zero weight on a 4 place weigh balance. A perfume microcapsule of Example 3 is then applied to the surface of each substrate. The substrate is coated with the perfume microcapsule by gently shaking the substrate in a tray (or other suitable container) containing an excess of the perfume inclusion complex in a side-to-side manner ten times (the process is repeated for the other side). The resulting coated substrate is then picked up (with gloved hands) and gently shaken and tapped several times to remove any excess powder that is not sufficiently adhered to the substrate. The resulting weight of the microcapsule of the secondary fragrance applied is recorded in the below table. The porous substrate within its weigh boat is then returned the zip lock bag and sealed from the atmosphere. This powder application process is repeated for the second substrate.

The final weights achieved are given in the below table:

| Substrate No. | Initial substrate weight | Weight of primary fragrance applied | Weight of perfume microcapsule of Example 3 |
|---|---|---|---|
| 1 | 1.194 | 0.050 | 0.0175 |
| 2 | 1.063 | 0.055 | 0.0150 |
| Averages | 1.129 | 0.053 | 0.0161 |

Example 30

Microcapsules in Antiperspirant/Deodorant

| Ingredient | Comparative Example I | Comparative Example II[9] | Example III | Example IV | Example V |
|---|---|---|---|---|---|
| Part I: Partial Continuous Phase | | | | | |
| Hexamethyldisiloxane[1] | 22.65 | 21.25 | 21.25 | 21.25 | 21.25 |
| DC5200[2] | 1.20 | 1.20 | 1.20 | 1.20 | |
| Fragrance | 0.35 | 1.25 | 1.25 | 1.25 | 1.25 |
| Fragrance Capsules of Example 3 | 1.00 | 1.00 | 1.00 | 1.00 | 1.00 |
| Shin Etsu KF 6038[3] | | | | | 1.20 |
| Part II: Disperse Phase | | | | | |
| ACH (40% solution)[4] | 40.00 | 55.0 | | | |
| IACH (34% solution)[5] | | 2.30 | 49.00 | | |
| ZAG (30% solution)[6] | | | | 52.30 | 52.30 |
| propylene glycol | 5.00 | | 5.00 | 5.00 | 5.00 |
| Water | 12.30 | | 3.30 | | |
| Part III: Structurant Plus Remainder of Continuous Phase | | | | | |
| FinSolve TN | 6.50 | 6.00 | 6.50 | 6.00 | 6.50 |
| Ozocrite Wax | | | | | 12.00 |
| Performalene PL[7] | 11.00 | 11.00 | 12.00 | 12.00 | |
| Aqueous Phase Conductivity (mS/cm) | 37.7 | 79.5 | 40.5 | 60.3 | 60.3 |

[1]DC 246 fluid from Dow Corning
[2]from Dow Corning
[3]from Shinetsu
[4]Standard aluminum chlorohydrate solution
[5]IACH solution stabilized with calcium
[6]IZAG solution stabilized with calcium
[7]from New Phase Technologies
[9]emulsion broke when manufacturing this composition The above examples I through V can be made via the following general process, which one skilled in the art will be able to alter to incorporate available equipment. The ingredients of Part I and Part II are mixed in separate suitable containers. Part II is then added slowly to Part I under agitation to assure the making of a water-in-silicone emulsion. The emulsion is then milled with suitable mill, for example a Greeco 1L03 from Greeco Corp, to create a homogenous emulsion. Part III is mixed and heated to 88° C. until the all solids are completely melted. The emulsion is then also heated to 88° C. and then added to the Part 3 ingredients. The final mixture is then poured into an appropriate container, and allowed to solidify and cool to ambient temperature.

| Ingredient | VI | VII | VIII | IX | X |
|---|---|---|---|---|---|
| Product Form | Solid Deodorant | Solid Deodorant | Solid Deodorant | Solid Deodorant | Deodorant or Body Spray |
| dipropylene glycol | 45 | 22 | 20 | 30 | 20 |
| propylene glycol | 22 | 45 | 22 | | |
| tripopylene glycol | | | 25 | | |
| Glycerine | | | | 10 | |
| PEG-8 | | | | 20 | |
| ethanol | | | | | QS |
| Water | QS | QS | QS | QS | |
| sodium stearate | 5.5 | 5.5 | 5.5 | 5.5 | |
| tetra sodium EDTA | 0.05 | 0.05 | 0.05 | 0.05 | |
| sodium hydroxide | 0.04 | 0.04 | 0.04 | 0.04 | |
| triclosan | 0.3 | 0.3 | 0.3 | 0.3 | |
| Fragramce | 0.5 | 0.5 | 0.5 | 0.5 | 0.5 |
| Fragrance capsules of Example 3 | 1.0 | 1.0 | 1.0 | 1.0 | 0.5 |
| dihydromyrcenol | 0.3 | .1 | 0.3 | 0.5 | .1 |
| Linalool | 0.2 | .15 | 0.2 | 0.25 | .15 |
| Propellant (1,1 difluoroethane) | | | | | 40 |

QS - indicates that this material is used to bring the total to 100%.

Examples VI to IX can be made as follows: all ingredients except the fragrance, linalool, and dihydromyrcenol are combined in a suitable container and heated to about 85° C. to form a homogeneous liquid. The solution is then cooled to about 62° C. and then the fragrance, linalool, and dihydromyrcenol are added. The mixture is then poured into an appropriate container and allowed to solidify up cooling to ambient temperature.

Example X can be made as follows: all the ingredients except the propellant are combined in an appropriate aerosol container. The container is then sealed with an appropriate aerosol delivery valve. Next air in the container is removed by applying a vacuum to the valve and then propellant is added to container through the valve. Finally an appropriate actuator is connected to the valve to allow dispensing of the product.

Example 31

Microcapsules in Rinse-Off Conditioner

| Components | Ex. I | Ex. II | Ex. III | Ex. IV | Ex. V | Ex. VI (Comparative example, w/PDMS instead of amino silicone) |
|---|---|---|---|---|---|---|
| Premix | | | | | | |
| Aminosilicone-1 *1 | 0.50 | 0.50 | | | | |
| Aminosilicone-2 *2 | | | 0.50 | 0.50 | 0.50 | |
| PDMS | | | | | | 0.50 |
| Fragrance microcapsules of Example 3 | ... | 1.0 | 1.0 | 1.0 | 1.0 | 1.0 |
| Gel matrix carrier | | | | | | |
| Behenyl trimethyl ammonium chloride | 2.30 | 2.30 | 2.30 | 2.30 | 2.30 | 2.30 |
| Cetyl alcohol | 1.5 | 1.5 | 1.5 | 1.5 | 1.5 | 1.5 |
| Stearyl alcohol | 3.8 | 3.8 | 3.8 | 3.8 | 3.8 | 3.8 |
| Deionized Water | QS | QS | QS | QS | QS | QS |
| Preservatives | 0.4 | 0.4 | 0.4 | 0.4 | 0.4 | 0.4 |
| Panthenol | — | — | 0.03 | — | — | — |
| Panthenyl ethyl ether | — | — | 0.03 | — | — | — |

Definitions of Components

*1 Aminosilicone-1 (AMD): having an amine content of 0.12-0.15 m mol/g and a viscosity of 3,000-8,000 mPa·s, which is water insoluble
*2 Aminosilicone-2 (TAS): having an amine content of 0.04-0.06 m mol/g and a viscosity of 10,000-16,000 mPa·s, which is water insoluble Method of Preparation The conditioning compositions of "Ex. I" through "Ex. VI" are prepared as follows: Cationic surfactants, high melting point fatty compounds are added to water with agitation, and heated to about 80° C. The mixture is cooled down to about 50° C. to form a gel matrix carrier. Separately, slurries of perfume microcapsules and silicones are mixed with agitation at room temperature to form a premix. The premix is added to the gel matrix carrier with agitation. If included, other ingredients such as preservatives are added with agitation. Then the compositions are cooled down to room temperature.

The conditioning composition of "Ex. II" is prepared as follows:
Cationic surfactants, high melting point fatty compounds are added to water with agitation, and heated to about 80° C. The mixture is cooled down to about 50° C. to form a gel matrix carrier. Then, silicones are added with agitation. Separately, slurries of perfume microcapsules, and if included, other ingredients such as preservatives are added with agitation. Then the compositions are cooled down to room temperature.

Example 32

Microcapsules in a Body Cleansing Composition

| | Example D | Example E | Example F |
|---|---|---|---|
| I: Cleansing Phase Composition | | | |
| Sodium Trideceth Sulfate (sulfated from Iconol TDA-3 (BASF Corp.) to >95% sulfate) | 5.9 | 5.9 | 5.9 |
| Sodium Lauryl Sulfate (Procter and Gamble) | 5.9 | 5.9 | 5.9 |
| Sodium Lauroamphoacetate (Cognis Chemical Corp.,) | 3.6 | 3.6 | 3.6 |
| Guar Hydroxypropyltrimonium Chloride (N-Hance 3196 from Aqualon) | — | 0.3 | 0.7 |
| Guar Hydroxypropyltrimonium Chloride (Jaguar C-17 from Rhodia) | 0.6 | — | — |

-continued

|  | Example D | Example E | Example F |
|---|---|---|---|
| Stabylen 30 (Acrylates/Vinyl Isodecanoate, 3V) | 0.33 | 0.33 | 0.33 |
| Sodium Chloride | 3.75 | 3.75 | 3.75 |
| Trideceth-3 (Iconal TDA-3 from BASF Corp.) | 1.75 | 1.75 | 1.75 |
| Methyl chloro isothiazolinone and methyl isothiazolinone (Kathon CG, Rohm & Haas) | 0.033 | 0.033 | 0.033 |
| EDTA (Dissolvine NA 2x) | 0.15 | 0.15 | 0.15 |
| Sodium Benzoate | 0.2 | 0.2 | 0.2 |
| Citric Acid, titrate | pH = 5.7 ± 0.2 | pH = 5.7 ± 0.2 | pH = 5.7 ± 0.2 |
| Perfume | 1.11% | 1.11% | 1.11% |
| Water and Minors (NaOH) | Q.S. | Q.S. | Q.S. |
| II: Benefit Phase Composition |  |  |  |
| Petrolatum (G2218 from Sonnerbonn) | 60 | 60 | 60 |
| Mineral Oil (Hydrobrite 1000 from Sonnerbonn) | 20 | 20 | 20 |
| Fragrance Microcapsules of Example 3 | 10 | 10 | 10 |
| III: Surfactant Phase:Benefit Phase Blending Ratio | 50:50 | 90:10 | 90:10 |

Example 33

Microcapsules in Fabric Softening Product

Non-limiting examples of product formulations containing purified perfume microcapsules of the aforementioned examples are summarized in the following table.

| (% wt) | A | B | C | D | E | F | G | H | I | J |
|---|---|---|---|---|---|---|---|---|---|---|
| FSA [a] | 14 | 16.47 | 14 | 12 | 12 | 16.47 | — | — | 5 | 5 |
| FSA [b] |  |  |  |  | — |  | 3.00 | — |  |  |
| FSA [c] |  |  |  |  | — |  | — | 6.5 |  |  |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Starch [d] | 1.25 | 1.47 | 2.00 | 1.25 | — | 2.30 | 0.5 | 0.70 | 0.71 | 0.42 |
| Microcapsule (% active)* | 0.6 | 0.75 | 0.6 | 0.75 | 0.37 | 0.60 | 0.37 | 0.6 | 0.37 | 0.37 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250[j] | 5 | 5 |
| Antifoam [k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant [l] | 0.01 | 0.01 | 0.01 | 0.01 | 0.01 | 0.01 | 0.01 | 0.01 | 0.01 | 0.01 |
| Neat Unencapsulated Perfume | 0.8 | 0.7 | 0.9 | 0.5 | 1.2 | 0.5 | 1.1 | 0.6 | 1.0 | 0.9 |
| Deionized Water | Balance | Balance | Balance | Balance | Balance | Balance | Balance | Balance | Balance | Balance |

[a] N,N-di(tallowoyloxyethyl)-N,N-dimethylammonium chloride.
[b] Methyl bis(tallow amidoethyl)2-hydroxyethyl ammonium methyl sulfate.
[c] Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the trade name DC2310.
[l] Hydrophobically-modified ethoxylated urethane available from Rohm and Haas under the tradename Aculyn™ 44.
* Suitable combinations of the microcapsules provided in Examples 1 to 25. (Percent active relates to the core content of the microcapsule.)

Example 34

Microcapsules in Dry Laundry Formulations

Non-limiting examples of product formulations containing purified perfume microcapsules of the aforementioned examples are summarized in the following table.

|  | % w/w granular laundry detergent composition | | | | | | |
|---|---|---|---|---|---|---|---|
| Component | A | B | C | D | E | F | G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | 29.6 | 29.8 | 38.8 | 15.1 | 24.4 | 19.7 | 19.1 |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| PDMS/clay agglomerates (9.5% wt % active PDMS) | 10.5 | 10.3 | 5 | 15 | 5.1 | 7.3 | 10.2 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Perfume oil | 0.5 | 0.5 | 0.5 | 0.5 | 0.5 | 0.5 | 0.5 |
| Solid perfume particles | 0.4 | 0 | 0.4 | 0.4 | 0.4 | 0.4 | 0.6 |
| Perfume microcapsules* | 1.3 | 2.4 | 1 | 1.3 | 1.3 | 1.3 | 0.7 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

*Microcapsule added as 25-35% active slurry (aqueous solution). Core/wall ratio can range from 80/20 up to 90/10 and average particle diameter can range from 5 μm to 50 μm, and can be purified via any of the aforementioned examples. Exemplary microcapsules that are suitable for formulating are provided in examples 1 through 25.

Example 35

Liquid Laundry Formulations (HDLs)

Non-limiting examples of product formulations containing purified perfume microcapsules of the aforementioned examples are summarized in the following table.

| Ingredient | HDL 1 | HDL 2 | HDL3 | HDL4 | HDL 5 | HDL 6 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |

-continued

| Ingredient | HDL 1 | HDL 2 | HDL3 | HDL4 | HDL 5 | HDL 6 |
|---|---|---|---|---|---|---|
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Perfume | 0.7 | 0.5 | 0.8 | 0.8 | 0.6 | 0.6 |
| Polyethyleneimine | 0.01 | 0.10 | 0.00 | 0.10 | 0.20 | 0.05 |
| Perfume Microcapsules* | 1.00 | 5.00 | 1.00 | 2.00 | 0.10 | 0.80 |
| Water | Balance to 100% | Balance to 100% | Balance to 100% | Balance to 100% | Balance to 100% | Balance to 100% |

*Microcapsule added as 25-35% active slurry (aqueous solution). Core/wall ratio can range from 80/20 up to 90/10 and average particle diameter can range from 5 μm to 50 μm, and can be purified via any of the aforementioned examples. Exemplary microcapsules that are suitable for formulating are provided in examples 1 through 25.

Non-limiting examples of product formulations containing purified perfume microcapsules of the aforementioned examples are summarized in the following table.

| Examples of liquid detergents | A | B | C | D |
|---|---|---|---|---|
| C14-C15 alkyl poly ethoxylate (8) | 6.25 | 4.00 | 6.25 | 6.25 |
| C12-C14 alkyl poly ethoxylate (7) | 0.40 | 0.30 | 0.40 | 0.40 |
| C12-C14 alkyl poly ethoxylate (3) sulfate Na salt | 10.60 | 6.78 | 10.60 | 10.60 |
| Linear Alkylbenzene sulfonate acid | 0.19 | 1.16 | 0.79 | 0.79 |
| Citric Acid | 3.75 | 2.40 | 3.75 | 3.75 |
| C12-C18 Fatty Acid | 4.00 | 2.56 | 7.02 | 7.02 |
| Enzymes | 0.60 | 0.4 | 0.60 | 0.60 |
| Boric Acid | 2.4 | 1.5 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.09 | 0.06 | 0.14 | 0.14 |
| Hydrogenated Castor Oil | 0.05 | 0.300 | 0.20 | 0.20 |
| Ethanol | 2.50 | 1.00 | 2.50 | 2.50 |
| 1,2 propanediol | 1.14 | 0.7 | 1.14 | 1.14 |
| Sodium hydroxide | 3.8 | 2.6 | 4.60 | 4.60 |
| Mono Ethanol Amine | 0.8 | 0.5 | | |
| Na Cumene Sulphonate | | | | |
| Silicone emulsion | 0.0030 | 0.0030 | 0.0030 | 0.0030 |
| Dye | 0.002 | 0.002 | 0.002 | 0.002 |
| Opacifier (Styrene Acrylate based) | | | | |
| Bentonite Softening Clay | | | | |
| Acrylamide/MAPTAC (ex Nalco Chemicals of Naperville, IL) | | | 0.40 | 0.40 |
| Mirapol 550 (ex Rhodia Chemie, France) | | | | |
| Polyquaternium 10-Cationic hydroxyl ethyl cellulose | | | | |
| PP-5495 (silicone ex Dow Corning Corporation, Midland, MI) | | | | |
| DC 1664 (silicone ex Dow Corning Corporation, Midland, MI) | | | | |
| Pearlescent agent* | | | | 0.2 |
| Perfume micro capsules** (expressed as perfume oil) | 0.8 | 0.5 | 1.0 | 0.7 |

-continued

| Examples of liquid detergents | A | B | C | D |
|---|---|---|---|---|
| Perfume | 0.7 | 0.55 | 1.00 | 1.00 |
| Poly Ethylene Imine MW 25000 | | | | |
| Water | Up to 100 | Up to 100 | Up to 100 | Up to 100 |

*Mica-$TiO_2$ (Prestige Silk Silver Star ex Eckart) or BiOCl (Biron Silver CO-Merck) or pre-crystallized EGDS (Tegopearl N 100 ex Degussa, expressed as pure EGDS)
**Microcapsule added as 25-35% active slurry (aqueous solution). Core/wall ratio can range from 80/20 up to 90/10 and average particle diameter can range from 5 μm to 50 μm, and can be purified via any of the aforementioned examples. Exemplary microcapsules that are suitable for formulating are provided in examples 1 through 25.

| Examples of liquid detergents | E | F | G | H |
|---|---|---|---|---|
| C14-C15 alkyl poly ethoxylate (8) | 6.25 | 4.00 | 6.25 | 6.25 |
| C12-C14 alkyl poly ethoxylate (7) | 0.40 | 0.30 | 0.40 | |
| C12-C14 alkyl poly ethoxylate (3) sulfate Na salt | 10.60 | 6.78 | 10.60 | 10.60 |
| Linear Alkylbenzene sulfonate acid | 0.79 | 1.19 | 0.79 | 0.79 |
| Citric Acid | 3.75 | 2.40 | 3.75 | 3.75 |
| C12-C18 Fatty Acid | 7.02 | 4.48 | 7.02 | 7.02 |
| Enzymes | 0.60 | 1.0 | 0.60 | |
| Boric Acid | 1.25 | 1.25 | 1.25 | 1.25 |
| Trans-sulphated ethoxylated hexamethylene diamine quat | 1.11 | 0.71 | 1.11 | 1.11 |
| Diethylene triamine penta methylene phosphonic acid | 0.17 | 0.11 | 0.17 | 0.17 |
| Fluorescent brightener | 0.14 | 0.06 | 0.14 | |
| Hydrogenated Castor Oil | 0.20 | 0.300 | 0.20 | 0.20 |
| Ethanol | 2.50 | 1.00 | 2.50 | 2.50 |
| 1,2 propanediol | 1.14 | 0.09 | 1.14 | 1.14 |
| Sodium hydroxide | 4.60 | 3.01 | 4.60 | 4.60 |
| Mono Ethanol Amine | | | | |
| Na Cumene Sulphonate | | | | |
| Silicone emulsion | 0.0030 | 0.0030 | 0.0030 | 0.0030 |
| Dye | 0.002 | 0.00084 | 0.00084 | 0.00084 |
| Opacifier (Styrene Acrylate based) | | | | 0.1 |
| Bentonite Softening Clay | | | | |
| Acrylamide/MAPTAC (ex Nalco Chemicals of Naperville, IL) | | | 0.40 | |
| Mirapol 550 (ex Rhodia Chemie, France) | 0.40 | 0.25 | | |
| Polyquaternium 10-Cationic hydroxyl ethyl cellulose | | | | 0.30 |
| PP-5495 (silicone ex Dow Corning Corporation, Midland, MI) | | 3.0 | | |
| DC 1664 (silicone ex Dow Corning Corporation, Midland, MI) | 3.0 | | 3.0 | |
| Pearlescent agent* | | | 0.2 | |
| Perfume micro capsules** (expressed as perfume oil) | 0.9 | 0.3 | 0.5 | 1.2 |
| Perfume | 1.00 | 0.65 | 1.00 | 1.00 |
| Poly Ethylene Imine MW 25000 | | | | |
| Water | Up to 100 | Up to 100 | Up to 100 | Up to 100 |

*Mica-$TiO_2$ (Prestige Silk Silver Star ex Eckart) or BiOCl (Biron Silver CO-Merck) or pre-crystallized EGDS (Tegopearl N 100 ex Degussa, expressed as pure EGDS)
**Microcapsule added as 25-35% active slurry (aqueous solution). Core/wall ratio can range from 80/20 up to 90/10 and average particle diameter can range from 5 μm to 50 μm, and can be purified via any of the aforementioned examples. Exemplary microcapsules that are suitable for formulating are provided in examples 1 through 25.

| Examples of liquid detergents | I | J | K |
|---|---|---|---|
| C14-C15 alkyl poly ethoxylate (8) | 4.00 | 6.1 | |
| C12-C14 alkyl poly ethoxylate (7) | | | 2.00 |
| C12-C14 alkyl poly ethoxylate (3) sulfate Na salt | 6.78 | | |
| Linear Alkylbenzene sulfonate acid | 1.19 | 7.8 | 15.0 |
| Citric Acid | 2.40 | 2.6 | 2.50 |
| C12-C18 Fatty Acid | 4.48 | 2.6 | 11.4 |
| Enzymes | | .55 | .07 |
| Boric Acid | 1.25 | 1.50 | 1.3 |
| Trans-sulphated ethoxylated hexamethylene diamine quat | 0.71 | 1.20 | |
| Diethylene triamine penta methylene phosphonic acid | 0.11 | 0.20 | 0.7 |
| Fluorescent brightener | | 0.09 | 0.14 |
| Hydrogenated Castor Oil | 0.300 | 0.45 | 0.09 |
| Ethanol | 1.00 | 1.40 | 0.7 |
| 1,2 propanediol | 0.09 | 3.30 | 6.7 |
| Sodium hydroxide | 3.01 | 3.00 | 5.5 |
| Mono Ethanol Amine | | 0.50 | |
| Na Cumene Sulphonate | | | 1.6 |
| Silicone emulsion | 0.0030 | 0.0030 | 0.30 |

-continued

| Examples of liquid detergents | I | J | K |
|---|---|---|---|
| Dye | 0.00084 | 0.02 | 0.004 |
| Opacifier (Styrene Acrylate based) | | | |
| Bentonite Softening Clay | | | 3.40 |
| Acrylamide/MAPTAC (ex Nalco Chemicals of Naperville, IL) | | | |
| Mirapol 550 (ex Rhodia Chemie, France) | | | |
| Polyquaternium 10-Cationic hydroxyl ethyl cellulose | 0.18 | | |
| PP-5495 (silicone ex Dow Corning Corporation, Midland, MI) | | | |
| DC 1664 (silicone ex Dow Corning Corporation, Midland, MI) | 3.0 | | |
| Pearlescent agent * | 0.2 | | |
| Perfume micro capsules (expressed as perfume oil) | 0.2 | 0.45 | 0.75 |
| Perfume | 0.65 | 0.5 | 1.0 |
| Poly Ethylene Imine MW 25000 | | | 0.08 |
| Water | Up to 100 | Up to 100 | Up to 100 |

| Examples of liquid detergents | L | M** | N |
|---|---|---|---|
| C14-C15 alkyl poly ethoxylate (8) | 3.7 | | 20.7 |
| C12-C14 alkyl poly ethoxylate (7) | | 16.7 | |
| C12-C14 alkyl poly ethoxylate (3) sulfate Na salt | 17.8 | | 5.5 |
| Linear Alkylbenzene sulfonate acid | 12.5 | 22.9 | 13.5 |
| Citric Acid | 3.9 | | 1.7 |
| C12-C18 Fatty Acid | 11.1 | 18 | 5.1 |
| Enzymes | 3 | 1.2 | 3 |
| Boric Acid | 0.5 | | 0.5 |
| Trans-sulphated ethoxylated hexamethylene diamine quat | 3.25 | | 1.2 |
| PEI 600 EO20 | 1.25 | | 1.2 |
| Diethylene triamine penta methylene phosphonic acid or HEDP | 1.6 | | 0.85 |
| Fluorescent brightener | 0.2 | 0.3 | 0.14 |
| Hydrogenated Castor Oil | | 0.2 | |
| 1,2 propanediol | 4.3 | 20.3 | 11.7 |
| Sodium hydroxide | | 1.0 | 3.9 |
| Mono Ethanol Amine | 9.8 | 6.8 | 3.1 |
| Dye | Present | Present | Present |
| PDMS | | 2.15 | |
| Potassium sulphite | | 0.2 | |
| Perfume micro capsules* (expressed as perfume oil) | 1.6 | 1.5 | 1.4 |
| Perfume | 1.2 | 1.6 | 1.0 |
| Form. Phenyl Boronic Acid | | | Present |
| Water | Up to 100 | Up to 100 | Up to 100 |

*Microcapsule added as 25-35% active slurry (aqueous solution). Core/wall ratio can range from 80/20 up to 90/10 and average particle diameter can range from 5 μm to 50 μm, and can be purified via any of the aforementioned examples. Exemplary microcapsules that are suitable for formulating are provided in examples 1 through 25.
**Low water liquid detergent in Polyvinylalcohol unidose/sachet

Example 36

Liquid and Gel Detergents

TABLE 1

| Ingredients | (% by Weight) | | |
|---|---|---|---|
| | 33 | 34 | 35 |
| Alkylbenzenesulfonic acid | 17.2 | 12.2 | 23 |
| C12-14 alcohol 7-ethoxylate | 8.6 | 0.4 | 19.5 |
| C14-15 alcohol 8-ethoxylate | — | 9.6 | — |
| C12-14 alcohol 3-ethoxylate sulphate, Na salt | 8.6 | — | — |
| C8-10 Alkylamidopropyldimethyl amine | — | — | 0.9 |
| Citric acid | 2.9 | 4.0 | — |
| C12-18 fatty acid | 12.7 | 4.0 | 17.3 |
| Enzymes | 3.5 | 1.1 | 1.4 |
| Ethoxylated polyimine | 1.4 | — | 1.6 |
| Ethoxylated polyimine polymer, quaternized and sulphated | 3.7 | 1.8 | 1.6 |
| Hydroxyethane diphosphonic acids (HEDP) | 1.4 | — | — |
| Pentamethylene triamine pentaphosphonic acid | — | 0.3 | — |
| Catechol 2,5 disulfonate, Na salt | 0.9 | — | — |
| Fluorescent whitening agent | 0.3 | 0.15 | 0.3 |
| 1,2 propandiol | 3.5 | 3.3 | 22 |
| Ethanol | — | 1.4 | — |
| Diethylene glycol | — | 1.6 | — |
| 1-ethoxypentanol | 0.9 | — | — |
| Sodium cumene sulfonate | — | 0.5 | — |
| Monoethanolamine (MEA) | 10.2 | 0.8 | 8.0 |
| MEA borate | 0.5 | 2.4 | — |
| Sodium hydroxide | — | 4.6 | — |
| Perfume | 1.6 | 0.7 | 1.5 |
| Perfume microcapsules as Example 2 | 1.1 | 1.2 | 0.9 |
| Water | 22.1 | 50.8 | 2.9 |
| Perfume, dyes, miscellaneous minors | Balance | Balance | Balance |
| Undiluted viscosity ($V_n$) at 20 $s^{-1}$, cps | 2700 | 400 | 300 |

**Microcapsule added as 25-35% active slurry (aqueous solution). Core/wall ratio can range from 80/20 up to 80/10 and average particle diameter can range from 5 μm to 50 μm, and can be purified via any of the aforementioned examples. Exemplary microcapsules that are suitable for formulating are provided in examples 1 through 25.

Examples 37

Liquid Unit Dose

The following are examples of unit dose executions wherein the liquid composition is enclosed within a PVA film. The preferred film used in the present examples is Monosol M8630 76 μm thickness.

| | D 3 compartments | | | E 2 compartments Compartment # | | F 3 compartments | | |
|---|---|---|---|---|---|---|---|---|
| | 42 | 43 | 44 | 45 | 46 | 47 | 48 | 49 |
| | Dosage (g) | | | | | | | |
| Ingredients | 34.0 | 3.5 | 3.5 | 30.0 | 5.0 | 25.0 | 1.5 | 4.0 |
| | Weight % | | | | | | | |
| Alkylbenzene sulfonic acid | 20.0 | 20.0 | 20.0 | 10.0 | 20.0 | 20.0 | 25 | 30 |
| Alkyl sulfate | | | | 2.0 | | | | |
| $C_{12-14}$ alkyl 7-ethoxylate | 17.0 | 17.0 | 17.0 | | 17.0 | 17.0 | 15 | 10 |
| $C_{12-14}$ alkyl ethoxy 3 sulfate | 7.5 | 7.5 | 7.5 | | | 7.5 | 7.5 | |
| Citric acid | 0.5 | | 2.0 | 1.0 | | | | 2.0 |
| Zeolite A | | | | 10.0 | | | | |
| $C_{12-18}$ Fatty acid | 13.0 | 13.0 | 13.0 | | 18.0 | 18.0 | 10 | 15 |
| Sodium citrate | | | | 4.0 | 2.5 | | | |
| enzymes | 0-3 | 0-3 | 0-3 | 0-3 | | 0-3 | 0-3 | 0-3 |
| Sodium Percarbonate | | | | 11.0 | | | | |
| TAED | | | | 4.0 | | | | |
| Polycarboxylate | | | | 1.0 | | | | |
| Ethoxylated Polyethylenimine[1] | 2.2 | 2.2 | 2.2 | | | | | |
| Hydroxyethane diphosphonic acid | 0.6 | 0.6 | 0.6 | 0.5 | | | 2.2 | |

-continued

| | D<br>3<br>compartments | | | E<br>2<br>compartments | | F<br>3<br>compartments | | |
|---|---|---|---|---|---|---|---|---|
| Compartment # | | | | | | | | |
| | 42 | 43 | 44 | 45 | 46 | 47 | 48 | 49 |
| Dosage (g) | | | | | | | | |
| | 34.0 | 3.5 | 3.5 | 30.0 | 5.0 | 25.0 | 1.5 | 4.0 |
| Ingredients | | | | Weight % | | | | |
| Ethylene diamine tetra(methylene phosphonic) acid | | | | | 0.4 | | | |
| Brightener | 0.2 | 0.2 | 0.2 | 0.3 | | 0.3 | | |
| Microcapsules ** | 0.4 | 1.2 | 1.5 | 1.3 | 1.3 | 0.4 | 0.12 | 0.2 |
| Water | 9 | 8.5 | 10 | 5 | 11 | 10 | 10 | 9 |
| CaCl2 | | | | | | | 0.01 | |
| Perfume | 1.7 | 1.7 | | 0.6 | | 1.5 | 0.5 | |
| Minors (antioxidant, sulfite, aesthetics, . . . ) | 2.0 | 2.0 | 2.0 | 4.0 | 1.5 | 2.2 | 2.2 | 2.0 |
| Buffers (sodium carbonate, mono-ethanolamine) [3] | To pH 8.0 for liquids<br>To RA > 5.0 for powders | | | | | | | |
| Solvents (1,2 propanediol, ethanol), Sulfate | To 100 p | | | | | | | |

[1]Polyethylenimine (MW = 600) with 20 ethoxylate groups per —NH.
[3] RA = Reserve Alkalinity (g NaOH/dose)
** Microcapsule added as 25-35% active slurry (aqueous solution). Core/wall ratio can range from 80/20 up to 90/10 and average particle diameter can range from 5 μm to 50 μm, and can be purified via any of the aforementioned examples. Exemplary microcapsules that are suitable for formulating are provided in examples 1 through 25.

Example 38

Centrifugation of PMC Slurry 14 milliliters of the aqueous suspension of perfume microcapsules of Example 3 are placed in a 20 milliliter centrifuge tube. 6 identical such tubes are prepared and placed in a batch centrifuge (IEC Centra CL2). After 20 minutes at 3800 RPM, the centrifuge tubes are removed. The top microcapsule layer is isolated from the remaining material. This material contains approximately 20 wt % water, and can be incorporated into low water containing formulations.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising:
   an adjunct ingredient; and
   a plurality of non-anionic microcapsule particles comprising:
      an oil soluble or dispersible core material; and
      a wall material at least partially surrounding the core material, the wall material comprising:
         a plurality of amine monomers selected from the group consisting of aminoalkyl acrylates, aminoalkyl methacrylates, and combinations thereof; and
      a plurality of multifunctional monomers or multifunctional oligomers; and
      wherein the plurality of non-anionic microcapsule particles have a zeta potential of −6 mV or greater; and
   wherein said composition is a consumer product.

2. The composition of claim 1, wherein the non-anionic microcapsule particles are cationic microcapsule particles.

3. The composition of claim 1, wherein the plurality of amine monomers comprise aminoalkyl methacrylate selected from the group consisting of tertiarybutyl aminethyl methacrylates, diethylaminoethyl methacrylates, dimethylaminoethyl methacrylates, and combinations thereof.

4. The composition of claim 1, wherein the multifunctional monomers or multifunctional oligomers are selected from the group consisting of polyvinyl monomers, polyvinyl oligomers, vinyl monomers, vinyl oligomers, acrylate monomers, acrylate oligomers, methacrylate monomers, methacrylate oligomers, and combinations thereof.

5. The composition of claim 1, wherein the oil soluble or dispersible core material comprises a perfume oil.

6. The composition of claim 1, wherein the oil soluble or dispersible core material comprises a partitioning modifier.

7. The composition of claim 1, wherein the oil soluble or dispersible core material comprises a partitioning modifier that has a ClogP greater than about 4.

8. The composition of claim 1, wherein the oil soluble or dispersible core material comprises a partitioning modifier; wherein said partitioning modifier is isopropyl myristate.

9. The composition of claim 1, wherein said composition further comprises from 5% to 50% of a detersive surfactant by concentration of the composition.

10. The composition of claim 1, wherein said composition further comprises from 0.1% to 10% of a cationic surfactant system by weight of the composition.

11. The composition of claim 1, wherein said adjunct ingredient is selected from the group consisting of polymers, surfactants, builders, chelating agents, dye transfer inhibiting agents, dispersants, enzymes, enzyme stabilizers, catalytic materials, bleach activators, polymeric dispersing agents, clay soil removal/anti-redeposition agents, brighteners, dye polymer conjugates, dye clay conjugates, suds suppressors, dyes, bleach catalysts, additional perfume and/or perfume delivery systems, structure elasticizing agents, fabric softeners, carriers, hydrotropes, processing aids, rheology modifiers, structurants, thickeners, pigments, water, and mixtures thereof.

12. The composition of claim 1, wherein said composition further comprises a material selected from the group consisting of dyes, perfume, optical brighteners, rheology modifiers, structurants, thickeners, deposition aids, and mixtures thereof.

13. The composition of claim 1, wherein said composition further comprises a deposition aid that comprises a polymer selected from the group consisting of: polysaccharides; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide; polyvinyl alcohol; polyvinyl alcohol crosslinked with boric acid; polyacrylic acid; polyglycerol ether silicone crosspolymers; polyacrylic acids; polyacrylates; copolymers of polyvinylamine and polvyinylalcohol oligimers of amines; polymeric compounds comprising, at least two moieties selected from the moieties consisting of a carboxylic acid moiety, an amine moiety, a hydroxyl moiety, and a nitrile moiety on a backbone of polybutadiene, polyisoprene, polybutadiene/styrene, polybutadiene/acrylonitrile, carboxyl-terminated polybutadiene/acrylonitrile, and combinations thereof; pre-formed coacervates of anionic surfactants combined with cationic polymers; polyamines; and mixtures thereof.

14. A composition according to claim 1, wherein said composition further comprises a rheology modifier, thickener and/or structurant having a high shear viscosity, at 20 $s^{-1}$ shear rate and at 21° C., of from 1 to 7000 cps and a viscosity at low shear (0.5 $s^{-1}$ shear rate at 21° C.) of greater than 1000 cps; wherein the rheology modifiers, thickeners and/or structurants is/are selected from the group consisting of polyacrylates, polymethacrylates, polycarboxylates, polymeric gums, non-gum polysaccharides, hydroxyl-containing fatty acids, fatty esters, fatty waxes, castor oil; derivatives thereof; and mixtures thereof.

15. A composition according to claim 1, wherein said composition is a fluid detergent and comprises, based on total fluid detergent weight, less than about 80% water.

16. A composition according to claim 1, wherein said composition is a gel comprising, based on total gel weight, less than about 45% water and a neat viscosity of from about 1,000 cps to about 10,000 cps.

17. A composition according to claim 1, wherein said composition is selected from the group consisting of a fluid fabric enhancer; a solid fabric enhancer; a fluid shampoo; a solid shampoo; a hair conditioner; a body wash; a solid antiperspirant; a fluid antiperspirant; a solid deodorant; a fluid deodorant; a fluid detergent; a solid detergent; a fluid hard surface cleaner; a solid hard surface cleaner; and a unit dose detergent comprising a detergent and a water soluble film encapsulating said detergent.

18. The composition of claim 1, wherein said composition comprises less than 4% of free oil.

19. The composition of claim 1, wherein said microcapsule particles comprise a material selected from the group consisting of chromogens, dyes, perfumes, flavorants, sweeteners, oils, pigments, pharmaceutics, moldicides, herbides, fertilizers, phase change materials, and adhesives.

20. The composition of claim 1, wherein the composition further comprises a surfactant selected from the group consisting of sodium laureth sulfate, sodium lauryl sulfate, cocamidopropyl betaine, and mixtures thereof.

* * * * *